US006241963B1

(12) United States Patent
Kung et al.

(10) Patent No.: US 6,241,963 B1
(45) Date of Patent: Jun. 5, 2001

(54) DOPAMINE AND SEROTONIN TRANSPORTER LIGANDS AND IMAGING AGENTS

(75) Inventors: Hank Kung, Wynnewood; Sanath Meegalla, Drexel Hill; Mei-Ping Kung, Wynnewood, all of PA (US); Karl Plossl, Wilmington, DE (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 760 days.

(21) Appl. No.: 08/649,782

(22) Filed: May 17, 1996

Related U.S. Application Data

(63) Continuation-in-part of application No. 08/545,327, filed on Oct. 19, 1995, now abandoned.

(51) Int. Cl.[7] .......................... A61K 51/00; A61M 36/14

(52) U.S. Cl. ...................... 424/1.65; 424/1.11; 424/1.37; 424/9.1; 534/14; 546/124; 546/132

(58) Field of Search .................................. 424/1.11, 1.65, 424/9.1, 9.2, 9.3, 9.4, 9.5, 1.37; 534/7, 10–16; 206/223, 569, 570; 546/132, 1, 4–5, 10, 124

(56) References Cited

U.S. PATENT DOCUMENTS 5,175,343 * 12/1992 Fritzberg et al. .................... 560/145
5,980,860 * 11/1999 Kung et al. ......................... 424/1.65

OTHER PUBLICATIONS

Kung et al., "Imaging of dopamine transporters in humans with technetium–99m TRODAT–1", *Eur. J. Nucl. Med.*, 1996, 23(11), 1527–15230.
Mozley, et al., "Dosimetry of a D2/D3 Dopamine Receptor Antagonist That Can Be Used with PET or SPECT", *The Journal of Nuclear Medicine,* vol. 36, No. 7, Jul. 1995.
Mozley, et al., "Dosimetry of an Iodine–123–Labled Tropane to Image Dopamine Transporters", *The Journal of Nuclear Medicine,* vol. 37, No. 1, Jan. 1996.
Innis, R. B. et al. *Proc. Natl. Acad. Sci. U.S.A.* 1993, 90, 11965–11969.
Innis, R. B. *Eur. J. Nucl. Med.* 1994, 21, 1–5.
Frost, J. J. et al. *Ann. Neurol.* 1993, 34, 423–431.
Eckelman, W. C.*Nucl. Med. Biol.* 1992, 18, iii–v.
Fowler, J. S. et al.*Ann. Rep. Med. Chem.* 1989, 24, 277–286.
Fowler, J. S. et al.*Ann. Rep. Med. Chem.* 1990, 25, 261–268.
Kung, M.P. et al. *Synapse* 1995, 20, 316–324.
Malison, R. T. et al. *J. Nucl. Med.* 1995, in Press.
Mozley, P. D. et al. *J. Med. Chem.* 1994, 37, 1558–1561.
Del Rosario, R. B. et al. *Nucl. Med. Biol.* 1994, 21, 197–203.
Chi, D. Y. et al. *J. Med. Chem.* 1994, 37, 928–935.
DiZio, J. P. et al. *Biconj. Chem.* 1991, 2, 353–366.
DiZio, J. P. et al. *J. Nucl. Med.* 192, 33, 558–569.
O'Neil, J. P. et al. *Inorg. Chem.* 1994, 33, 319–323.
O'Neil, J. P. et al. *Bioconj. Chem.* 1994, 5, 182–193.
Jurisson, S. et al. *Chem. Rev.* 1993, 93, 1137–1156.
Jurisson, S. S. et al. *Nucl. Med. Biol.* 1995, 22, 269–281.
Jurisson, S. et al. *Chem. Rev.* 1993, 93, 1137–1156.
Lever, S. Z. et al. *Nucl. Med. Biol.* 1994, 21, 157–164.
Mastrostamatis, S. G. et al., *J. Med. Chem.* 1994, 37, 3212–3218.
Spies, H. et al., *Technetium and Rhenium in Chemistry and Nuclear Medicine,* 1995, 4, 243–246.
Spies, H. et al. *Angew. Chem. Int. Ed. Engl.* 1994, 33, 1354–1356.
Chi, D. Y. et al. *J. Amer. Chem. Soc.* 1993, 115, 7045–7046.
Chi, D. Y. et al. *J. Med. Chem.* 1994, 37, 928–935.
Meltzer, P. C. et al. *J. Med. Chem.* 1993, 36, 855–862.
Ohmomo, Y. et al. *J. Med. Chem.* 1992, 35, 157–162.
Kolb, U. et al. *Inorg. Chem.* 1994, 33, 4522–4530.
Dhar, T. G. M. et al. *J. Med. Chem.* 1994, 37, 2334–2342.
Kozikowski, A. P. et al., *J. Med. Chem.,* 1995, 38, 3086–3093.
Neumeyer, J. L. et al. *J. Med. Chem.* 1994, 37, 1558–1561.
Carroll, F.I., et al. *Med. Res. Rev.* 1995, 15, 419–444.
Carroll, F.I., et al. *Med. Chem.* 1994, 37, 2865–2873.
Carroll, F. I., et al. *J. Med. Chem.* 1995, 38, 379–388.
Yu, D.–W., et al. *J. Med. Chem.* 1992, 35, 2178–2183.
Fowler, J. S., et al. *Synapse* 1992, 12, 220–227.
Clarke, R. L. et al. *J. Med. Chem.* 1973, 16, 1260–1267.
Clarke, R. L. et al. *J. Med. Chem.* 1978, 21, 1235–1242.
Wong, D. F., et al. *Synapse* 1993, 15, 130–142.
Seibyl, J. P., et al. *J. Nucl. Med.* 1996, 37, 222–228.
Kuikka, J. T., et al. *Eur. J. Nucl. Med.* 1995, 22, 682–686.
Goodman, M. M. et al. *J. Med. Chem.* 1994, 37, 1535–1542.
Mozley, P.D., et al. *J. Nucl. Med.* 1996, 37, 151–159.
Kilbourn, M. R. *Life Sci.* 1988, 42, 1347–1353.
Meegalla, S. K. et al. *J. Am. Chem. Soc.* 1995, 117, 11037–11038.
Madras, B. K. et al. *Synapse* 1996, 22, 239–246.
Meegalla, et al., Synthesis and Characterization of Technetium–99m–Labeled Tropanes as Dopamine Transporter–Imaging Agents 1997, Journal of Medicinal Chemistry, vol. 40, No. 1, 9–17.
Meegalla et al (1997) J. Med. Chem., vol. 40, No. 1, pp. 9–17 Synthesis and Characterization of Technetium–99m Labeled Tropanes as dopamine transporter imaging agents.*
Kung et al (1996), Eur. J. Nuc. Med., vol. 23, No. 11, pp. 1527–1530, "Imaging of a dopamine transporter in humans with technetium–99m TRODAT–1".*

(List continued on next page.)

*Primary Examiner*—Dameron L. Jones
(74) *Attorney, Agent, or Firm*—Sterne, Kessler. Goldstein & Fox P.L.L.C.

(57) ABSTRACT

This invention presents a series novel tropane-based derivatives complexed with either technetium or rhenium that are specific for central nervous system receptors, in particular, dopamine or serotonin receptors. The compounds of the invention have utility, inter alia, as imaging agents for CNS receptors. Methods of using these novel compounds as imaging agents are presented, as are intermediates and methods for making these novel compounds.

21 Claims, 22 Drawing Sheets

OTHER PUBLICATIONS

Meegalla et al, Bioconjugate Chem., 1996, vol. 7, No. 4, pp. 421–429, "Tc–99m Labeled Tropanes as dopamine transporter Imaging Agents.".*

Meegalla et al, J. Am. Chem. Soc., 1995, vol. 117, pp. 11037–11038, "First Example of a 99m–Tc Complex as a dopamine transporter Imaging Agent.".*

* cited by examiner (1.1)
(1.2)
a. R=p-Cl-Ph-
b. R=p-F-Ph-
c. R=p-Br-Ph-
(1.3)
(1.4)
(1.5)
(1.6)
(1.7)
a. R=p-Cl-Ph-
b. R=p-F-Ph-
c. R=p-Br-Ph- (1.8) (1.9) (1.10) (1.11) (1.12) (1.13) (1.14) (1.15) (1.16) (1.17)

(1.7a) (1.7b) OR (1.16a) (1.16b) (1.16c)

1.19a: R=p-Cl-Ph-; Y : CH 2 TRODAT-1
1.19b: R=p-Cl-Ph-; Y : C=O
1.20a: R=p-F-Ph-; Y : CH 2
1.20b: R=p-F-Ph-; Y : C=O
1.20c: R=p-Br-Ph-; Y : CH2

(1.17) (1.21)

(1.16a) (1.22)

TRODAT-1 (1.19a)

PEAK A OR PEAK B

HPLC PROFILE OF RACEMIC MIXTURE BY
PRP-1 COLUMN, $CH_3CN$/BUFFER (pH 7) 80:20
1 mL/min, ret. TIME 14 min.
RADIOCHEM. PURITY > 97%

HPLC PROFILES OF ISOMERS SERARATED BY
AD-COLUMN, HEXANE/EtOH 3:1
1 mL/min COLLECTED IN A RATIO OF A:B=2:3
RCP OF EACH COMPOUND > 99%

FIG.6A
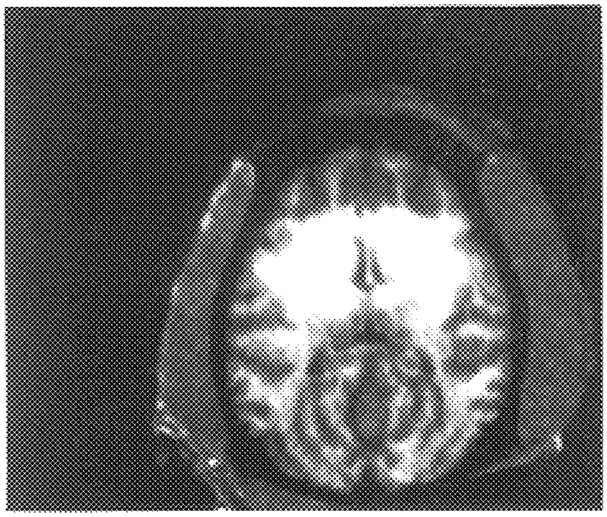
FIG.6B
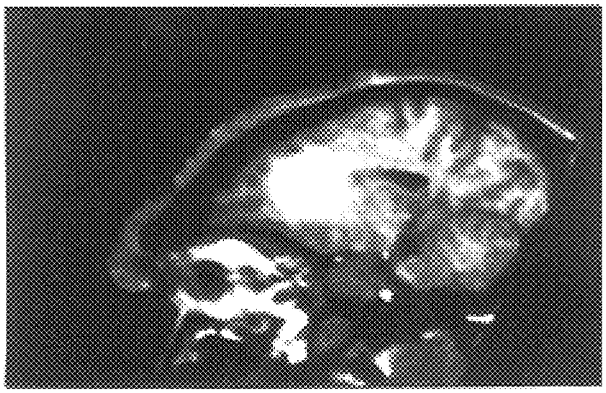
FIG.6C
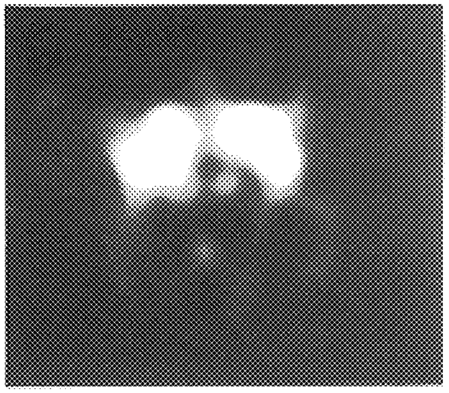
FIG.6D (2.5a) (2.6)

(2.5a) (2.7a)

(2.6a)

RACEMIC MIXTURE

PROPOSED STRUCTURES FOR PEAK A OR PEAK B

HPLC PROFILE OF RACEMIC MIXTURE BY PRP-1 COLUMN, $CH_3CN$/BUFFER (pH 7) 90:10 1 mL/min, ret. TIME 9.8 min. RADIOCHEM. PURITY > 99%

HPLC PROFILES OF ISOMERS SEPERATED BY AD-COLUMN, HEXANE/EtOH 1:1 1 mL/min COLLECTED IN A RATIO OF A : B=1:1 RADIOCHEM. PURITY OF EACH COMPOUND > 99%

| | $R_1$ | $R_2$ |
|---|---|---|
| 3.6 | $CH_3$ | $CH_3$ |
| 3.7 | $CH_3$ | H |
| 3.8 | Et | H |
| 3.9 | i-Bu | H |
| 3.10 |  | H |
| 3.11 |  | H |
| 3.12 |  | H |

| | X |
|---|---|
| 3.13 | F |
| 3.14 | Cl |

| | X | n |
|---|---|---|
| 3.15 | F | 2 |
| 3.16 | Cl | 2 |
| 3.17 | F | 3 |
| 3.18 | Cl | 3 |

| | X | n |
|---|---|---|
| 3.19 | F | 2 |
| 3.20 | Cl | 2 |
| 3.21 | F | 3 |
| 3.22 | Cl | 3 |

| | $R_1$ | $R_2$ |
|---|---|---|
| 3.6 | $CH_3$ | $CH_3$ |
| 3.7 | $CH_3$ | H |
| 3.8 | Et | H |
| 3.9 | i-Bu | H |
| 3.10 |  | H |
| 3.11 |  | H |
| 3.12 |  | H |

| | X | n |
|---|---|---|
| 3.19 | F | 2 |
| 3.20 | Cl | 2 |
| 3.21 | F | 3 |
| 3.22 | Cl | 3 |

| | $R_1$ | $R_2$ | X | n |
|---|---|---|---|---|
| 3.24 | $CH_3$ | H | F | 2 |
| 3.25 | $CH_3$ | H | Cl | 2 |
| 3.26 | $CH_3$ | $CH_3$ | F | 2 |
| 3.27 | $CH_3$ | $CH_3$ | Cl | 2 |
| 3.28 | $CH_3$ | H | F | 3 |
| 3.29 | $CH_3$ | H | Cl | 3 |
| 3.30 | Et | H | Cl | 2 |
| 3.31 | i-Bu | H | Cl | 2 |
| 3.32 |  | H | Cl | 2 |
| 3.33 |  | H | Cl | 2 |
| 3.34 |  | H | Cl | 2 |

DOPAMINE AND SEROTONIN TRANSPORTER LIGANDS AND IMAGING AGENTS

RELATED CASES

This patent application is a continuation-in-part application of U.S. patent application Ser. No. 08/545,327 now abandoned filed on Oct. 19, 1995.

GOVERNMENT SUPPORT

The work reported herein was supported in part by National Institute of Health NS-18509 and NS-24538.

FIELD OF THE INVENTION

This invention relates to novel tropane-based ligands that display selective binding to central nervous system receptors, such as dopamine and serotonin transporters (reuptake sites), and have utility, inter alia, as imaging agents for the central nervous system. Also within the scope of this invention are methods for utilizing these ligands as diagnostic agents. Methods for preparing the novel ligands of the invention and intermediates useful in their preparation are also presented.

BACKGROUND

Neural transmitters are chemicals in the brain that are used to send messages from one brain cell to another. Neurotransmitters bind to special receptor proteins in the membranes of nerve cells, like a lock in a key, triggering a chemical reaction within the cell. Dopamine is an example of a central nervous system (CNS) neurotransmitter.

Dopamine is a catecholamine belonging to a class of biogenic amine neurotransmitters, along with norepinephrine, serotonin, and histamine. The catecholomines (particularly dopamine and serotonin) are involved in the control of movement; mood; attention; and possibly, certain endocrine, cardiovascular, and stress responses. Imbalances in neurotransmitter production have been implicated in a variety of mental and physical disorders, such as Parkinson's disease (PD). It is thus desirable to diagnose and monitor such imbalances and to monitor the effectiveness of drugs and substances that affect brain chemistry.

New and powerful imaging methods that enable one to assess the living brain in vivo and thereby monitor brain chemistry and the effectiveness of drugs and substances that affect brain chemistry have been developed. Methods such as positron emission tomography (PET) and single photon emission computed tomography (SPECT) involve administering to a patient a radioactive tracer substance comprising a ligand that binds to the presynaptic or postsynaptic neuroreceptors in the patient's brain. Emissions (primarily gamma rays are emitted from the positrons or photons from the radioactive tracer) are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control to determine the degree of drug response. Further treatment of the patient with drugs is based on the comparisons made. For these methods to be useful, however, a ligand that has a high specificity and affinity for the desired receptor is required.

It is believed that certain radioactive ligands may be selective for dopamine transporters and are thus potentially useful in evaluating changes in dopamine function in vivo and in vitro, especially for patients with Parkinson's disease (PD), which is characterized by a selective loss of dopamine neurons in the basal ganglia and substantia nigra. Recently, a large number of dopamine transporter imaging agents based on cocaine or its closely related congeners, tropane derivatives, have been reported. (Carroll, F. I., et al, *Med. Res. Rev*. 1995, 15, 419–444; Carroll, F. I., et al., *J. Med. Chem*. 1994, 37, 2865–2873; Carroll, F. I., et al., *J. Med. Chem*. 1995, 38, 379–388). The regional brain distribution of cocaine is largely concentrated in the basal ganglia, where the dopamine neurons are located. [$^{11}$C]-N-methyl labeled cocaine (Yu, D.-W., et al., *J. Med. Chem*. 1992, 35, 2178–2183; Fowler, J. S., et al., *Synapse* 1992, 12, 220–227) is a very useful PET (positron emission computed tomography) ligand for studying the pharmacology and drug effects of cocaine itself; however, additional modifications on the cocaine molecule have led to development of positron emission tomography (PET) imaging agent, CFT (WIN35, 428) (Clarke, R. L. et al. *J. Med. Chem*. 1973, 16, 1260–1267; Clarke, R. L. et al. *J. Med. Chem*. 1978, 21, 1235–1242; Frost, J. J., et al., *Ann. Neurol*. 1993, 34, 423–431; Wong, D. F., et al., *Synapse* 1993, 15, 130–142), and single photon emission computed tomography (SPECT) imaging agents β-CIT (Innis, R. B., et al., *Proc. Natl. Acad. Sci. U.S.A*. 1993, 90, 11965–11969; Seibyl, J. P., et al., *J. Nucl. Med*. 1996, 37, 222–228; Kuikka, J. T., et al., *Eur. J. Nucl. Med*. 1995, 22, 682–686; Neumeyer, J. L., et al., *J. Med. Chem*. 1994, 37, 1558–1561.), IPT (Goodman, M. M. et al. *J. Med. Chem*. 1994, 37, 1535–1542; Mozley, P. D., et al., *J. Nucl. Med*. 1996, 37, 151–159), and other related derivatives that display much higher binding affinity and selectivity to dopamine reuptake sites. Both of the agents for PET and SPECT imaging displayed excellent specific uptake in the striatum (basal ganglia) area and are more suitable than GBR12,935 in imaging dopamine reuptake sites (dopamine transporters). (Kilbourn, M. R., *Life Sci*. 1988, 42, 1347–1353). The dopamine reuptake site ligands are useful in evaluating changes in dopamine reuptake sites in vivo and in vitro, especially for patients with PD. Recent publications describing the use of [$^{11}$C]-CFT (WIN35,428) (Frost, J. J., et al., *Ann. Neurol*. 1993, 34, 423–431) and [$^{123}$I]-β-CIT (Innis, R. B., et al., *Proc. Natl. Acad. Sci. U.S.A*. 1993, 90, 11965–11969; Innis, R. B., *Eur. J. Nucl. Med*. 1994, 21, 1–5) suggest a strong correlation between the decrease in localization of dopamine transporters in the anterior putamen area and PD symptoms.

Currently, PET and SPECT imaging studies of dopamine transporters are under investigation. Recent publications using [$^{11}$C]-CFT and [$^{123}$I]-β-CIT suggest a strong correlation between the decrease in localization in the anterior putamen area and PD symptoms. See Innis, R. B. et al. *Proc. Natl. Acad. Sci. U.S.A*. 1993, 90, 11965–11969; Innis, R. B. *Eur. J. Nucl. Med*. 1994, 21, 1–5; Frost, J. J. et al. *Ann. Neurol*. 1993, 34, 423–431, the disclosures of which are herein incorporated by reference in their entirety.

Central nervous system (CNS) receptor function has also been successfully evaluated in vivo using $C^{11}$ ($T_{1/2}$=20 minutes, β+) or $F^{18}$ ($T_{1/2}$=120 minutes, β+) labeled agents for positron emission tomography (PET) imaging and $^{123}$I ($T_{1/2}$=13 hours, 159 KeV) labeled agents for single photon emission computed tomography (SPECT) imaging. See Eckelman, W. C. *Nucl. Med. Biol*. 1992, 18, iii–v; Fowler, J. S. et al. *Ann. Rep. Med. Chem*. 1989, 24, 277–286; Fowler, J. S. et al. *Ann. Rep. Med. Chem*. 1990, 25, 261–268, the disclosures of which are herein incorporated by reference in their entirety.

A ligand that is being widely investigated as an agent for diagnosing and treating PD patients is [$^{123}$I]-CIT. However, one of the drawbacks of [$^{123}$I]-β-CIT is the length of time (>18 hours) required for reaching optimal uptake ratio in the target area (semi-equilibrium state) (the basal ganglia (BG)) versus the nontarget area (the frontal cortex (CTX)). Because of the need for agents with faster equilibrium times, new ligands such as [$^{123}$I]-IPT (N-(3-iodopropen-2-yl)-2β-carbomethoxy-3β-(4-chlorophenyl)tropane) and [$^{123}$I]-β-CIT-FP are under investigation, both of which reach equilibrium in less than one hour. See Kung, M.-P. et al. *Synapse* 1995, 20, 316–324; Malison, R. T. et al. *J. Nucl. Med.* 1995, in Press; Mozley, P. D. et al. *J. Med. Chem.* 1994, 37, 1558–1561, the disclosures of which are herein incorporated by reference in their entirety.

Despite the success in developing such new techniques using PET and SPECT for imaging CNS receptors, their use in routine procedures is hampered by the cost ([$^{123}$I] costs about $30/mCi) and the limited supply of the three isotopes mentioned above, $^{123}$I, $^{11}$C, and $^{18}$F, all of which are produced by cyclotron.

A radionuclide that is widely used in diagnostic nuclear medicine is technetium [$^{99m}$Tc] ($T_{1/2}$=6 hours, 140 KeV). It is well established that when Tc-99m pertechnetate ($TcO_4$—), the most commonly available starting material, is reduced in the presence of a reducing agent, such as stannous chloride, and a "soft" chelating ligand, including $N_2S_2$ and $NS_3$, a $[Tc^VO]^{3+}N_2S_2$ or $[Tc^VO]^{3+}NS_3$ center core is formed. Technetium [$^{99m}$Tc] is readily produced by a [$^{99m}$Tc]/Mo-99 generator, and its medium gamma-ray energy emission (140 KeV) is suitable for gamma camera detection with a far less cost ($1/mCi). In the past ten years, significant progress has been made in defining technetium chemistry using the chemical level of [$^{99}$Tc] ($T_{1/2}$=2.1×10$^5$ yr), and non-radioactive rhenium as a surrogate substitute, that will potentially benefit millions of patients who receive [$^{99m}$Tc] agents for routine nuclear medicine diagnosis. Over 85% of the routine nuclear medicine procedures currently performed use radiopharmaceutical methodologies based on [$^{99m}$Tc]. In addition, comparable rhenium complexes labeled with [$^{186}$Re] ($T_{1/2}$=90 hours) or [$^{188}$Re] ($T_{1/2}$=17 hours) may also be potentially useful for in vivo imaging of dopamine transporters.

The potential of developing [$^{99m}$Tc] labeled agents for CNS receptor imaging is well recognized. Several recent reports demonstrate that it is possible to incorporate [TcvO] $^3$+$N_2S_2$ (bisaminoethanethiol, BAT) into potential receptor selective imaging agents for muscarinic receptors, vesamicol sites, and steroid hormone receptors. See Del Rosario, R. B. et al. *Nucl. Med. Biol.* 1994, 21, 197–203; Chi, D. Y. et al. *J. Med. Chem.* 1994, 37, 928–935; DiZio, J. P. et al. *Bioconj. Chem.* 1991, 2, 353–366; DiZio, J. P. et al. *J. Nucl. Med.* 1992, 33, 558–569; O'Neil, J. P. et al. *Inorg. Chem.* 1994, 33, 319–323; O'Neil, J. P. et al. *Bioconj. Chem.* 1994, 5, 182–193; Jurisson, S. et al. *Chem. Rev.* 1993, 93, 1137–1156; Jurisson, S. S. et al. *Nucl. Med. Biol.* 1995, 22, 269–281; Jurisson, S. et al. *Chem. Rev.* 1993, 93, 1137–1156; Steigman, J. et al. National Academy Press: Washington, D.C. 1992; Lever, S. Z. et al. *Nucl. Med. Biol.* 1994, 21, 157–164, Chi, D. Y. et al. *Am. Chem. Soc.* 1993, 115, 7045–7046, the disclosures of which are herein incorporated by reference in their entirety. However, these [$^{99m}$Tc] imaging agents have demonstrated limited success in in vivo studies, this is believed to be attributable to the low initial brain uptake and poor selective binding to the receptor after attaching the molecules with [$^{99m}$Tc].

Recently, a series of neutral and lipophilic conjugated complexes, containing N-alkylthiolatotropane, aminobisethylthiolato and a [$^{99m}$Tc]$TcO^{3+}$ center core, were prepared and evaluated as CNS dopamine transporter imaging agents in rats (Meegalla, S. K., et al., *J. Am. Chem. Soc.* 1995, 117, 11037–11038). One of the compounds, [$^{99m}$Tc] technetium, [methyl 3-(4-chlorophenyl)-8-(2-mercaptoethyl)-8-azabicyclo [3.2.1]octane-2-carboxylato-S][[2,2'-(methylimino) bis[ethanethiolato]](2-)-N,S,S']oxo, displayed low initial uptake in rat brain (0.1% at 2 minutes post intravenous injection), but the striatal/cerebellar (ST/CB) ratio reached 3.50 at 60 minutes after an intravenous injection. The Rhenium complexes were also discussed. These neutral [$^{99m}$Tc] labeled three plus one complexes designed for brain imaging, as well as mixed-ligand, aminothiol plus aminothiol complexes (two plus two complexes) designed as [$^{99m}$Tc] steroid analogs are quite stable in vivo and in vitro. However, since these agents are not designed to cross the blood-brain barrier, they are inferior for imaging CNS receptors, such as dopamine and serotonin.

Technepine compounds containing technetium and rhenium have been investigated as potential dopamine transporter agents. Madras, B. K., et al., *Synapse* 1996, 22, 239–246. These compounds showed poor biodistribution, which is believed to be a result of the amide moiety present on the $N_2S_2$ ligand.

Despite its attractive physical properties, technetium is a difficult element for designing suitable SPECT ligands. Technetium is a transition metal and requires a complexing agent to stabilize it at different valence states. Steigman, 1992, supra. Valance states can vary from plus 7 (as pertechnetate) to zero (0), depending on the reaction conditions and chelating agents used during preparation. After complexation, the molecules invariably become big and bulky, which is the limiting factor in designing a molecule targeted to a specific biological process(es). Additional requirements for Tc-99m labeled complexes as CNS receptor imaging agents are: i) small (molecular weight <750), with good lipophilicity (partition coefficient ~50–1,000); ii) high binding affinity (Kd <10 nM) and high selectivity; iii) minimum brain uptake in rats should be 0.5% dose/organ at 2 minutes post intravenous injection.

The [$^{99m}$Tc] brain imaging agents that have been developed thus far have been aimed at measuring perfusion or its changes due to a particular disease state, and not as diagnostics directed to evaluating neuronal functions, such as the biochemistry of dopamine or serotonin receptors. See Mastrostamatis, S. G. et al., *J. Med. Chem.* 1994, 37, 3212–3218; Spies, H. et al., *Technetium and Rhenium in Chemistry and Nuclear Medicine*, 1995, 4, 243–246; S. G. Editoriali, Ed.: Padova, Italy 1995, 4, 243–246; Spies, H. et al. *Angew. Chem. Int. Ed. Engl.* 1994, 33, 1354–1356; Chi, D. Y. et al. *J. Amer. Chem. Soc.* 1993, 115, 7045–7046; Chi, D. Y. et al. *J. Med. Chem.* 1994, 37, 928–935, the disclosures of which are herein incorporated by reference in their entirety.

Thus, there remains a need for new imaging agents, such as CNS receptor-based imaging agents, for evaluating neuronal functions that do not present the problems associated with prior agents, as discussed above. These agents should have good selectivity, affinity, and specific activity for the target. Several additional factors are also of importance such as radiochemistry (preparation time for short-lived labeled agents), suitable modeling for kinetics of receptor uptake and retention, and metabolism. The imaging agents should also be economical and readily available.

The present invention addresses these, as well as other needs, by providing novel tropane-based technetium- or rhenium- labeled imaging agents useful, inter alia, for imaging the CNS, in particular dopamine and serotonin receptors, to diagnose CNS abnormalities. It is also expected that the novel compounds of the invention possess pharmacological activity. It is believed that the compounds of the invention are the first imaging agents of their kind displaying specific regional uptake directly proportional to dopamine neuronal distribution in the brain.

SUMMARY OF THE INVENTION

This invention presents, inter alia, a novel class of technetium- or rhenium-labeled dopamine or serotonin transporters imaging agents based on a tropane core. The compounds of the invention transfer through the blood brain barrier, which makes them good candidates for diagnostic and therapeutic agents for the central nervous system.

In one aspect of this invention, the compounds of the invention have the following general formula (I):

I

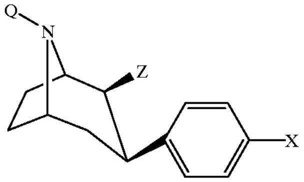

wherein X is selected from the group consisting of H, $C_1$-$C_4$ alkyl, F, Cl, Br, and I; Q is selected from the group consisting of H, $C_1$-$C_5$ alkyl, $A_1$, $A_2$, $A_3$, $A_4$, $A_5$, $A_6$, $A_7$, and $A_8$; Z is selected from the group consisting of R, $CONRR_1$, $COR_1$, $CO_2R_1$, $CO_2R_2$, $CO_2A_1$, $CO_2A_2$, $CO_2A_3$, $CO_2A_4$, $CO_2A_5$, $CO_2A_6$, $CO_2A_7$, $CO_2A_8$, $COA_1$, $COA_2$, $COA_3$, $COA_4$, $COA_5$, $COA_6$, $COA_7$, $COA_8$, $CH_2OA_1$, $CH_2OA_2$, $CH_2OA_3$, $CH_2OA_4$, $CH_2OA_5$, $CH_2OA_6$, $CH_2OA_7$, $CH_2OA_8$, $CH_2NHA_1$, $CH_2NHA_2$, $CH_2NHA_3$, $CH_2NHA_4$, $CH_2NHA_5$, $CH_2NHA_6$, $CH_2NHA_7$, $CH_2NHA_8$, $A_1$, $A_2$, $A_3$, $A_4$, $A_5$, $A_6$, $A_7$, and $A_8$; Y is $—(CH_2)_n$; R is H, $C_1$–$C_5$ alkyl; $R_1$ is H, $C_1$–$C_5$ alkyl; $R_2$ is a heterocyclic amine;

$A_1$ is

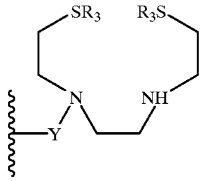

$A_2$ is

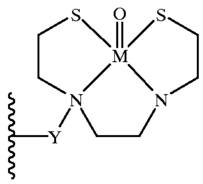

$A_3$ is

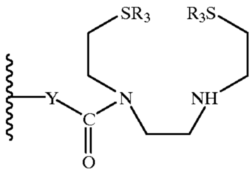

-continued $A_4$ is

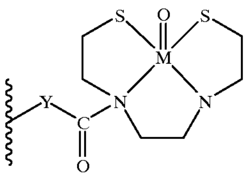

$A_5$ is

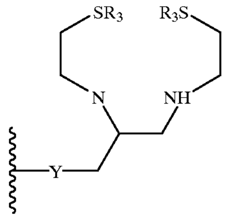

$A_6$ is

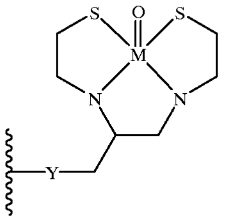

$A_7$ is

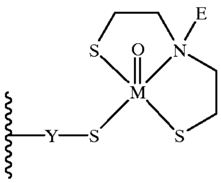

$A_8$

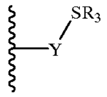

E is $C_1$–$C_2$ alkyl; n is 0, 1, 2, 3, 4, 5; M is selected from the group consisting of Tc and Re; $R_3$ is selected from the group consisting of H, $CR_4$, substituted or unsubstituted $C_1$–$C_5$ alkoxy, substituted or unsubstituted $C_6$–$C_{24}$ aryl, and substituted or unsubstituted phenylalkoxy; and $R_4$ is selected from the group consisting of H and $C_1$–$C_5$ alkyl, optionally substituted with a substituted or unsubstituted phenyl group; provided that, one of Q and Z, and only one of Q and Z, includes a moiety selected from the group consisting of $A_1$, $A_2$, $A_3$, $A_4$, $A_5$, $A_6$, $A_7$, and $A_8$.

The compounds of the invention include compounds that comprise an $N_2S_2$ ligand (bis-aminoethanethiol) in which the ligand complexes with either the technetium or rhenium, or "three plus one complexes" ($NS_3$) where a tropane thiolate and an aminobisethanethiolate ligand are involved in complexation. In one series of the $N_2S_2$ complexes, the $N_2S_2$ ligand is attached to the 2β position of the tropane core, at the Z position of Formula I. In another series of the $N_2S_2$ complexes, the $N_2S_2$ ligand is attached to the bridge head nitrogen of the tropane core. The "three plus one complexes" may have the ligand attached to either the 2β position of the tropane core or the bridge head nitrogen of the tropane core.

This invention further relates to compounds that are useful, inter alia, as intermediates for preparing the compounds of the invention. For example, compounds having the following general Formula II, are useful, inter alia, as intermediates for preparing certain three plus one complexes of the invention. A compound of Formula II has the following general formula:

II

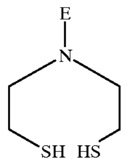

wherein E is $C_1$–$C_2$ allyl.

A compound of Formula II can be used in combination with a compound of Formula I wherein X is $C_1$–$C_4$ alkyl, F, Cl, Br, or I; Q is $A_8$, wherein Y is $-(CH_2)_n-$ and n is 0, 1, 2, 3, 4, or 5; and Z is $CO_2R_1$ or $CO_2R_2$, wherein $R_1$ is $C_1$–$C_5$ alkyl and $R_2$ is a heterocyclic amine.

The compounds of Formula I, where $A_n$ is $A_8$, and the compounds of Formula II are useful, inter alia, as intermediates for preparing certain three plus one complexes of the invention, and further useful as kit components. Kits comprising these compounds and kits comprising other Formula I compounds are also within the scope of this invention.

In other aspects of the invention, methods of utilizing the novel ligands of the invention in diagnostic imaging techniques are presented.

Test results indicate that the novel ligands of the invention are highly selective for CNS receptors, particularly dopamine receptors, which make these compounds useful, when appropriately labelled, as imaging agents for the evaluation of such receptors. The compounds of the invention should also have pharmacological activity associated with such CNS receptors as a result of their high selectivity.

BRIEF DESCRIPTION OF THE DRAWINGS

FIGS. 6A–6D depict a transaxial, coronal and sagital SPECT images (1.34 mm thick) of monkey brain at 60–90 post-intravenous injection of 9 mCi of [99mTc]TRODAT-1 (1.19a). SPECT images were acquired by a Picker T3000 scanner. The SPECT images were co-registered with the same sections of MRI of the same baboon. A high accumulation of [99mTc]TRODAT-1 (1.19a) was observed in caudate and putamen, areas of the brain where dopamine transporters are concentrated.

DETAILED DESCRIPTION OF THE INVENTION

Figure 1:
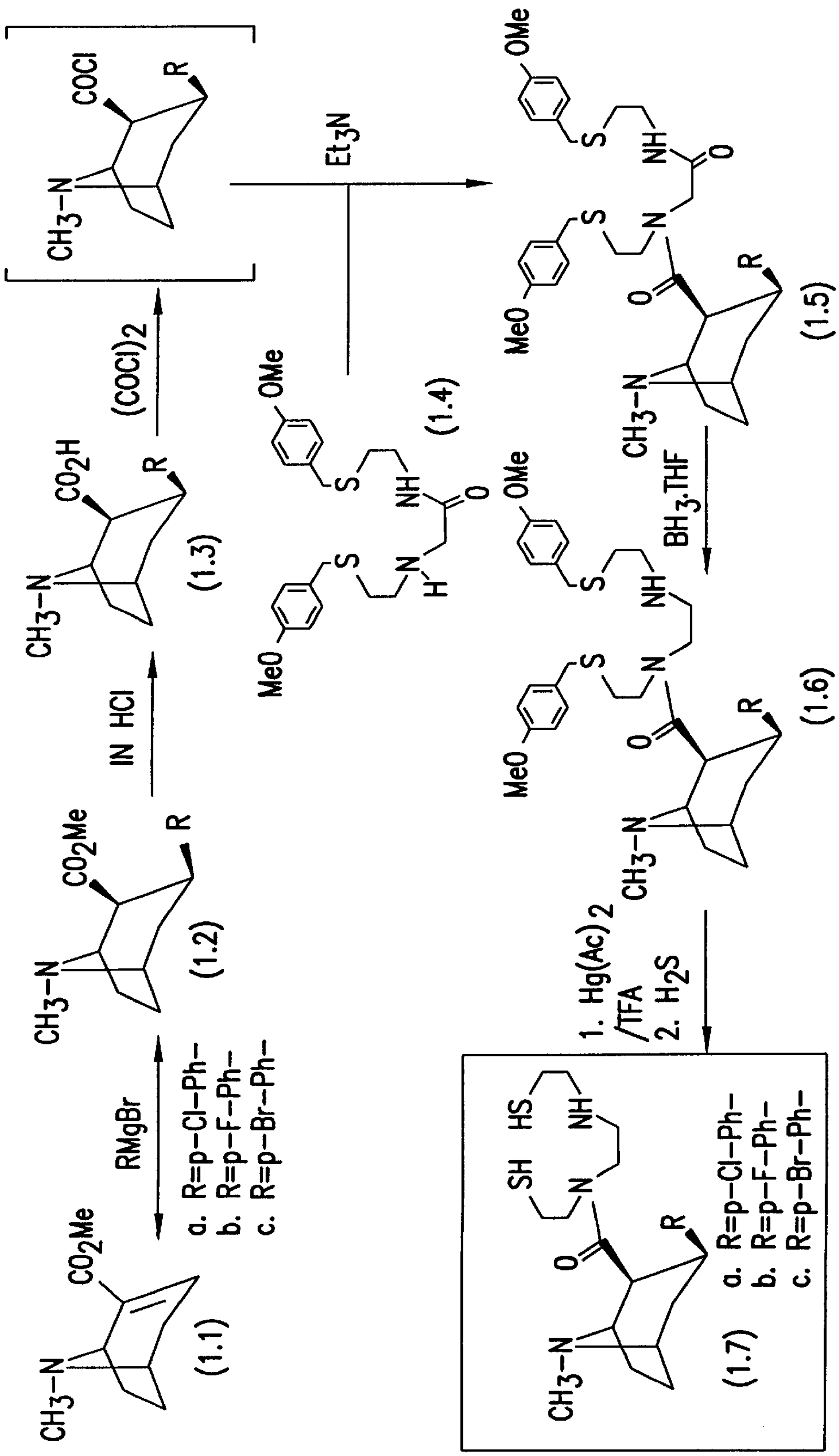
FIG. 1 depicts a general reaction scheme that may be used for synthesizing compounds of Formula I comprising a two plus one complex and where the $N_2S_2$ ligand is attached to the 2β position of the tropane ring via an amide linkage.

The term "ligand," as used herein, refers to compounds chelating with a central atom in a complex compound, and may be used generally to refer to the compounds of the invention. It is contemplated that certain of the compounds of the invention may be chiral or have chiral centers and form R and S isomers (enantiomers), which may be resolved, for example, using a chiral HPLC column. The racemic mixtures as well as the resolved isomers of the ligands are within the scope of this invention.

A "complex compound," as used herein, refers to any group of chemical compounds in which part of the molecular bonding is of the coordination type. In the context of this invention, "coordination compound" refers to compounds having a central atom or ion and a group of ions or molecules surrounding it.

In the context of this invention, "tridentate ligand" refers to a chelating agent having three groups capable of attachment to a metal ion. As used herein, the terminology "chelating agent" refers to organic compounds in which atoms form more than one coordinate bond with metals in solvent.

As used herein, the term "alkyl" refers to radicals that are formed from the loss of a hydrogen from an alkane ($C_nH_{2n+2}$). The alkyl compounds may be straight or branched chain compounds, cyclic or acyclic, and further substituted with hetero atoms (i.e., O, S, N). Also included within this definition are structural isomers (i.e., chain isomers, position isomers, and functional isomers) and stereoisomers (i.e., enantiomers and diasteriomers).

In the context of this invention, the term "aliphatic" refers to any carbon-hydrogen containing compounds having either saturated or unsaturated bonds (alkanes, alkenes, alkynes). Such compounds may be cyclic or acyclic, straight or branched chains, and may further be substituted with hetero atoms (i.e., O, S, N). The term "aromatic," as used herein, refers to any compound that contains at least one benzene ring. The term "aryl," as used herein refers to a compound having at least one benzene radical or benzene ring, and may be substituted with other aliphatic compounds.

The terminology, "heterocyclic amines," refers to aliphatic compounds having a ring structure that incorporates other atoms in addition to carbon atoms. Heterocyclic amines include, without limitation, pyrrole and its derivatives, imidazole and its derivatives, pyridine and its derivatives, pyrimidine and its derivatives, qunioline and its derivatives, piperidine and its derivatives, pyrrolidone and its derivatives, purine and its derivatives, pyrrolidine and its derivatives, and morpholine and its derivatives. Derivatives refers to compounds having the core heterocyclic structure (e.g., pyrrole) substituted with one or more of an aliphatic moiety, aromatic moiety, alkoxy moiety, phenoxy moiety, amine moiety, nitro moiety, nitrile moiety, halogens, or hetero atoms.

As used herein, the term "phenoxy" is used in its conventional sense and refers to, generally, phenyl radicals attached to a molecule through an oxygen. It is contemplated that the phenoxy compounds of the invention may be further substituted. Also included within this definition are structural isomers (e.g., chain isomers, position isomers, and functional isomers) and stereoisomers (e.g., enantiomers and diasteriomers).

The term "alkoxy," as used herein, is used in its conventional sense and refers to, generally, alkyl radicals attached to a molecule through an oxygen. Alkyl radicals are generally derived from an aliphatic hydrocarbon by removal of one hydrogen atom. It is contemplated that the alkoxy compounds of the invention may be further substituted with, for example, other aliphatic compounds. Also included within this definition are structural isomers (i.e., chain isomers, position isomers, and functional isomers) and stereoisomers (i.e., enantiomers and diasteriomers).

The term "substituted," as used herein refers to single or multiple substitutions of a molecule with a moiety or moieties distinct from the core molecule. Substituents include, without limitation, halogens, hetero atoms, nitro moieties, amine moieties, nitrile moieties, hydroxy moieties, alkoxy moieties, phenoxy moieties, other aliphatic or aromatic moieties. Substituted compounds may be referred to as derivatives of the core structure.

As used herein, the terminology "radionuclide-containing" compound refers to any compound that contains at least one atom of a compound capable of being used in radiopharmaceutical techniques, such as technetium or rhenium. As used herein, "technetium-containing compound" refers to any compound that contains at least one atom of technetium (Tc). In the context of this invention, the term "rhenium-containing compound" refers to compounds having at least one atom of rhenium (Re).

The terminology "protecting group," as used herein, is used in its conventional sense and refers to compounds that are used for blocking reactive sites on a multifunctional molecule to prevent such reactive sites from taking part in a chemical reaction.

In one series of compounds the $N_2S_2$ ligand is in the 2β position of the tropane core. These compounds may be synthesized by the general reaction schemes shown in FIGS. 1–3. For example, a ligand, such as 1.16a, 1.16b or 1.17, is dissolved in ethanol and hydrochloric acid. To this is added hydrochloric acid and a reducing agents, such as Sn-glucoheptonate (containing 136 micrograms $SnCl_2$ and 200 micrograms Na-glucoheptonate, pH 6.67) and 50 microliters EDTA solution. [$^{99m}$Tc]Pertechnetate in saline is then added to the reaction mixture, which is then heated for about 30 minutes at 100° C. After cooling to room temperature, the reaction mixture is neutralized with a saturated sodium bicarbonate or phosphate buffer solution. It is possible that tropane derivatives containing a bis-aminoethanethiol group will form stereoisomers.

Other methods for preparing these kinds of compounds are depicted in FIGS. 21–24, but any such methods known to those skilled in the art may be used without departing from the spirit of the invention.

Figure 8:
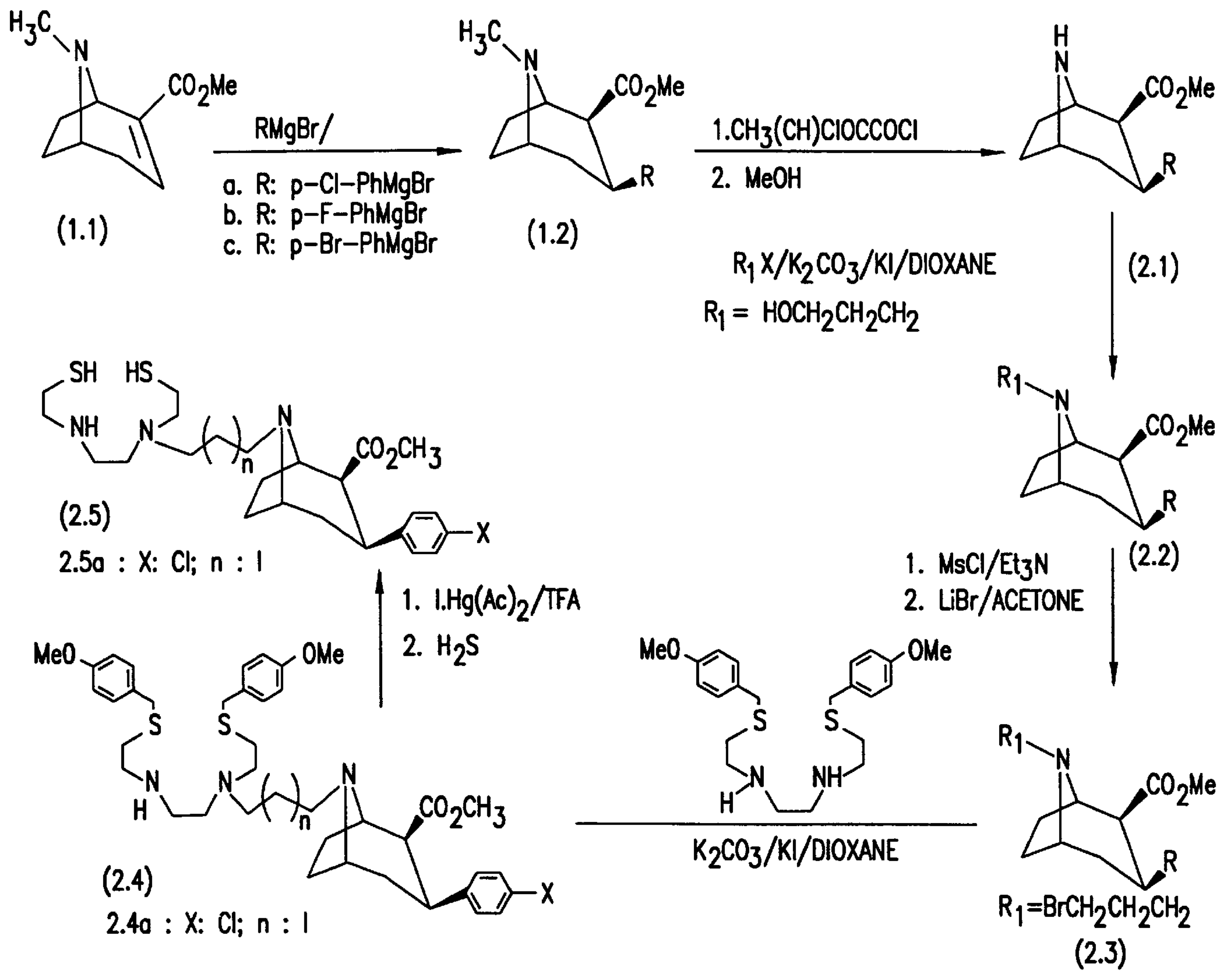
FIG. 8 depicts a general reaction scheme that may be used for synthesizing two plus one complexes where the $N_2S_2$ ligand is connected to the bridge head nitrogen of the tropane core.
Figure 9:
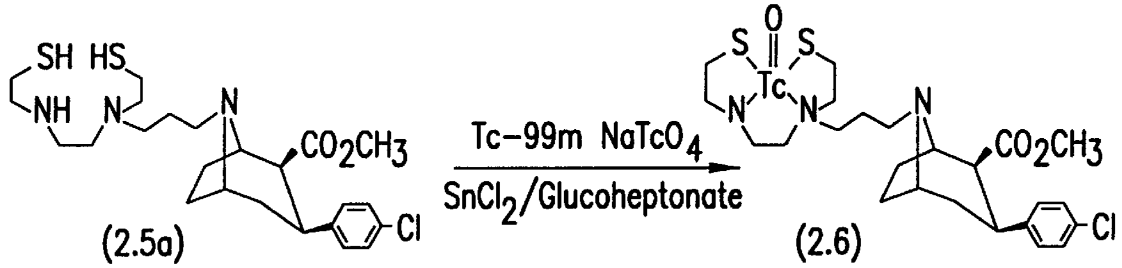
FIG. 9 depicts a general reaction scheme that may be used for radiolabelling an $N_2S_2$ ligand.

Another series of the two plus one complexes has the $N_2S_2$ ligand attached to the bridge head nitrogen of the tropane core. These compounds may be prepared according to the general reaction schemes depicted in FIGS. 8–10. Radiolabeling was achieved by a method similar to that disclosed above in connection with the compounds having the $N_2S_2$ ligand in the 2β-position of the tropane core. The tropane derivatives (2.6a) containing a bis-aminoethanethiol group are believed to form stereoisomers. (Table 2.1 a, b, c).

Figure 19:
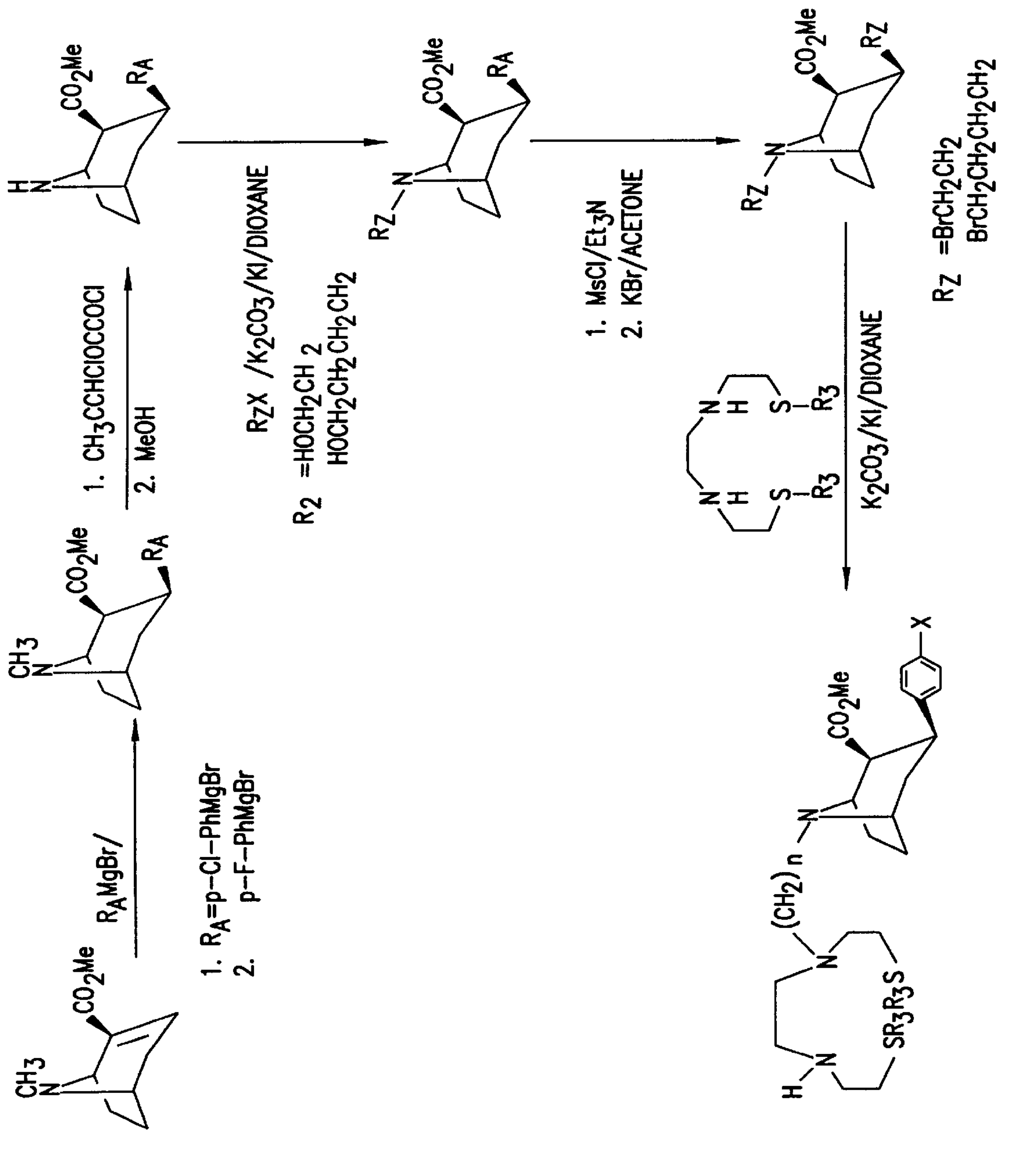
FIG. 19 depicts a reaction scheme where the Z moiety of Formula I is an ester moiety.
Figure 20:
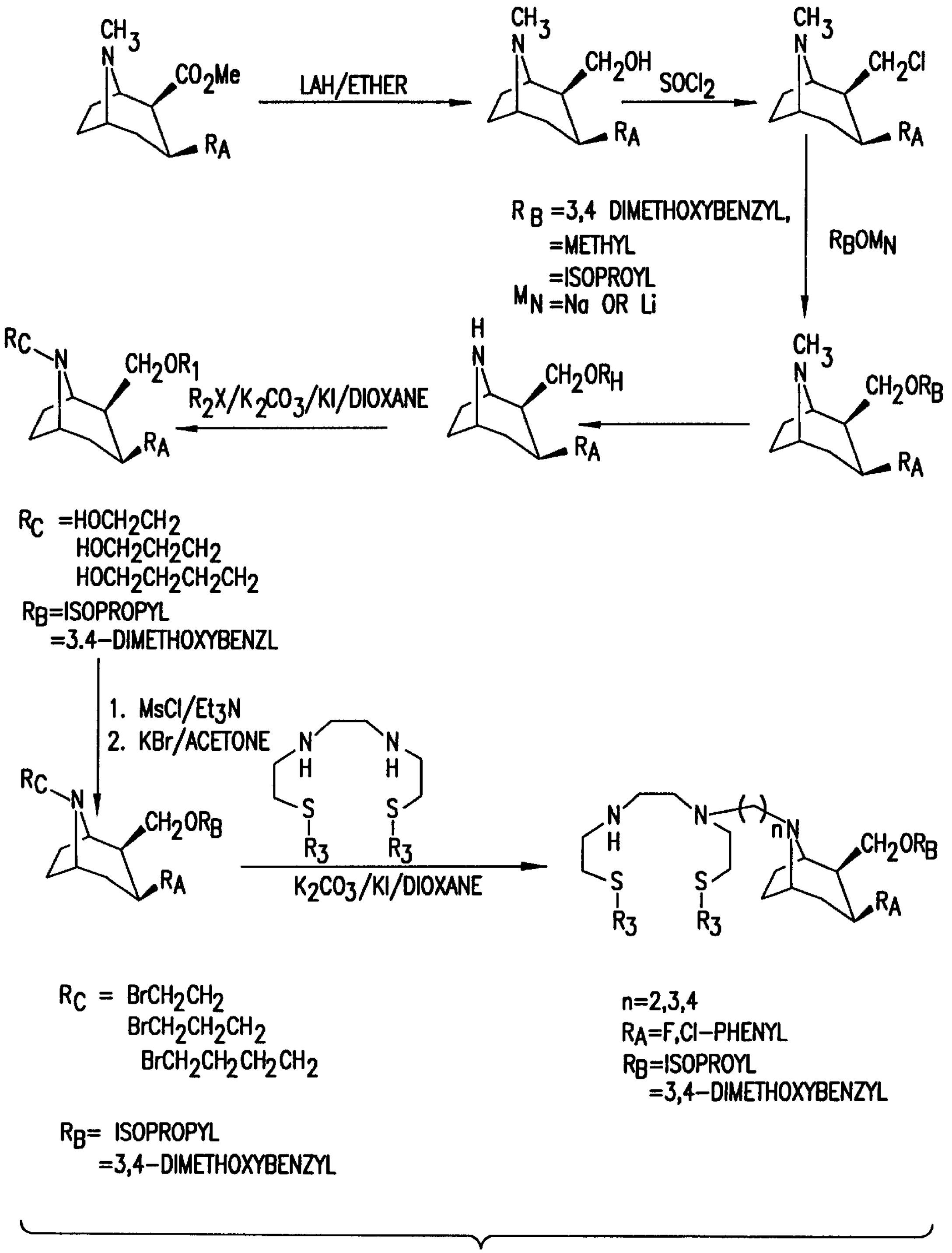
FIG. 20 depicts a reaction scheme where the Z moiety of Formula I is an ether moiety.
Figure 25:
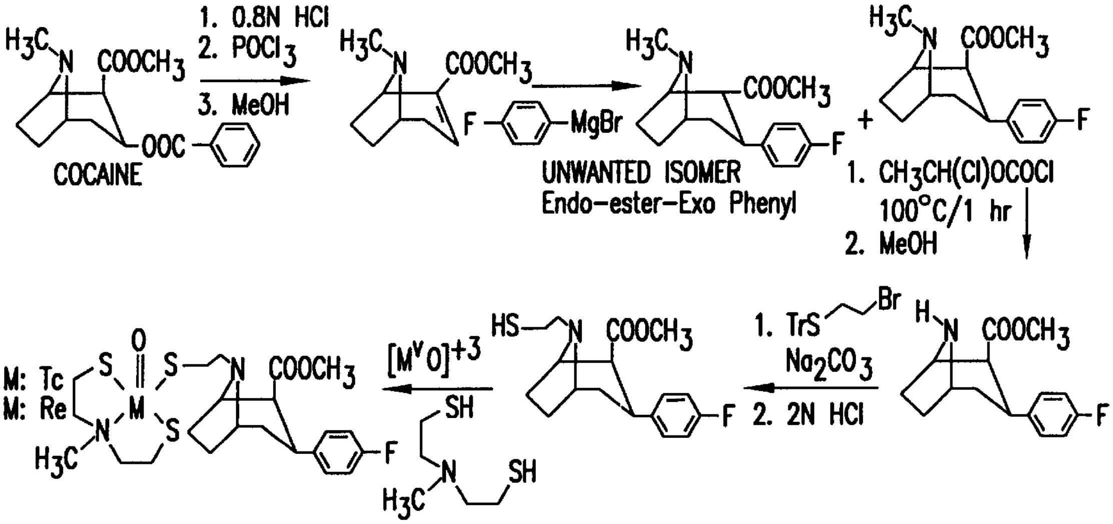
FIG. 25 depicts a reaction scheme for the synthesis of a compound of Formula I using cocaine as a starting material.

Other methods for preparing these kinds of compounds are depicted in FIGS. 19, 20, and 25, but any such methods known to those skilled in the art may be used without departing from the spirit of the invention.

The three plus one complexes ($NS_3$) (those containing, for example, an $A_7$ moiety) may generally be made from two key intermediates—a tridentate ligand aminodithiol (Formula II) and a monothiol ligand (Formula I, where Z is $A_8$), which is particularly applicable when the $A_n$ moiety is in the Q position of Formula I. These intermediates may be prepared by using methods analogous to those in the reaction schemes set forth in FIGS. 12 and 13. The monothiol intermediate compound can be prepared according to the reaction scheme of FIG. 13 or reactions analogous thereto.

Generally, a demethylated tropane derivative is prepared from cocaine in 4 steps, as previously reported. See Meltzer, P. C. et al. *J. Med. Chem.* 1993, 36, 855–862, the disclosure of which is herein incorporated by reference in its entirely. N-alkylation of the tropane derivative is achieved by reacting it with a triphenylmethyl thioether (S-trityl) protected 2-bromoethanethiol and 3-bromopropanethiol. Dhar, T. G. M. et al. *J. Med. Chem.* 1994, 37, 2334–2342. The protecting group (trityl) may then be cleaved by acid hydrolysis or with heavy metal ions to yield the monothiol ligand of Formula II. See Ohmomo, Y. et al. *J. Med. Chem.* 1992, 35, 157–162; Kolb, U. et al. *Inorg. Chem.* 1994, 33, 4522–4530; Dhar, 1994, supra, the disclosures of which are herein incorporated by reference in their entirety. Any protecting groups known to those skilled in the art may be used without departing from the spirit of the invention.

For example, the particular tropane derivatives of formulas 3.19–3.22 may be prepared as follows: a halogenated nortropane derivative is refluxed with a triphenylalkyl mercapto (trityl) compound to form a protected mercapto halogenated nortropane intermediate. The tritylated nortropane derivative is then dissolved in a suitable solvent system, such as trifluoromethyl carboxylic acid and anisole, followed by the addition of a mercury oxide, such as $Hg(OAc)_2$, to cleave the protecting group. The resultant mixture is stirred at 0° C. for 30 minutes. The reaction mixture is then concentrated in vacuo to obtain a brownish red oil, which is then dried under high vacuum for 1 hour. Anhydrous ether is then added to the above oil and the mixture is then sonicated for 15 minutes, followed by magnetic stirring for an additional 30 minutes. This results in the formation of a colorless precipitate, which is then collected by suction filtration. The collected precipitate is then dried under a high vacuum for 15 minutes and then redissolved in ethanol. Hydrogen sulfide gas is then bubbled throughout the ethanol solution for 15 minutes, forming a black precipitate. The resultant black precipitate is then filtered through a thick pad of celite. The resultant filtrate is then concentrated in vacuo to obtain a colorless oil, which is then dried in a high vacuum for 30 minutes. An aqueous solution of hydrochloric acid and an aqueous solution of ether is then added to the dried oil and the resulting mixture is vigorously stirred for 15 minutes. The mixture is then transferred to a separating funnel where the aqueous layer is separated and basified with concentrated ammonium hydroxide and the resulting colorless product is extracted with methylene chloride (20×2 mL). The methylene chloride layer is then dried with sodium sulfate and concentrated in vacuo to yield the desired tropane derivative. Other tropane derivatives of Formula II may be made by analogous methods that would be known to those skilled in the art.

This invention presents a novel series of compounds based on a tropane core, which compounds comprise $N_2S_2$ ligands and three plus one complexes that comprise an $NS_3$ ligand.

Figure 12:
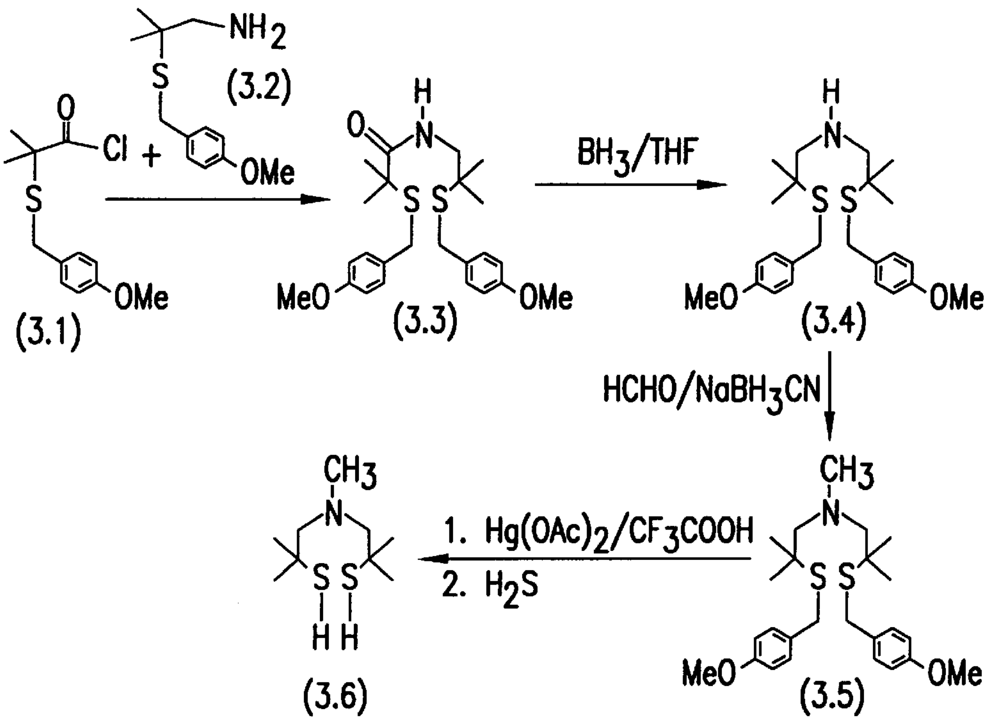
FIG. 12 depicts a reaction scheme that may be used for synthesizing a tridentate ligand that is useful as an intermediate for preparing three plus one complexes of the invention.
Figure 12:
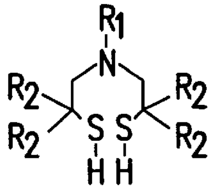
Figure 12:
Figure 12:
Figure 12:
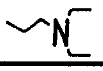

Tridentate ligand aminodithiol intermediates, Formula II, can be synthesized according to the reaction scheme of FIG. 12 or reactions analogous thereto.

In certain preferred embodiments the aminobisethanethiol ligand has gem-dimethyl groups, 3.6, and can be synthesized according to methods known in the art, as shown in FIG. 12. See, e.g., Ohmomo, 1992, supra, the disclosures of which are herein incorporated by reference in their entirety. The aminobisethanethiol ligand without gem-dimethyl groups, 3.7, can be synthesized according to methods known in the art. Kolb, 1994, supra, the disclosures of which are herein incorporated by reference in their entirety. The N-ethyl substituted aminobisethylthiols, 3.8, may be prepared according to the procedure employed for the synthesis of 3.7, using N-ethyl bischloroethyl amine as the starting material. The other N-substituted bisethanethiols, 3.9 to 3.12, may be prepared by bis-alkylation of benzyl-, isobutyl-, morpholinoethyl- and (N,N-bisethylamino)ethylamine with ethylene sulfide, respectively, as disclosed in Corbin, 1984, supra, the disclosures of which are herein incorporated by reference in their entirety.

In certain preferred embodiments the tridentate ligand aminodithiol (Formula II) will be N,N -di[(2-(4'-methoxybenzylthio)-2-methylpropyl)] amine (3.4). This can be prepared by adding a solution of $BH_3$•THF to a solution of N-[(2-(4'-methoxybenzylthio)-2-methylpropyl)]2-(4'-methoxybenzylthio)-2-methyl-propionamide (3.3), and heating the resultant mixture at reflux under nitrogen gas for 12 hours. The reaction mixture is then cooled in an ice bath, and water is carefully added. The resulting solution is then concentrated in vacuo to obtain a viscous oil that is suspended in hydrochloric acid. This mixture is then heated at reflux for 1 hour. The reaction mixture is then cooled in an ice bath and then basified with concentrated ammonium hydroxide. The product (3.4) is then extracted with methylene chloride and purified on silica.

In other preferred embodiments the tridentate ligand aminodithiol (Formula II) is N,N-di[(2-(4'-methoxybenzylthio)-2-methylpropyl)]-methylamine(3.5). This can be prepared by adding $NaBH_3CN$ to a solution of compound 3.4 and methanol in acetonitrile. The resulting mixture is then stirred for 15 minutes and glacial acetic acid is added dropwise until the solution tests neutral. The mixture is then stirred for 45 minutes and the solvents are removed. Potassium hydroxide is then added to the residue, and the resulting mixture is extracted with ether (3×10 mL). The ether extracts are combined and washed with potassium hydroxide and then extracted with hydrochloric acid. The acid extracts are combined and neutralized with solid potassium hydroxide and then re-extracted with ether (3×10 mL). The ether layers are combined and concentrated in vacuo to obtain a viscous oil (3.5), which is purified on silica.

In certain other preferred embodiments, the tridentate ligand aminodithiol (Formula II) is N,N-di[(2-mercapto)-2-methylpropyl)]-methylamine (3.6). This compound can be prepared by mixing the amine compound 3.5 and anisole in trifluoracetic acid and cooling to 0° C. Then $Hg(OAc)_2$ is added and the mixture stirred at 0° C. for 15 minutes and concentrated in vacuo at room temperature. The residue is then dried under a high vacuum for 30 minutes and dry ether is added. The resulting solid is then collected by suction filtration and redissolved in ethanol. Hydrogen sulfide gas is then bubbled through the ethanol solution for 15 minutes and the black precipitate that forms is then filtered through a thick pad of celite. The filtrate is concentrated in vacuo to obtain a colorless oil that is then dried under a high vacuum for 30 minutes. Hydrochloric acid and ether are added to the oil, and the resulting mixture is vigorously stirred for 15 minutes and then transferred to a separating funnel. The aqueous layer is separated and is then basified with concentrated ammonium hydroxide, and the resulting colorless product is then extracted with methylene chloride (20×2 mL). The methylene chloride layer is then dried in sodium sulfate and then concentrated in vacuo to obtain a viscous oil (3.6) which is then stored under a blanket of argon.

Other tridentate ligand aminodithiols of Formula II for use as intermediates in preparing other compounds of Formula I, may be prepared by analogous methods that would be known to those skilled in the art.

The dithiols seem to have only moderate stability and tend to produce a white solid, presumably disulfides, over time. However, the monothiols, 3.15–3.18, seem to have fairly good stability when stored at a low temperature under $N_2$. The X-ray crystallographic structure of the Re-complex 3.23 (FIG. 15), shows that none of the reaction conditions employed in preparation of the monothiols 3.15–3.18 and the Re complex altered the stereochemistry at the C-2 position of tropane ring.

Figure 14:
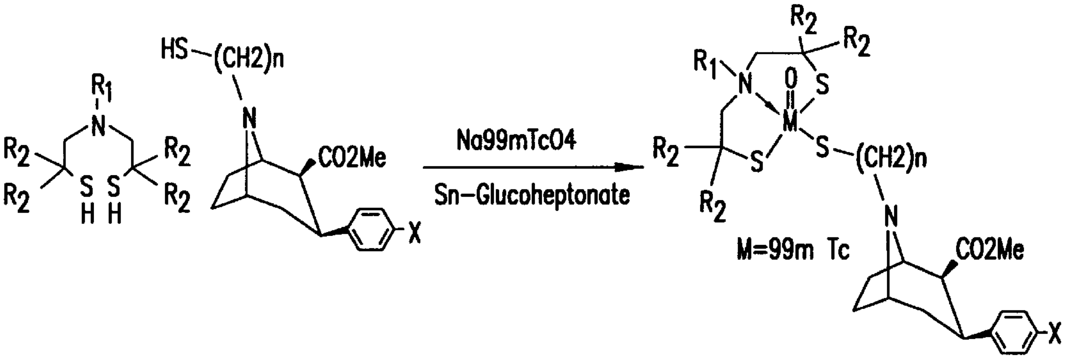
FIG. 14 depicts a reaction scheme for the synthesis of a three plus one complex from Formula II and Formula III intermediates.
Figure 14:
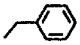
Figure 14:
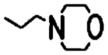
Figure 14:
Figure 14:
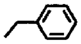
Figure 14:
Figure 14:
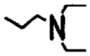

The compounds of Formula I comprising a three plus one complex may be synthesized by using the monothiol intermediate and tridentate aminodithiol intermediate (Formula II) in methods analogous to those illustrated in the general reaction scheme of FIG. 14.

Figure 18:
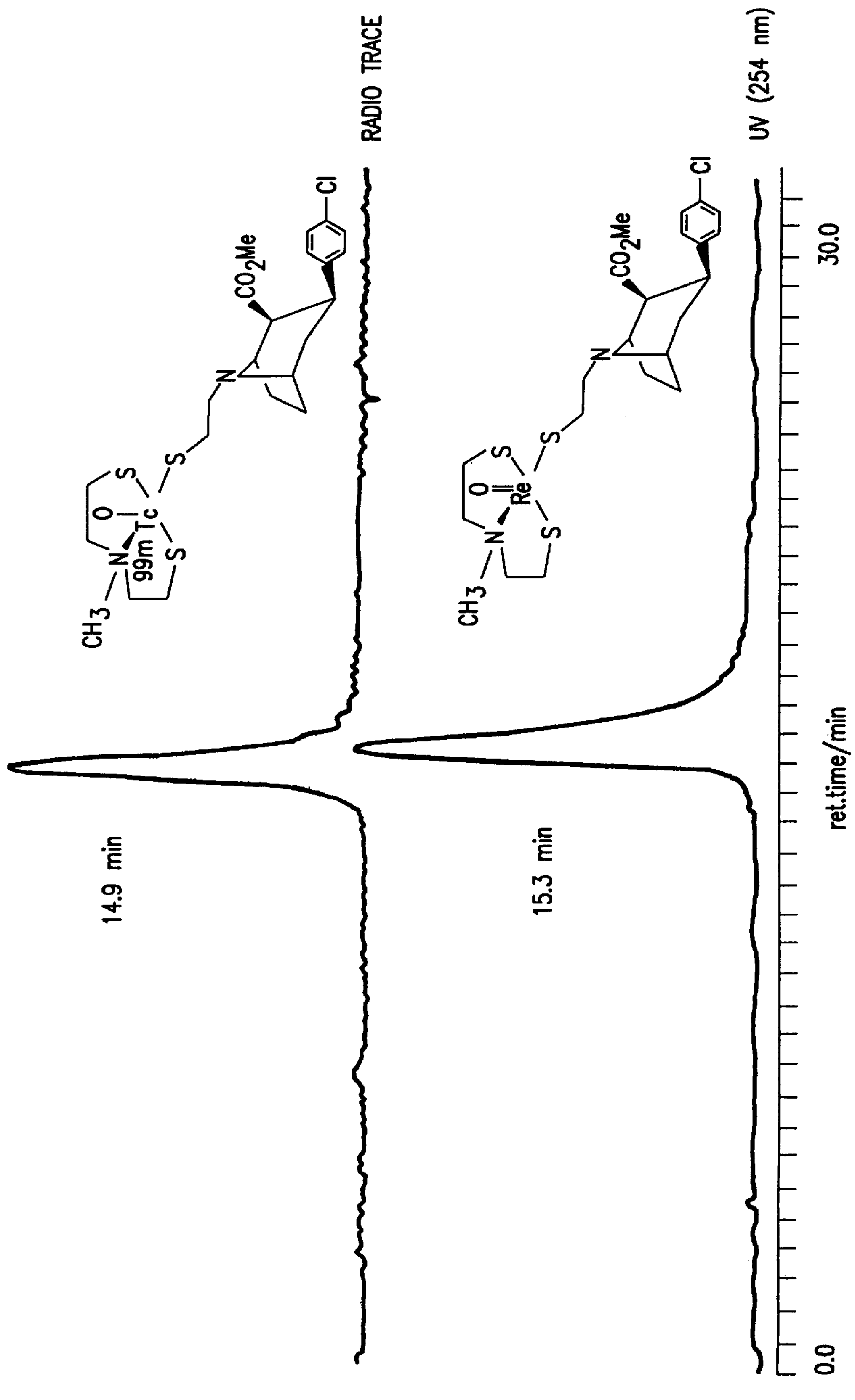
FIG. 18 is a comparison of HPLC traces of 3.23 (UV) and 3.25 (radio trace) on a C-18 column (Partisil 10-ODS-3, 250×4.6 mm) with $MeOH/NH_4HCO_3$ (0.1M, pH 7, ratio 8:2, flow rate 1 ml/min).

Other compounds of Formula I where Z is an ester moiety and the $A_n$ moiety is in the Q position may be synthesized according to the general reaction scheme depicted in FIG. 18 or ones analogous thereto.

Other compounds of Formula I where Z is an ether moiety and the $A^n$ moiety is in the Q position may be synthesized according to the general reaction scheme depicted in FIG. 19 or ones analogous thereto.

In other embodiments of the invention, Z is $COA_2$ and may be prepared according to the general reaction scheme depicted in FIG. 20 or methods analogous thereto.

Generally, methods of making compounds of the invention having an ether linkage couple an alcohol and a halide using NaH.

Figure 21:
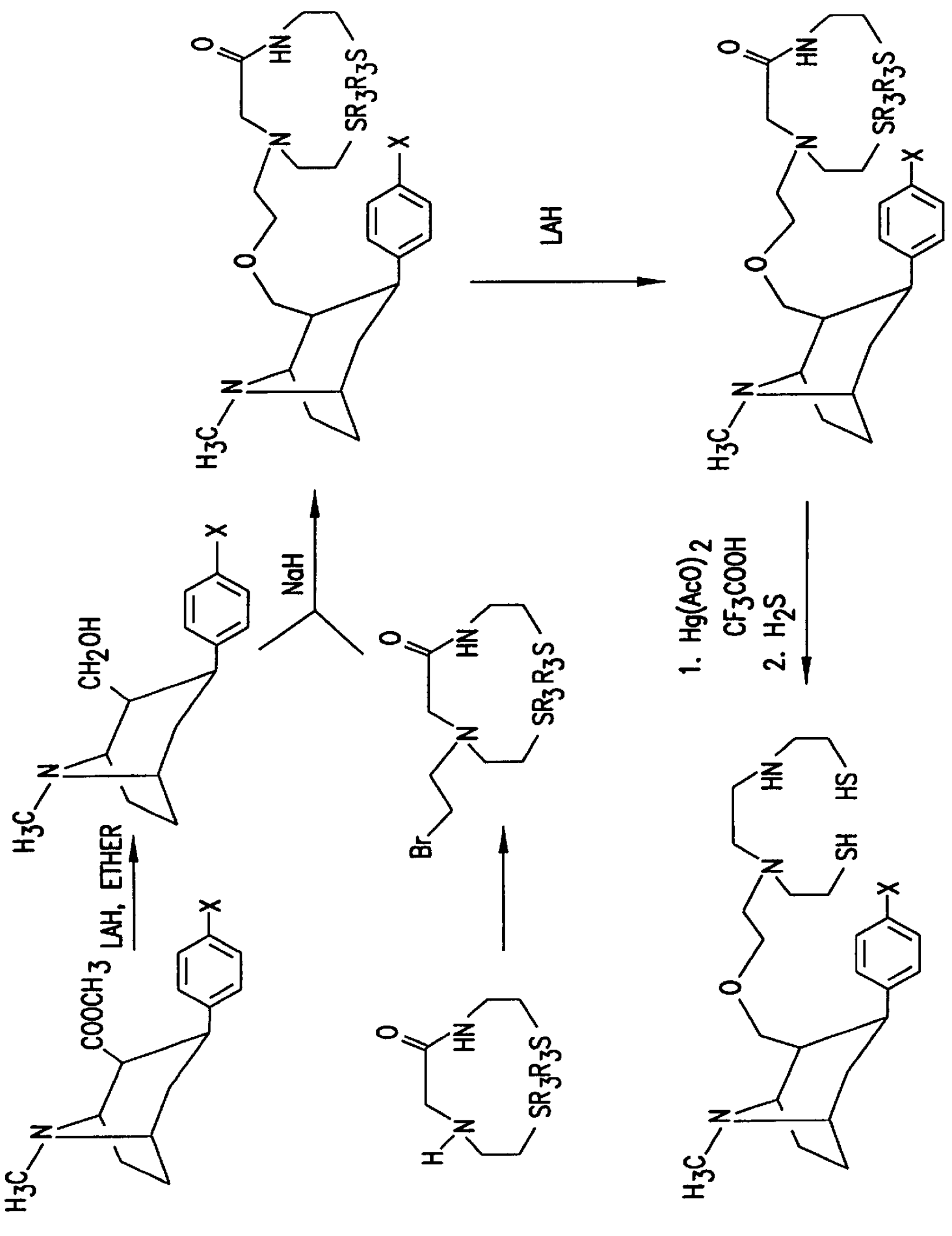
FIG. 21 depicts a reaction scheme where the A moiety of Formula I is in the Z position and the Z moiety is $COA_2$.
Figure 22:
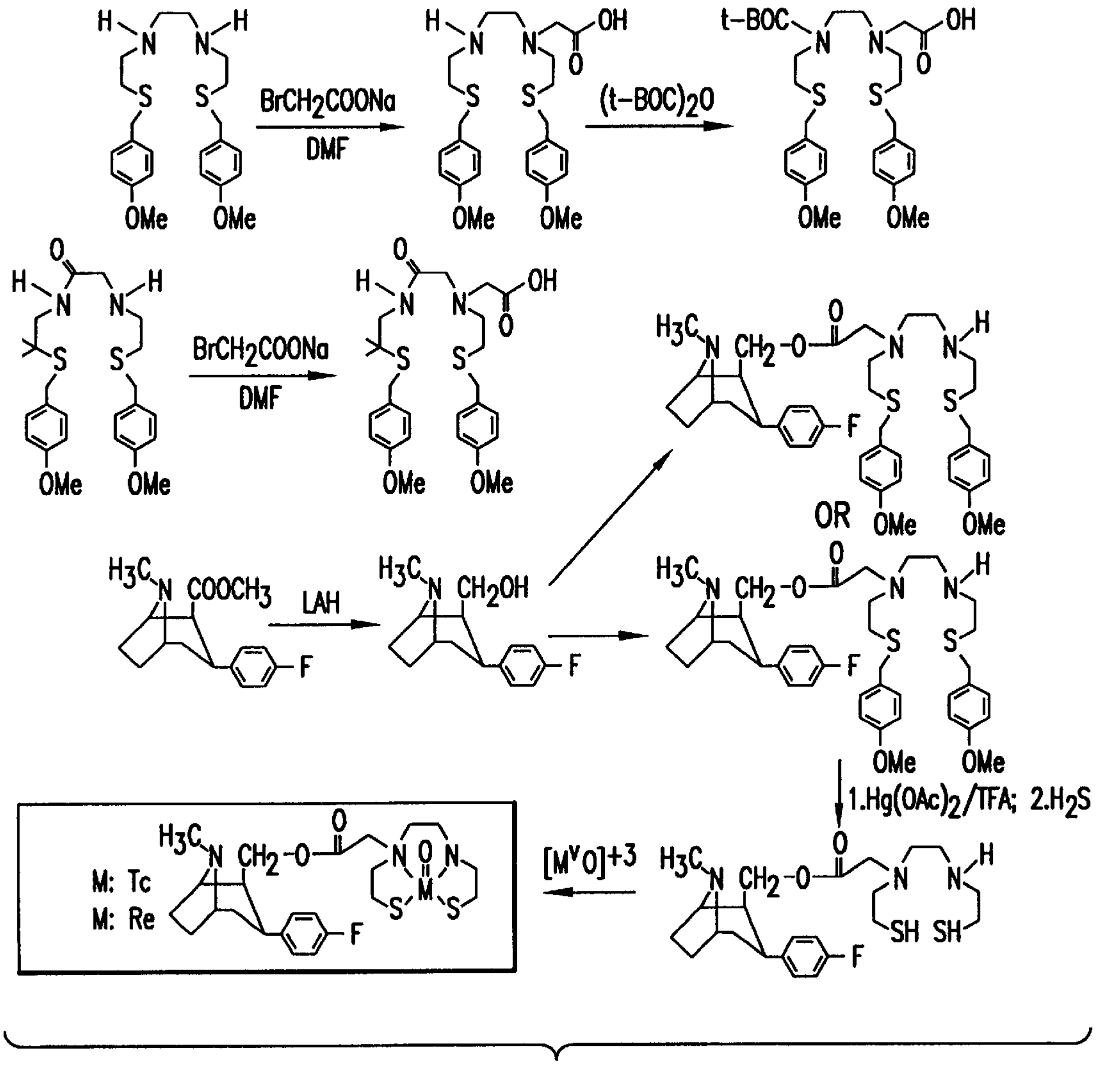
FIG. 22 depicts a reaction scheme where the A moiety is in the Z position and the Z moiety is $CO_2A_2$.

In certain other embodiments, Z is $CO_2A_2$ and may be prepared according to the general reaction scheme depicted in FIG. 21 or ones analogous thereto. In addition to the ester linkage described above and in FIG. 21, amide linkages are also contemplated and may be synthesized according to the general reaction scheme depicted in FIG. 12 or ones analogous thereto.

Figure 23:
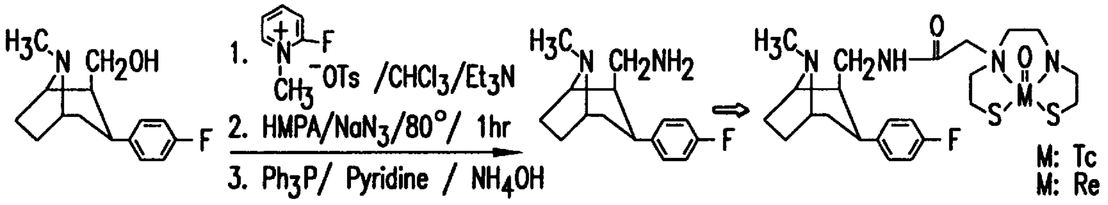
FIG. 23 depicts a reaction scheme where the A moiety is in the Z position and is connected to the tropane core by an amide linkage.
Figure 24:
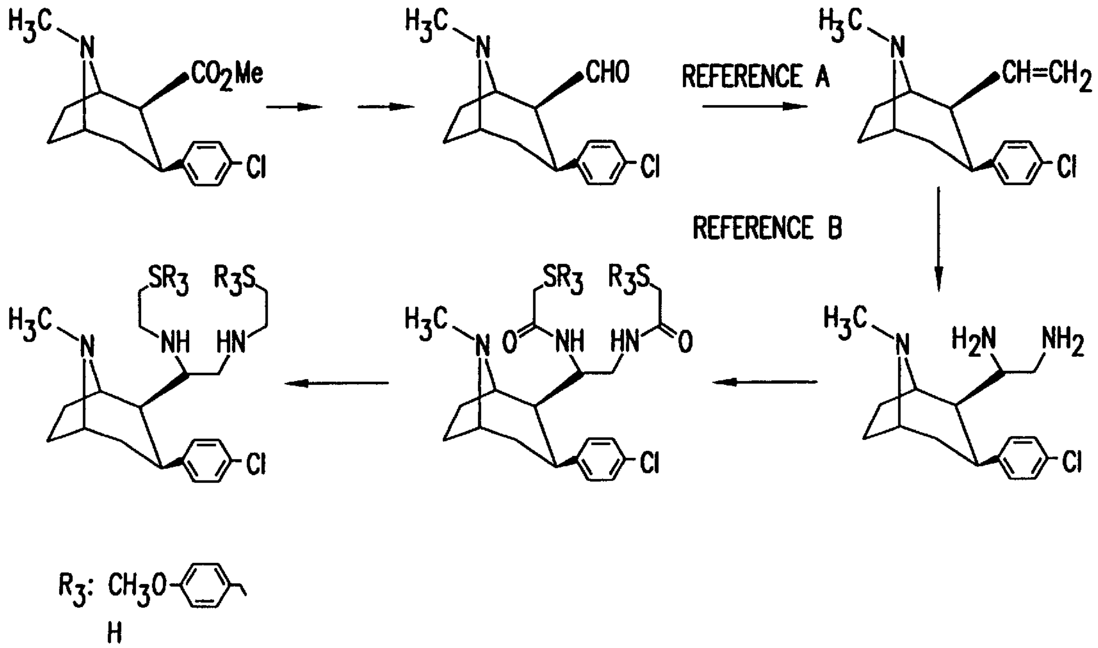
FIG. 24 depicts a reaction scheme where a compound of Formula I is prepared from a direct linkage reaction by eliminating an ester moiety at the Z position.

Other illustrative synthetic methods include those using a direct linkage and elimination of the ester functional group as depicted in FIG. 23. See, e.g., Kung, H. F. et al., *Nucl. Med. Biol.*, 1991, 18, 215–226 (Reference A); and Kozikowski, A. P. et al., *J. Med. Chem.*, 1995, 38, 3086–3093 (Reference B), the disclosures of which are herein incorporated by reference in their entirety.

Persons skilled in the art, once armed with the present disclosure, will be able to select the appropriate starting materials and prepare any of the claimed compounds of the invention.

The compounds of this invention lend themselves easily to the formation from materials that may be assembled in kit form and provided to users. When the novel compounds of the invention are to be used as diagnostic tools, such as imaging agents, the compounds are labeled with a radionuclide, such as technetium. Kits for forming the three plus one complex imaging agents of the invention may contain, for example, a lyophilized composition comprising the tridentate ligand aminodithiol (Formula II) and the monothiol ligand (Formula I, where Z is $A_8$), a reducing agent, preferably the lyophilized composition is a powder. A user would dissolve the lyophilized composition comprising the tridentate ligand aminodithiol and the monothiol ligand in saline and hydrochloric acid. A reducing agent, such as stannous glucoheptonate, and sodium [$^{99m}$Tc] pertechnetate, in saline solution is then added to the mixture. The mixture is then kept at room temperature for about 30 minutes. This is followed by neutralizing the reaction mixture with sodium carbonate. The resulting compounds are extracted into ethyl acetate and the compounds are purified by HPLC.

Preferred compounds of Formula II for inclusion in the kits of the invention are those where, independently or in combination, A is Cl or Fl; B is $A_6$; and D is $CO_2R_5$, wherein $R_5$ is $C_1$–$C_5$ alkyl, or $CO_2R_2$, wherein $R_2$ is a heterocyclic amine. Preferred compounds of Formula II for inclusion in the kits are those where E is $C_1$–$C_2$ alkyl.

Reducing agents suitable for practicing this invention include, but are not limited to, stannous glucoheptonate, stannous chloride, sodium bisulfite, or combinations thereof, with stannous glucoheptonate being preferred. Any other reducing agents known to those skilled in the art may be used without detracting from the spirit of the invention.

Radionuclide-containing compounds suitable for practicing this invention include, but are not limited to, sodium [$^{99m}$Tc] pertechnetate ($Na^{99m}TcO_4$), and sodium pertechnetate ($NaReO_4$), with sodium [$^{99m}$Tc] pertechnetate ($Na^{99m}TcO_4$) being preferred. Other radionuclide-containing compounds known to those skilled in the art may be used without detracting from the spirit of the invention.

Kits containing $N_2S_2$ (bis-aminoethanethiol) complexes are also within the scope of the invention. These kits would generally comprise a lyophllized powder of a the $N_2S_2$ compound, stannous chloride, sodium glucoheptonate, EDTA, hydrochloric acid, and ethanol. A user would dissolve the lyophilized compound ethanol and hydrochloric acid. A reducing agent, such as stannous glucoheptonate, and sodium [$^{99m}$Tc] pertechnetate, and EDTA is added to the mixture. The mixture is then autoclaved for about 30 minutes. After the autoclaving, the mixture is allowed to cool to room temperature. The amount of the solution necessary for analysis is mixed with sodium phosphate before use. The information discussed above in connection with the three plus one complexes is applicable here.

For dopamine transporter imaging agents, the target area of the brain is the striatum, where dopamine transporters are highly concentrated. The cerebellum region is suitable for use as the background region, because it has no dopamine transporters. The specific uptake is measured by the ratio of % dose/gram of striatum divided by % dose/gram of cerebellum (ST/CB ratio)—the higher the value, the better the specific uptake, and the more promising as a dopamine transporter imaging agent.

When using the compounds of the invention as diagnostic agents (such as in imaging techniques) or as therapeutic agents, it is preferable to keep the Tc or Re complex core of the compounds of the invention small. There are stringent structural requirements for achieving both neutral-lipophilicity and dopamine transporter binding affinity for this series of tropane derivatives. The addition of gem-dimethyl groups to a compound of Formula I, dramatically enhances lipophilicity and significantly reduces specific binding to the striatal regions of the brain, where dopamine reuptake sites are located. Fine tuning of size and lipophilicity of technetium or rhenium complexes appears to be important for brain uptake and receptor binding. It is also important that the compounds of the invention have a neutral charge for them to be able to cross into the brain, and therefore, it is preferable that only one nitrogen on the tropane core be substituted. It is also preferable that the $CO_2R$ moiety (Z) and the halogenated phenyl moiety (X) be in the beta position. The examples show that substitution of the $N_2S_2$ moiety ($A_n$ moiety) with gem-dimethyl groups destroys the specificity of the compound (Table 3.1), same is true when the N of the $A_n$ moiety is substituted with groups larger than $C_3$ or with additional amino groups (Table 3.1). Both of these observations are not readily predictable by simple estimation of partition coefficient or molecular weight or size. The partition coefficient value is also very important for the evaluation of potential brain imaging agents, because they must be neutral and lipophilic in order to penetrate the intact blood-brain barrier. Generally, the optimal range of partition coefficient values for good brain uptake are between 100–1000. Apparently, the in vivo biodistribution and receptor binding site for dopamine transporters place unique and highly selectively requirements on this novel groups of agents.

Certain preferred Formula I compounds useful as imaging agents are those comprising a three plus one complex as the ligand and where, independently or in combination, Q or Z includes a compound selected from the group consisting of an $A_7$ or $A_8$ moiety or groups including an $A_7$ or $A_8$ moiety; X is Cl or Br; Z is $CO_2R_1$ or $CO_2R_2$; and E is $C_1$–$C_2$ alkyl. A preferred compound is one where X is Cl; Q is $A_7$ or $A_8$ and n is 2; M is Tc; and Z is $CO_2CH_3$. Other preferred compounds are those where X is Cl; Q is $A_7$ or $A_8$ and n is 2; M is Tc; and Z is $CO_2R_2$, wherein $R_2$ is piperidine, pyrolidine, or morpholine. Still other preferred compounds are those where X is Br; Q is $A_7$ or $A_8$ and n is 2; M is Tc; and Z is $CO_2CH_3$. Other preferred compounds are those where X is Br; Q is $A_7$ or $A_8$ and n is 2; M is Tc; and Z is $CO_2R_2$, wherein $R_2$ is piperidine, pyrolidine, or morpholine.

In other preferred embodiments the Formula I compounds useful as imaging agents are those comprising an $N_2S_2$ ligand in which the ligand is attached to the bridgehead nitrogen of the tropane core, and where X is $C_1$–$C_4$ alkyl, F, Cl, Br, or I; Q is $A_1$, $A_2$, $A_3$, or $A_4$; Z is $CO_2R_1$, or $CO_2R_2$. In other preferred embodiments X is Cl or Br; Q is $A_2$ and n is 2; Z is $CO_2CH_3$; and M is Tc. Other preferred embodiments are those where X is Cl or Br; Q is $A_1$ and n is 2; Z is $CO_2CH_3$; and M is Tc. In still other preferred embodiments, X is Cl or Br; Q is $A_2$ and n is 2; Z is $CO_2R_2$, wherein $R_2$ is piperidine, pyrolidine, or morpholine; and M is Tc. In still other preferred embodiments, X is Cl or Br; Q is $A_1$ and n is 2; Z is $CO_2R_2$, wherein $R_2$ is piperidine, pyrolidine, or morpholine; and M is Tc. The Tc-99m labeled tropane derivative, 2.6a, displayed a significant brain uptake and specific uptake to the striatum area of the rat brain. This compound showed a distinctive difference from both the prior art, technepine, and 3.25.

Particularly preferred Formula I compounds are those comprising an $N_2S_2$ ligand (bis-aminoethanethiol) where the ligand is attached to the 2β position of the tropane core, and where X is $C_1$–$C_4$ alkyl, F, Cl, Br, or I; Z is $A_1$, $A_2$, $A_3$, or $A_4$; Y is $—(CH_2)_n—$; $R_3$ is H; and Q is H or $C_1$–$C_4$ alkyl; and M is Tc. A particularly preferred compound is one where Q is $CH_3$, X is Cl; Z is $A_3$ or $A_4$; and Y is $CH_2$. A particularly preferred compound is one where Q is $CH_3$, X is Br; Z is $A_3$ or $A_4$; and Y is $CH_2$. Another preferred compound is one where Q is $CH_3$, X is Br, Z is $A_1$ or $A_2$, and Y is $CH_2$. Another preferred compound is one where Q is $CH_3$, X is Cl, Z is $A_1$ or $A_2$, and Y is $CH_2$. Experimental data, as discussed in Example 12, demonstrates that chemical compounds 1.19a, 1.19b, and 1.20a having either an $A_2$ or $A_4$ moiety are particularly useful dopamine transporter imaging agents.

This novel series of $N_2S_2$ compounds differ from those previously reported in that the substitution of the bis-aminethanethiol ligand is attached at the 2β-position of the tropane core structure. The corresponding Tc-99m labeled agent displayed a three to fourfold increase in initial brain uptake (0.1% for N-substituted compound (Meegalla, supra) vs. 0.3–0.4% in brain at 2 minutes post-injection) and concomitantly retained the specific uptake in the striatum area of the brain. This observation suggests that, in this series of compounds, the 3β-p-fluoro- is slightly less favorable then the corresponding 3β-p-chlorophenyl derivative. As previously reported for the same series of tropane derivatives, the 3β-p-fluoro- derivative displayed a lower brain uptake, which may be due to its lower binding affinity to dopamine transporters. Carroll, 1995, supra.

Pharmaceutical formulations of the novel ligands of the invention are also within the scope of this invention. Pharmaceutically acceptable diluents suitable for practicing this invention include, but are not limited to, non-pyrogenic physiological saline, and water, with saline being preferred. Any other suitable diluents known to those skilled in the art may be used without departing from the spirit of the invention.

Pharmaceutically accepted salts of the novel compounds of the invention are also within the contemplated scope of the invention. Pharmaceutically acceptable salts suitable for practicing this invention include, but are not limited to, hydrochloride and tartrates.

Another aspect of this invention relates to methods for utilizing the compounds of the invention as CNS imaging agents. Imaging techniques are non-invasive diagnostic techniques that generally involve administering a compound with marker atoms that can be detected externally to the mammal. Generally, these methods comprise administering to a mammal a compound of the invention, dissolved or dispersed in a suitable pharmaceutical carrier or diluent. The compound of the invention selectively binds to CNS receptors, such as dopamine, thus permitting the imaging of CNS receptors and the ability to, inter alia, evaluate brain chemistry, the effectiveness of drugs, and neuronal functions. Imaging techniques suitable for practicing the present invention include, but are not limited to, single photon emission computed tomography (SPECT) and positron emission tomography (PET).

The compounds of the invention are the first receptor specific imaging agents, in particular, the first technetium [$^{99m}$Tc] labeled CNS and are believed to provide a convenient source of short-lived imaging agents for routine diagnosis of CNS abnormality, in conjunction with, for example, single photon emission computed tomography (SPECT).

The technetium [$^{99m}$Tc] isotope has better physical properties than those that are currently available in the art. For example, [$^{99m}$Tc] has a half-life of 6 hours versus a half-life of 13 hours for iodine [$^{123}$I]. Also, [$^{99m}$Tc] is more readily available than [$^{123}$I]. The [$^{123}$I] is a cyclotron produced isotope and is believed to be available from only two commercial sources—Nordion, located in Canada, and Emencia, located in Great Britain. By contrast, [$^{99m}$Tc] is generated using [$^{99m}$Tc]/Mo-99, which is a generator that is used in nuclear medicine techniques and is virtually in all hospitals. Another advantage to the use of [$^{99m}$Tc] is its cost. Using the generator described above, [$^{99m}$Tc] can be made at a cost of $1 per millicurie while the cost of preparing the same amount of iodine would be 30 to 50 times greater. It is also possible to follow the same radiochemistry reactions using radionuclide-containing compounds containing rhenium, which has similar advantages.

The following tables (A–R) provide examples of compounds of Formula I and are intended only for illustrative purposes and in noway limit the scope of the invention. The examples are also illustrative of the invention and are not intended to limit the scope of the invention. The examples illustrate the preparation of compounds within the scope of this invention as well as compounds used for comparison.

TABLE A

| Q | n | X | Z | $R_1$ | E* | M |
|---|---|---|---|---|---|---|
| $A_2$, $A_4$, $A_6$, or $A_7$ | 2 | F | $CO_2R_1$ | $CH_3$ | $CH_2$ | $Tc^{99m}$ |
| $A_2$, $A_4$, $A_6$, or $A_7$ | 2 | Cl | $CO_2R_1$ | $CH_3$ | $CH_2$ | $Tc^{99m}$ |
| $A_2$, $A_4$, $A_6$, or $A_7$ | 2 | Br | $CO_2R_1$ | $CH_3$ | $CH_2$ | $Tc^{99m}$ |
| $A_2$, $A_4$, $A_6$, or $A_7$ | 1 | F | $CO_2R_1$ | $CH_3$ | $CH_2$ | $Tc^{99m}$ |
| $A_2$, $A_4$, $A_6$, or $A_7$ | 1 | Cl | $CO_2R_1$ | $CH_3$ | $CH_2$ | $Tc^{99m}$ |
| $A_2$, $A_4$, $A_6$, or $A_7$ | 1 | Br | $CO_2R_1$ | $CH_3$ | $CH_2$ | $Tc^{99m}$ |
| $A_2$, $A_4$, $A_6$, or $A_7$ | 3 | F | $CO_2R_1$ | $CH_3$ | $CH_2$ | $Tc^{99m}$ |
| $A_2$, $A_4$, $A_6$, or $A_7$ | 3 | Cl | $CO_2R_1$ | $CH_3$ | $CH_2$ | $Tc^{99m}$ |
| $A_2$, $A_4$, $A_6$, or $A_7$ | 3 | Br | $CO_2R_1$ | $CH_3$ | $CH_2$ | $Tc^{99m}$ |
| $A_2$, $A_4$, $A_6$, or $A_7$ | 4 | F | $CO_2R_1$ | $CH_3$ | $CH_2$ | $Tc^{99m}$ |
| $A_2$, $A_4$, $A_6$, or $A_7$ | 4 | Cl | $CO_2R_1$ | $CH_3$ | $CH_2$ | $Tc^{99m}$ |
| $A_2$, $A_4$, $A_6$, or $A_7$ | 4 | Br | $CO_2R_1$ | $CH_3$ | $CH_2$ | $Tc^{99m}$ |
| $A_2$, $A_4$, $A_6$, or $A_7$ | 2 | F | $CO_2R_1$ | $CH_2CH_3$ | $CH_2$ | $Tc^{99m}$ |
| $A_2$, $A_4$, $A_6$, or $A_7$ | 2 | Cl | $CO_2R_1$ | $CH_2CH_3$ | $CH_2$ | $Tc^{99m}$ |
| $A_2$, $A_4$, $A_6$, or $A_7$ | 2 | Br | $CO_2R_1$ | $CH_2CH_3$ | $CH_2$ | $Tc^{99m}$ |
| $A_2$, $A_4$, $A_6$, or $A_7$ | 1 | F | $CO_2R_1$ | $CH_2CH_3$ | $CH_2$ | $Tc^{99m}$ |
| $A_2$, $A_4$, $A_6$, or $A_7$ | 1 | Cl | $CO_2R_1$ | $CH_2CH_3$ | $CH_2$ | $Tc^{99m}$ |
| $A_2$, $A_4$, $A_6$, or $A_7$ | 1 | Br | $CO_2R_1$ | $CH_2CH_3$ | $CH_2$ | $Tc^{99m}$ |
| $A_2$, $A_4$, $A_6$, or $A_7$ | 3 | F | $CO_2R_1$ | $CH_2CH_3$ | $CH_2$ | $Tc^{99m}$ |
| $A_2$, $A_4$, $A_6$, or $A_7$ | 3 | Cl | $CO_2R_1$ | $CH_2CH_3$ | $CH_2$ | $Tc^{99m}$ |
| $A_2$, $A_4$, $A_6$, or $A_7$ | 3 | Br | $CO_2R_1$ | $CH_2CH_3$ | $CH_2$ | $Tc^{99m}$ |
| $A_2$, $A_4$, $A_6$, or $A_7$ | 4 | F | $CO_2R_1$ | $CH_2CH_3$ | $CH_2$ | $Tc^{99m}$ |
| $A_2$, $A_4$, $A_6$, or $A_7$ | 4 | Cl | $CO_2R_1$ | $CH_2CH_3$ | $CH_2$ | $Tc^{99m}$ |
| $A_2$, $A_4$, $A_6$, or $A_7$ | 4 | Br | $CO_2R_1$ | $CH_2CH_3$ | $CH_2$ | $Tc^{99m}$ |

*Applies when A is $A_7$

TABLE B

| Q | n | X | Z | $R_1$ | E* | M |
|---|---|---|---|---|---|---|
| $A_2$, $A_4$, $A_6$, or $A_7$ | 2 | F | $CO_2R_1$ | $CH_3$ | $CH_2CH_3$ | $Tc^{99m}$ |
| $A_2$, $A_4$, $A_6$, or $A_7$ | 2 | Cl | $CO_2R_1$ | $CH_3$ | $CH_2CH_3$ | $Tc^{99m}$ |
| $A_2$, $A_4$, $A_6$, or $A_7$ | 2 | Br | $CO_2R_1$ | $CH_3$ | $CH_2CH_3$ | $Tc^{99m}$ |
| $A_2$, $A_4$, $A_6$, or $A_7$ | 1 | F | $CO_2R_1$ | $CH_3$ | $CH_2CH_3$ | $Tc^{99m}$ |
| $A_2$, $A_4$, $A_6$, or $A_7$ | 1 | Cl | $CO_2R_1$ | $CH_3$ | $CH_2CH_3$ | $Tc^{99m}$ |
| $A_2$, $A_4$, $A_6$, or $A_7$ | 1 | Br | $CO_2R_1$ | $CH_3$ | $CH_2CH_3$ | $Tc^{99m}$ |
| $A_2$, $A_4$, $A_6$, or $A_7$ | 3 | F | $CO_2R_1$ | $CH_3$ | $CH_2CH_3$ | $Tc^{99m}$ |
| $A_2$, $A_4$, $A_6$, or $A_7$ | 3 | Cl | $CO_2R_1$ | $CH_3$ | $CH_2CH_3$ | $Tc^{99m}$ |
| $A_2$, $A_4$, $A_6$, or $A_7$ | 3 | Br | $CO_2R_1$ | $CH_3$ | $CH_2CH_3$ | $Tc^{99m}$ |
| $A_2$, $A_4$, $A_6$, or $A_7$ | 4 | F | $CO_2R_1$ | $CH_3$ | $CH_2CH_3$ | $Tc^{99m}$ |
| $A_2$, $A_4$, $A_6$, or $A_7$ | 4 | Cl | $CO_2R_1$ | $CH_3$ | $CH_2CH_3$ | $Tc^{99m}$ |
| $A_2$, $A_4$, $A_6$, or $A_7$ | 4 | Br | $CO_2R_1$ | $CH_3$ | $CH_2CH_3$ | $Tc^{99m}$ |
| $A_2$, $A_4$, $A_6$, or $A_7$ | 2 | F | $CO_2R_1$ | $CH_2CH_3$ | $CH_2CH_3$ | $Tc^{99m}$ |
| $A_2$, $A_4$, $A_6$, or $A_7$ | 2 | Cl | $CO_2R_1$ | $CH_2CH_3$ | $CH_2CH_3$ | $Tc^{99m}$ |
| $A_2$, $A_4$, $A_6$, or $A_7$ | 2 | Br | $CO_2R_1$ | $CH_2CH_3$ | $CH_2CH_3$ | $Tc^{99m}$ |

TABLE B-continued

| Q | n | X | Z | $R_1$ | E* | M |
|---|---|---|---|---|---|---|
| $A_2$, $A_4$, $A_6$, or $A_7$ | 1 | F | $CO_2R_1$ | $CH_2CH_3$ | $CH_2CH_3$ | $Tc^{99m}$ |
| $A_2$, $A_4$, $A_6$, or $A_7$ | 1 | Cl | $CO_2R_1$ | $CH_2CH_3$ | $CH_2CH_3$ | $Tc^{99m}$ |
| $A_2$, $A_4$, $A_6$, or $A_7$ | 1 | Br | $CO_2R_1$ | $CH_2CH_3$ | $CH_2CH_3$ | $Tc^{99m}$ |
| $A_2$, $A_4$, $A_6$, or $A_7$ | 3 | F | $CO_2R_1$ | $CH_2CH_3$ | $CH_2CH_3$ | $Tc^{99m}$ |
| $A_2$, $A_4$, $A_6$, or $A_7$ | 3 | Cl | $CO_2R_1$ | $CH_2CH_3$ | $CH_2CH_3$ | $Tc^{99m}$ |
| $A_2$, $A_4$, $A_6$, or $A_7$ | 3 | Br | $CO_2R_1$ | $CH_2CH_3$ | $CH_2CH_3$ | $Tc^{99m}$ |
| $A_2$, $A_4$, $A_6$, or $A_7$ | 4 | F | $CO_2R_1$ | $CH_2CH_3$ | $CH_2CH_3$ | $Tc^{99m}$ |
| $A_2$, $A_4$, $A_6$, or $A_7$ | 4 | Cl | $CO_2R_1$ | $CH_2CH_3$ | $CH_2CH_3$ | $Tc^{99m}$ |
| $A_2$, $A_4$, $A_6$, or $A_7$ | 4 | Br | $CO_2R_1$ | $CH_2CH_3$ | $CH_2CH_3$ | $Tc^{99m}$ |

*Applies when A is $A_7$

TABLE C

| Q | n | X | Z | $R_2$ | E* | M |
|---|---|---|---|---|---|---|
| $A_2$, $A_4$, $A_6$, or $A_7$ | 2 | F | $CO_2R_2$ | piperidine, pyrrolidine, or morpholine | $CH_2$ | $Tc^{99m}$ |
| $A_2$, $A_4$, $A_6$, or $A_7$ | 2 | Cl | $CO_2R_2$ | piperidine, pyrrolidine, or morpholine | $CH_2$ | $Tc^{99m}$ |
| $A_2$, $A_4$, $A_6$, or $A_7$ | 2 | Br | $CO_2R_2$ | piperidine, pyrrolidine, or morpholine | $CH_2$ | $Tc^{99m}$ |
| $A_2$, $A_4$, $A_6$, or $A_7$ | 1 | F | $CO_2R_2$ | piperidine, pyrrolidine, or morpholine | $CH_2$ | $Tc^{99m}$ |
| $A_2$, $A_4$, $A_6$, or $A_7$ | 1 | Cl | $CO_2R_2$ | piperidine, pyrrolidine, or morpholine | $CH_2$ | $Tc^{99m}$ |
| $A_2$, $A_4$, $A_6$, or $A_7$ | 1 | Br | $CO_2R_2$ | piperidine, pyrrolidine, or morpholine | $CH_2$ | $Tc^{99m}$ |
| $A_2$, $A_4$, $A_6$, or $A_7$ | 3 | F | $CO_2R_2$ | piperidine, pyrrolidine, or morpholine | $CH_2$ | $Tc^{99m}$ |
| $A_2$, $A_4$, $A_6$, or $A_7$ | 3 | Cl | $CO_2R_2$ | piperidine, pyrrolidine, or morpholine | $CH_2$ | $Tc^{99m}$ |
| $A_2$, $A_4$, $A_6$, or $A_7$ | 3 | Br | $CO_2R_2$ | piperidine, pyrrolidine, or morpholine | $CH_2$ | $Tc^{99m}$ |
| $A_2$, $A_4$, $A_6$, or $A_7$ | 0 | F | $CO_2R_2$ | piperidine, pyrrolidine, or morpholine | $CH_2$ | $Tc^{99m}$ |
| $A_2$, $A_4$, $A_6$, or $A_7$ | 0 | Cl | $CO_2R_2$ | piperidine, pyrrolidine, or morpholine | $CH_2$ | $Tc^{99m}$ |
| $A_2$, $A_4$, $A_6$, or $A_7$ | 0 | Br | $CO_2R_2$ | piperidine, pyrrolidine, or morpholine | $CH_2$ | $Tc^{99m}$ |

Applies when A is $A_7$

TABLE D

| Q | n | X | Z | E* | $R_1$ | M |
|---|---|---|---|---|---|---|
| $A_2$, $A_4$, $A_6$, or $A_7$ | 2 | F | $COR_1$ | $CH_2$ | $CH_3$ | $Tc^{99m}$ |
| $A_2$, $A_4$, $A_6$, or $A_7$ | 2 | Cl | $COR_1$ | $CH_2$ | $CH_3$ | $Tc^{99m}$ |
| $A_2$, $A_4$, $A_6$, or $A_7$ | 2 | Br | $COR_1$ | $CH_2$ | $CH_3$ | $Tc^{99m}$ |
| $A_2$, $A_4$, $A_6$, or $A_7$ | 1 | F | $COR_1$ | $CH_2$ | $CH_3$ | $Tc^{99m}$ |
| $A_2$, $A_4$, $A_6$, or $A_7$ | 1 | Cl | $COR_1$ | $CH_2$ | $CH_3$ | $Tc^{99m}$ |
| $A_2$, $A_4$, $A_6$, or $A_7$ | 1 | Br | $COR_1$ | $CH_2$ | $CH_3$ | $Tc^{99m}$ |
| $A_2$, $A_4$, $A_6$, or $A_7$ | 3 | F | $COR_1$ | $CH_2$ | $CH_3$ | $Tc^{99m}$ |
| $A_2$, $A_4$, $A_6$, or $A_7$ | 3 | Cl | $COR_1$ | $CH_2$ | $CH_3$ | $Tc^{99m}$ |
| $A_2$, $A_4$, $A_6$, or $A_7$ | 3 | Br | $COR_1$ | $CH_2$ | $CH_3$ | $Tc^{99m}$ |
| $A_2$, $A_4$, $A_6$, or $A_7$ | 0 | F | $COR_1$ | $CH_2$ | $CH_3$ | $Tc^{99m}$ |
| $A_2$, $A_4$, $A_6$, or $A_7$ | 0 | Cl | $COR_1$ | $CH_2$ | $CH_3$ | $Tc^{99m}$ |
| $A_2$, $A_4$, $A_6$, or $A_7$ | 0 | Br | $COR_1$ | $CH_2$ | $CH_3$ | $Tc^{99m}$ |
| $A_2$, $A_4$, $A_6$, or $A_7$ | 2 | F | $COR_1$ | $CH_2$ | $CH_2CH_3$ | $Tc^{99m}$ |
| $A_2$, $A_4$, $A_6$, or $A_7$ | 2 | Cl | $COR_1$ | $CH_2$ | $CH_2CH_3$ | $Tc^{99m}$ |
| $A_2$, $A_4$, $A_6$, or $A_7$ | 2 | Br | $COR_1$ | $CH_2$ | $CH_2CH_3$ | $Tc^{99m}$ |

TABLE D-continued

| Q | n | X | Z | E* | $R_1$ | M |
|---|---|---|---|---|---|---|
| $A_2$, $A_4$, $A_6$, or $A_7$ | 1 | F | $COR_1$ | $CH_2$ | $CH_2CH_3$ | $Tc^{99m}$ |
| $A_2$, $A_4$, $A_6$, or $A_7$ | 1 | Cl | $COR_1$ | $CH_2$ | $CH_2CH_3$ | $Tc^{99m}$ |
| $A_2$, $A_4$, $A_6$, or $A_7$ | 1 | Br | $COR_1$ | $CH_2$ | $CH_2CH_3$ | $Tc^{99m}$ |
| $A_2$, $A_4$, $A_6$, or $A_7$ | 3 | F | $COR_1$ | $CH_2$ | $CH_2CH_3$ | $Tc^{99m}$ |
| $A_2$, $A_4$, $A_6$, or $A_7$ | 3 | Cl | $COR_1$ | $CH_2$ | $CH_2CH_3$ | $Tc^{99m}$ |
| $A_2$, $A_4$, $A_6$, or $A_7$ | 3 | Br | $COR_1$ | $CH_2$ | $CH_2CH_3$ | $Tc^{99m}$ |
| $A_2$, $A_4$, $A_6$, or $A_7$ | 0 | F | $COR_1$ | $CH_2$ | $CH_2CH_3$ | $Tc^{99m}$ |
| $A_2$, $A_4$, $A_6$, or $A_7$ | 0 | Cl | $COR_1$ | $CH_2$ | $CH_2CH_3$ | $Tc^{99m}$ |
| $A_2$, $A_4$, $A_6$, or $A_7$ | 0 | Br | $COR_1$ | $CH_2$ | $CH_2CH_3$ | $Tc^{99m}$ |

*Applies when A is $A_7$

TABLE E

| Q | n | X | Z | E* | $R_1$ | M |
|---|---|---|---|---|---|---|
| $A_2$, $A_4$, $A_6$, or $A_7$ | 2 | F | $COR_1$ | $CH_2CH_3$ | $CH_3$ | $Tc^{99m}$ |
| $A_2$, $A_4$, $A_6$, or $A_7$ | 2 | Cl | $COR_1$ | $CH_2CH_3$ | $CH_3$ | $Tc^{99m}$ |
| $A_2$, $A_4$, $A_6$, or $A_7$ | 2 | Br | $COR_1$ | $CH_2CH_3$ | $CH_3$ | $Tc^{99m}$ |
| $A_2$, $A_4$, $A_6$, or $A_7$ | 1 | F | $COR_1$ | $CH_2CH_3$ | $CH_3$ | $Tc^{99m}$ |
| $A_2$, $A_4$, $A_6$, or $A_7$ | 1 | Cl | $COR_1$ | $CH_2CH_3$ | $CH_3$ | $Tc^{99m}$ |
| $A_2$, $A_4$, $A_6$, or $A_7$ | 1 | Br | $COR_1$ | $CH_2CH_3$ | $CH_3$ | $Tc^{99m}$ |
| $A_2$, $A_4$, $A_6$, or $A_7$ | 3 | F | $COR_1$ | $CH_2CH_3$ | $CH_3$ | $Tc^{99m}$ |
| $A_2$, $A_4$, $A_6$, or $A_7$ | 3 | Cl | $COR_1$ | $CH_2CH_3$ | $CH_3$ | $Tc^{99m}$ |
| $A_2$, $A_4$, $A_6$, or $A_7$ | 3 | Br | $COR_1$ | $CH_2CH_3$ | $CH_3$ | $Tc^{99m}$ |
| $A_2$, $A_4$, $A_6$, or $A_7$ | 0 | F | $COR_1$ | $CH_2CH_3$ | $CH_3$ | $Tc^{99m}$ |
| $A_2$, $A_4$, $A_6$, or $A_7$ | 0 | Cl | $COR_1$ | $CH_2CH_3$ | $CH_3$ | $Tc^{99m}$ |
| $A_2$, $A_4$, $A_6$, or $A_7$ | 0 | Br | $COR_1$ | $CH_2CH_3$ | $CH_3$ | $Tc^{99m}$ |
| $A_2$, $A_4$, $A_6$, or $A_7$ | 2 | F | $COR_1$ | $CH_2CH_3$ | $CH_2CH_3$ | $Tc^{99m}$ |
| $A_2$, $A_4$, $A_6$, or $A_7$ | 2 | Cl | $COR_1$ | $CH_2CH_3$ | $CH_2CH_3$ | $Tc^{99m}$ |
| $A_2$, $A_4$, $A_6$, or $A_7$ | 2 | Br | $COR_1$ | $CH_2CH_3$ | $CH_2CH_3$ | $Tc^{99m}$ |
| $A_2$, $A_4$, $A_6$, or $A_7$ | 1 | F | $COR_1$ | $CH_2CH_3$ | $CH_2CH_3$ | $Tc^{99m}$ |
| $A_2$, $A_4$, $A_6$, or $A_7$ | 1 | Cl | $COR_1$ | $CH_2CH_3$ | $CH_2CH_3$ | $Tc^{99m}$ |
| $A_2$, $A_4$, $A_6$, or $A_7$ | 1 | Br | $COR_1$ | $CH_2CH_3$ | $CH_2CH_3$ | $Tc^{99m}$ |
| $A_2$, $A_4$, $A_6$, or $A_7$ | 3 | F | $COR_1$ | $CH_2CH_3$ | $CH_2CH_3$ | $Tc^{99m}$ |
| $A_2$, $A_4$, $A_6$, or $A_7$ | 3 | Cl | $COR_1$ | $CH_2CH_3$ | $CH_2CH_3$ | $Tc^{99m}$ |
| $A_2$, $A_4$, $A_6$, or $A_7$ | 3 | Br | $COR_1$ | $CH_2CH_3$ | $CH_2CH_3$ | $Tc^{99m}$ |
| $A_2$, $A_4$, $A_6$, or $A_7$ | 0 | F | $COR_1$ | $CH_2CH_3$ | $CH_2CH_3$ | $Tc^{99m}$ |
| $A_2$, $A_4$, $A_6$, or $A_7$ | 0 | Cl | $COR_1$ | $CH_2CH_3$ | $CH_2CH_3$ | $Tc^{99m}$ |
| $A_2$, $A_4$, $A_6$, or $A_7$ | 0 | Br | $COR_1$ | $CH_2CH_3$ | $CH_2CH_3$ | $Tc^{99m}$ |

*Applies when A is $A_7$

TABLE F

| Q | n | X | z | E* | M |
|---|---|---|---|---|---|
| $CH_3$ | 2 | F | $COA_2$, $COA_4$, $COA_6$, or $COA_7$ | $CH_2$ | $Tc^{99m}$ |
| $CH_3$ | 2 | Cl | $COA_2$, $COA_4$, $COA_6$, or $COA_7$ | $CH_2$ | $Tc^{99m}$ |
| $CH_3$ | 2 | Cl | $COA_2$, $COA_4$, $COA_6$, or $COA_7$ | $CH_2$ | $Tc^{99m}$ |
| $CH_3$ | 1 | F | $COA_2$, $COA_4$, $COA_6$, or $COA_7$ | $CH_2$ | $Tc^{99m}$ |
| $CH_3$ | 1 | Cl | $COA_2$, $COA_4$, $COA_6$, or $COA_7$ | $CH_2$ | $Tc^{99m}$ |
| $CH_3$ | 1 | F | $COA_2$, $COA_4$, $COA_6$, or $COA_7$ | $CH_2$ | $Tc^{99m}$ |
| $CH_3$ | 3 | F | $COA_2$, $COA_4$, $COA_6$, or $COA_7$ | $CH_2$ | $Tc^{99m}$ |
| $CH_3$ | 3 | Cl | $COA_2$, $COA_4$, $COA_6$, or $COA_7$ | $CH_2$ | $Tc^{99m}$ |
| $CH_3$ | 3 | Cl | $COA_2$, $COA_4$, $COA_6$, or $COA_7$ | $CH_2$ | $Tc^{99m}$ |
| $CH_3$ | 0 | F | $COA_2$, $COA_4$, $COA_6$, or $COA_7$ | $CH_2$ | $Tc^{99m}$ |
| $CH_3$ | 0 | Cl | $COA_2$, $COA_4$, $COA_6$, or $COA_7$ | $CH_2$ | $Tc^{99m}$ |
| $CH_3$ | 0 | Cl | $COA_2$, $COA_4$, $COA_6$, or $COA_7$ | $CH_2$ | $Tc^{99m}$ |
| $CH_3$ | 2 | F | $COA_2$, $COA_4$, $COA_6$, or $COA_7$ | $CH_2$ | $Tc^{99m}$ |
| $CH_3$ | 2 | Cl | $COA_2$, $COA_4$, $COA_6$, or $COA_7$ | $CH_2$ | $Tc^{99m}$ |
| $CH_3$ | 2 | F | $COA_2$, $COA_4$, $COA_6$, or $COA_7$ | $CH_2$ | $Tc^{99m}$ |
| $CH_3$ | 1 | F | $COA_2$, $COA_4$, $COA_6$, or $COA_7$ | $CH_2$ | $Tc^{99m}$ |
| $CH_3$ | 1 | Cl | $COA_2$, $COA_4$, $COA_6$, or $COA_7$ | $CH_2$ | $Tc^{99m}$ |
| $CH_3$ | 1 | F | $COA_2$, $COA_4$, $COA_6$, or $COA_7$ | $CH_2$ | $Tc^{99m}$ |
| $CH_3$ | 3 | F | $COA_2$, $COA_4$, $COA_6$, or $COA_7$ | $CH_2$ | $Tc^{99m}$ |
| $CH_3$ | 3 | Cl | $COA_2$, $COA_4$, $COA_6$, or $COA_7$ | $CH_2$ | $Tc^{99m}$ |
| $CH_3$ | 3 | F | $COA_2$, $COA_4$, $COA_6$, or $COA_7$ | $CH_2$ | $Tc^{99m}$ |
| $CH_3$ | 0 | F | $COA_2$, $COA_4$, $COA_6$, or $COA_7$ | $CH_2$ | $Tc^{99m}$ |
| $CH_3$ | 0 | Cl | $COA_2$, $COA_4$, $COA_6$, or $COA_7$ | $CH_2$ | $Tc^{99m}$ |
| $CH_3$ | 0 | F | $COA_2$, $COA_4$, $COA_6$, or $COA_7$ | $CH_2$ | $Tc^{99m}$ |

Applies when A is $A_7$

TABLE G

| Q | n | X | z | E* | M |
|---|---|---|---|---|---|
| $CH_3$ | 2 | F | $COA_2$, $COA_4$, $COA_6$, or $COA_7$ | $CH_2CH_3$ | $Tc^{99m}$ |
| $CH_3$ | 2 | Cl | $COA_2$, $COA_4$, $COA_6$, or $COA_7$ | $CH_2CH_3$ | $Tc^{99m}$ |
| $CH_3$ | 2 | Cl | $COA_2$, $COA_4$, $COA_6$, or $COA_7$ | $CH_2CH_3$ | $Tc^{99m}$ |
| $CH_3$ | 1 | F | $COA_2$, $COA_4$, $COA_6$, or $COA_7$ | $CH_2CH_3$ | $Tc^{99m}$ |
| $CH_3$ | 1 | Cl | $COA_2$, $COA_4$, $COA_6$, or $COA_7$ | $CH_2CH_3$ | $Tc^{99m}$ |
| $CH_3$ | 1 | F | $COA_2$, $COA_4$, $COA_6$, or $COA_7$ | $CH_2CH_3$ | $Tc^{99m}$ |
| $CH_3$ | 3 | F | $COA_2$, $COA_4$, $COA_6$, or $COA_7$ | $CH_2CH_3$ | $Tc^{99m}$ |
| $CH_3$ | 3 | Cl | $COA_2$, $COA_4$, $COA_6$, or $COA_7$ | $CH_2CH_3$ | $Tc^{99m}$ |
| $CH_3$ | 3 | Cl | $COA_2$, $COA_4$, $COA_6$, or $COA_7$ | $CH_2CH_3$ | $Tc^{99m}$ |
| $CH_3$ | 0 | F | $COA_2$, $COA_4$, $COA_6$, or $COA_7$ | $CH_2CH_3$ | $Tc^{99m}$ |
| $CH_3$ | 0 | Cl | $COA_2$, $COA_4$, $COA_6$, or $COA_7$ | $CH_2CH_3$ | $Tc^{99m}$ |
| $CH_3$ | 0 | Cl | $COA_2$, $COA_4$, $COA_6$, or $COA_7$ | $CH_2CH_3$ | $Tc^{99m}$ |
| $CH_3$ | 2 | F | $COA_2$, $COA_4$, $COA_6$, or $COA_7$ | $CH_2CH_3$ | $Tc^{99m}$ |
| $CH_3$ | 2 | Cl | $COA_2$, $COA_4$, $COA_6$, or $COA_7$ | $CH_2CH_3$ | $Tc^{99m}$ |
| $CH_3$ | 2 | F | $COA_2$, $COA_4$, $COA_6$, or $COA_7$ | $CH_2CH_3$ | $Tc^{99m}$ |
| $CH_3$ | 1 | F | $COA_2$, $COA_4$, $COA_6$, or $COA_7$ | $CH_2CH_3$ | $Tc^{99m}$ |
| $CH_3$ | 1 | Cl | $COA_2$, $COA_4$, $COA_6$, or $COA_7$ | $CH_2CH_3$ | $Tc^{99m}$ |
| $CH_3$ | 1 | F | $COA_2$, $COA_4$, $COA_6$, or $COA_7$ | $CH_2CH_3$ | $Tc^{99m}$ |
| $CH_3$ | 3 | F | $COA_2$, $COA_4$, $COA_6$, or $COA_7$ | $CH_2CH_3$ | $Tc^{99m}$ |
| $CH_3$ | 3 | Cl | $COA_2$, $COA_4$, $COA_6$, or $COA_7$ | $CH_2CH_3$ | $Tc^{99m}$ |
| $CH_3$ | 3 | F | $COA_2$, $COA_4$, $COA_6$, or $COA_7$ | $CH_2CH_3$ | $Tc^{99m}$ |
| $CH_3$ | 0 | F | $COA_2$, $COA_4$, $COA_6$, or $COA_7$ | $CH_2CH_3$ | $Tc^{99m}$ |
| $CH_3$ | 0 | Cl | $COA_2$, $COA_4$, $COA_6$, or $COA_7$ | $CH_2CH_3$ | $Tc^{99m}$ |
| $CH_3$ | 0 | F | $COA_2$, $COA_4$, $COA_6$, or $COA_7$ | $CH_2CH_3$ | $Tc^{99m}$ |

Applies when A is $A_7$

TABLE H

| Q | Z | n | E* | X | M |
|---|---|---|---|---|---|
| $CH_3$ | $CH_2NHA_3$ | 1 | $CH_2$ | Cl, F, or Br | $Tc^{99m}$ |
| $CH_2CH_3$ | $CH_2NHA_3$ | 1 | $CH_2$ | Cl, F, or Br | $Tc^{99m}$ |
| $CH_2CH_2CH_3$ | $CH_2NHA_3$ | 1 | $CH_2$ | Cl, F, or Br | $Tc^{99m}$ |
| $CH_2CH_2CH_2CH_3$ | $CH_2NHA_3$ | 1 | $CH_2$ | Cl, F, or Br | $Tc^{99m}$ |
| $CH_3$ | $CH_2NHA_3$ | 2 | $CH_2$ | Cl, F, or Br | $Tc^{99m}$ |
| $CH_2CH_3$ | $CH_2NHA_3$ | 2 | $CH_2$ | Cl, F, or Br | $Tc^{99m}$ |
| $CH_2CH_2CH_3$ | $CH_2NHA_3$ | 2 | $CH_2$ | Cl, F, or Br | $Tc^{99m}$ |
| $CH_2CH_2CH_2CH_3$ | $CH_2NHA_3$ | 2 | $CH_2$ | Cl, F, or Br | $Tc^{99m}$ |
| $CH_3$ | $CH_2NHA_3$ | 3 | $CH_2$ | Cl, F, or Br | $Tc^{99m}$ |
| $CH_2CH_3$ | $CH_2NHA_3$ | 3 | $CH_2$ | Cl, F, or Br | $Tc^{99m}$ |
| $CH_2CH_2CH_3$ | $CH_2NHA_3$ | 3 | $CH_2$ | Cl, F, or Br | $Tc^{99m}$ |
| $CH_2CH_2CH_2CH_3$ | $CH_2NHA_3$ | 3 | $CH_2$ | Cl, F, or Br | $Tc^{99m}$ |
| $CH_3$ | $CH_2NHA_3$ | 0 | $CH_2$ | Cl, F, or Br | $Tc^{99m}$ |
| $CH_2CH_3$ | $CH_2NHA_3$ | 0 | $CH_2$ | Cl, F, or Br | $Tc^{99m}$ |
| $CH_2CH_2CH_3$ | $CH_2NHA_3$ | 0 | $CH_2$ | Cl, F, or Br | $Tc^{99m}$ |
| $CH_2CH_2CH_2CH_3$ | $CH_2NHA_3$ | 0 | $CH_2$ | Cl, F, or Br | $Tc^{99m}$ |

*Applies when A is $A_7$

TABLE I

| Q | Z | n | E* | X | M |
|---|---|---|---|---|---|
| $CH_3$ | $CH_2NHA_3$ | 1 | $CH_2CH_3$ | Cl, F, or Br | $Tc^{99m}$ |
| $CH_2CH_3$ | $CH_2NHA_3$ | 1 | $CH_2CH_3$ | Cl, F, or Br | $Tc^{99m}$ |
| $CH_2CH_2CH_3$ | $CH_2NHA_3$ | 1 | $CH_2CH_3$ | Cl, F, or Br | $Tc^{99m}$ |
| $CH_2CH_2CH_2CH_3$ | $CH_2NHA_3$ | 1 | $CH_2CH_3$ | Cl, F, or Br | $Tc^{99m}$ |
| $CH_3$ | $CH_2NHA_3$ | 2 | $CH_2CH_3$ | Cl, F, or Br | $Tc^{99m}$ |
| $CH_2CH_3$ | $CH_2NHA_3$ | 2 | $CH_2CH_3$ | Cl, F, or Br | $Tc^{99m}$ |
| $CH_2CH_2CH_3$ | $CH_2NHA_3$ | 2 | $CH_2CH_3$ | Cl, F, or Br | $Tc^{99m}$ |
| $CH_2CH_2CH_2CH_3$ | $CH_2NHA_3$ | 2 | $CH_2CH_3$ | Cl, F, or Br | $Tc^{99m}$ |
| $CH_3$ | $CH_2NHA_3$ | 3 | $CH_2CH_3$ | Cl, F, or Br | $Tc^{99m}$ |
| $CH_2CH_3$ | $CH_2NHA_3$ | 3 | $CH_2CH_3$ | Cl, F, or Br | $Tc^{99m}$ |
| $CH_2CH_2CH_3$ | $CH_2NHA_3$ | 3 | $CH_2CH_3$ | Cl, F, or Br | $Tc^{99m}$ |
| $CH_2CH_2CH_2CH_3$ | $CH_2NHA_3$ | 3 | $CH_2CH_3$ | Cl, F, or Br | $Tc^{99m}$ |
| $CH_3$ | $CH_2NHA_3$ | 0 | $CH_2CH_3$ | Cl, F, or Br | $Tc^{99m}$ |
| $CH_2CH_3$ | $CH_2NHA_3$ | 0 | $CH_2CH_3$ | Cl, F, or Br | $Tc^{99m}$ |
| $CH_2CH_2CH_3$ | $CH_2NHA_3$ | 0 | $CH_2CH_3$ | Cl, F, or Br | $Tc^{99m}$ |
| $CH_2CH_2CH_2CH_3$ | $CH_2NHA_3$ | 0 | $CH_2CH_3$ | Cl, F, or Br | $Tc^{99m}$ |

*Applies when A is $A_7$

TABLE J

| Q | Z | n | X | E* | M |
|---|---|---|---|---|---|
| $CH_3$ | $CO_2A_2$, $CO_2A_4$, $CO_2A_6$, $CO_2A_7$ | 1 | Cl, F, or Br | $CH_2$ | $Tc^{99m}$ |
| $CH_2CH_3$ | $CO_2A_2$, $CO_2A_4$, $CO_2A_6$, $CO_2A$ | 1 | Cl, F, or Br | $CH_2$ | $Tc^{99m}$ |
| $CH_2CH_2CH_3$ | $CO_2A_2$, $CO_2A_4$, $CO_2A_6$, $CO_2A$ | 1 | Cl, F, or Br | $CH_2$ | $Tc^{99m}$ |
| $CH_2CH_2CH_2CH_3$ | $CO_2A_2$, $CO_2A_4$, $CO_2A_6$, $CO_2A$ | 1 | Cl, F, or Br | $CH_2$ | $Tc^{99m}$ |
| $CH_3$ | $CO_2A_2$, $CO_2A_4$, $CO_2A_6$, $CO_2A$ | 2 | Cl, F, or Br | $CH_2$ | $Tc^{99m}$ |
| $CH_2CH_3$ | $CO_2A_2$, $CO_2A_4$, $CO_2A_6$, $CO_2A$ | 2 | Cl, F, or Br | $CH_2$ | $Tc^{99m}$ |
| $CH_2CH_2CH_3$ | $CO_2A_2$, $CO_2A_4$, $CO_2A_6$, $CO_2A$ | 2 | Cl, F, or Br | $CH_2$ | $Tc^{99m}$ |
| $CH_2CH_2CH_2CH_3$ | $CO_2A_2$, $CO_2A_4$, $CO_2A_6$, $CO_2A$ | 2 | Cl, F, or Br | $CH_2$ | $Tc^{99m}$ |
| $CH_3$ | $CO_2A_2$, $CO_2A_4$, $CO_2A_6$, $CO_2A$ | 3 | Cl, F, or Br | $CH_2$ | $Tc^{99m}$ |
| $CH_2CH_3$ | $CO_2A_2$, $CO_2A_4$, $CO_2A_6$, $CO_2A$ | 3 | Cl, F, or Br | $CH_2$ | $Tc^{99m}$ |
| $CH_2CH_2CH_3$ | $CO_2A_2$, $CO_2A_4$, $CO_2A_6$, $CO_2A$ | 3 | Cl, F, or Br | $CH_2$ | $Tc^{99m}$ |
| $CH_2CH_2CH_2CH_3$ | $CO_2A_2$, $CO_2A_4$, $CO_2A_6$, $CO_2A$ | 3 | Cl, F, or Br | $CH_2$ | $Tc^{99m}$ |
| $CH_3$ | $CO_2A_2$, $CO_2A_4$, $CO_2A_6$, $CO_2A$ | 0 | Cl, F, or Br | $CH_2$ | $Tc^{99m}$ |
| $CH_2CH_3$ | $CO_2A_2$, $CO_2A_4$, $CO_2A_6$, $CO_2A$ | 0 | Cl, F, or Br | $CH_2$ | $Tc^{99m}$ |
| $CH_2CH_2CH_3$ | $CO_2A_2$, $CO_2A_4$, $CO_2A_6$, $CO_2A$ | 0 | Cl, F, or Br | $CH_2$ | $Tc^{99m}$ |
| $CH_2CH_2CH_2CH_3$ | $CO_2A_2$, $CO_2A_4$, $CO_2A_6$, $CO_2A$ | 0 | Cl, F, or Br | $CH_2$ | $Tc^{99m}$ |

*Applies when A is $A_7$

TABLE K

| Q | Z | n | X | E* | M |
|---|---|---|---|---|---|
| $CH_3$ | $CO_2A_2$, $CO_2A_4$, $CO_2A_6$, $CO_2A$ | 1 | Cl, F, or Br | $CH_2CH_3$ | $Tc^{99m}$ |
| $CH_2CH_3$ | $CO_2A_2$, $CO_2A_4$, $CO_2A_6$, $CO_2A$ | 1 | Cl, F, or Br | $CH_2CH_3$ | $Tc^{99m}$ |
| $CH_2CH_2CH_3$ | $CO_2A_2$, $CO_2A_4$, $CO_2A_6$, $CO_2A$ | 1 | Cl, F, or Br | $CH_2CH_3$ | $Tc^{99m}$ |
| $CH_2CH_2CH_2CH_3$ | $CO_2A_2$, $CO_2A_4$, $CO_2A_6$, $CO_2A$ | 1 | Cl, F, or Br | $CH_2CH_3$ | $Tc^{99m}$ |
| $CH_3$ | $CO_2A_2$, $CO_2A_4$, $CO_2A_6$, $CO_2A$ | 2 | Cl, F, or Br | $CH_2CH_3$ | $Tc^{99m}$ |
| $CH_2CH_3$ | $CO_2A_2$, $CO_2A_4$, $CO_2A_6$, $CO_2A$ | 2 | Cl, F, or Br | $CH_2CH_3$ | $Tc^{99m}$ |
| $CH_2CH_2CH_3$ | $CO_2A_2$, $CO_2A_4$, $CO_2A_6$, $CO_2A$ | 2 | Cl, F, or Br | $CH_2CH_3$ | $Tc^{99m}$ |
| $CH_2CH_2CH_2CH_3$ | $CO_2A_2$, $CO_2A_4$, $CO_2A_6$, $CO_2A$ | 2 | Cl, F, or Br | $CH_2CH_3$ | $Tc^{99m}$ |
| $CH_3$ | $CO_2A_2$, $CO_2A_4$, $CO_2A_6$, $CO_2A$ | 3 | Cl, F, or Br | $CH_2CH_3$ | $Tc^{99m}$ |
| $CH_2CH_3$ | $CO_2A_2$, $CO_2A_4$, $CO_2A_6$, $CO_2A$ | 3 | Cl, F, or Br | $CH_2CH_3$ | $Tc^{99m}$ |
| $CH_2CH_2CH_3$ | $CO_2A_2$, $CO_2A_4$, $CO_2A_6$, $CO_2A$ | 3 | Cl, F, or Br | $CH_2CH_3$ | $Tc^{99m}$ |
| $CH_2CH_2CH_2CH_3$ | $CO_2A_2$, $CO_2A_4$, $CO_2A_6$, $CO_2A$ | 3 | Cl, F, or Br | $CH_2CH_3$ | $Tc^{99m}$ |
| $CH_3$ | $CO_2A_2$, $CO_2A_4$, $CO_2A_6$, $CO_2A$ | 0 | Cl, F, or Br | $CH_2CH_3$ | $Tc^{99m}$ |
| $CH_2CH_3$ | $CO_2A_2$, $CO_2A_4$, $CO_2A_6$, $CO_2A$ | 0 | Cl, F, or Br | $CH_2CH_3$ | $Tc^{99m}$ |
| $CH_2CH_2CH_3$ | $CO_2A_2$, $CO_2A_4$, $CO_2A_6$, $CO_2A$ | 0 | Cl, F, or Br | $CH_2CH_3$ | $Tc^{99m}$ |
| $CH_2CH_2CH_2CH_3$ | $CO_2A_2$, $CO_2A_4$, $CO_2A_6$, $CO_2A$ | 0 | Cl, F, or Br | $CH_2CH_3$ | $Tc^{99m}$ |

*Applies when A is $A_7$

TABLE L

| Q | Z | n | X | E* | M |
|---|---|---|---|---|---|
| $CH_3$ | $COA_2$, $COA_4$, $COA_6$, $COA_7$ | 1 | Cl, F, or Br | $CH_2$ | $Tc^{99m}$ |
| $CH_2CH_3$ | $COA_2$, $COA_4$, $COA_6$, $COA_7$ | 1 | Cl, F, or Br | $CH_2$ | $Tc^{99m}$ |
| $CH_2CH_2CH_3$ | $COA_2$, $COA_4$, $COA_6$, $COA_7$ | 1 | Cl, F, or Br | $CH_2$ | $Tc^{99m}$ |
| $CH_2CH_2CH_2CH_3$ | $COA_2$, $COA_4$, $COA_6$, $COA_7$ | 1 | Cl, F, or Br | $CH_2$ | $Tc^{99m}$ |
| $CH_3$ | $COA_2$, $COA_4$, $COA_6$, $COA_7$ | 2 | Cl, F, or Br | $CH_2$ | $Tc^{99m}$ |
| $CH_2CH_3$ | $COA_2$, $COA_4$, $COA_6$, $COA_7$ | 2 | Cl, F, or Br | $CH_2$ | $Tc^{99m}$ |
| $CH_2CH_2CH_3$ | $COA_2$, $COA_4$, $COA_6$, $COA_7$ | 2 | Cl, F, or Br | $CH_2$ | $Tc^{99m}$ |
| $CH_2CH_2CH_2CH_3$ | $COA_2$, $COA_4$, $COA_6$, $COA_7$ | 2 | Cl, F, or Br | $CH_2$ | $Tc^{99m}$ |
| $CH_3$ | $COA_2$, $COA_4$, $COA_6$, $COA_7$ | 3 | Cl, F, or Br | $CH_2$ | $Tc^{99m}$ |
| $CH_2CH_3$ | $COA_2$, $COA_4$, $COA_6$, $COA_7$ | 3 | Cl, F, or Br | $CH_2$ | $Tc^{99m}$ |
| $CH_2CH_2CH_3$ | $COA_2$, $COA_4$, $COA_6$, $COA_7$ | 3 | Cl, F, or Br | $CH_2$ | $Tc^{99m}$ |
| $CH_2CH_2CH_2CH_3$ | $COA_2$, $COA_4$, $COA_6$, $COA_7$ | 3 | Cl, F, or Br | $CH_2$ | $Tc^{99m}$ |
| $CH_3$ | $COA_2$, $COA_4$, $COA_6$, $COA_7$ | 0 | Cl, F, or Br | $CH_2$ | $Tc^{99m}$ |
| $CH_2CH_3$ | $COA_2$, $COA_4$, $COA_6$, $COA_7$ | 0 | Cl, F, or Br | $CH_2$ | $Tc^{99m}$ |
| $CH_2CH_2CH_3$ | $COA_2$, $COA_4$, $COA_6$, $COA_7$ | 0 | Cl, F, or Br | $CH_2$ | $Tc^{99m}$ |
| $CH_2CH_2CH_2CH_3$ | $COA_2$, $COA_4$, $COA_6$, $COA_7$ | 0 | Cl, F, or Br | $CH_2$ | $Tc^{99m}$ |

*Applies when A is $A_7$

TABLE M

| Q | Z | n | X | E* | M |
|---|---|---|---|---|---|
| $CH_3$ | $COA_2$, $COA_4$, $COA_6$, $COA_7$ | 1 | Cl, F, or Br | $CH_2CH_3$ | $Tc^{99m}$ |
| $CH_2CH_3$ | $COA_2$, $COA_4$, $COA_6$, $COA_7$ | 1 | Cl, F, or Br | $CH_2CH_3$ | $Tc^{99m}$ |
| $CH_2CH_2CH_3$ | $COA_2$, $COA_4$, $COA_6$, $COA_7$ | 1 | Cl, F, or Br | $CH_2CH_3$ | $Tc^{99m}$ |
| $CH_2CH_2CH_2CH_3$ | $COA_2$, $COA_4$, $COA_6$, $COA_7$ | 1 | Cl, F, or Br | $CH_2CHZ$ 3 | $Tc^{99m}$ |
| $CH_3$ | $COA_2$, $COA_4$, $COA_6$, $COA_7$ | 2 | Cl, F, or Br | $CH_2CH_3$ | $Tc^{99m}$ |
| $CH_2CH_3$ | $COA_2$, $COA_4$, $COA_6$, $COA_7$ | 2 | Cl, F, or Br | $CH_2CH_3$ | $Tc^{99m}$ |
| $CH_2CH_2CH_3$ | $COA_2$, $COA_4$, $COA_6$, $COA_7$ | 2 | Cl, F, or Br | $CH_2CH_3$ | $Tc^{99m}$ |
| $CH_2CH_2CH_2CH_3$ | $COA_2$, $COA_4$, $COA_6$, $COA_7$ | 2 | Cl, F, or Br | $CH_2CH_3$ | $Tc^{99m}$ |
| $CH_3$ | $COA_2$, $COA_4$, $COA_6$, $COA_7$ | 3 | Cl, F, or Br | $CH_2CH_3$ | $Tc^{99m}$ |
| $CH_2CH_3$ | $COA_2$, $COA_4$, $COA_6$, $COA_7$ | 3 | Cl, F, or Br | $CH_2CH_3$ | $Tc^{99m}$ |
| $CH_2CH_2CH_3$ | $COA_2$, $COA_4$, $COA_6$, $COA_7$ | 3 | Cl, F, or Br | $CH_2CH_3$ | $Tc^{99m}$ |
| $CH_2CH_2CH_2CH_3$ | $COA_2$, $COA_4$, $COA_6$, $COA_7$ | 3 | Cl, F, or Br | $CH_2CH_3$ | $Tc^{99m}$ |
| $CH_3$ | $COA_2$, $COA_4$, $COA_6$, $COA_7$ | 0 | Cl, F, or Br | $CH_2CH_3$ | $Tc^{99m}$ |
| $CH_2CH_3$ | $COA_2$, $COA_4$, $COA_6$, $COA_7$ | 0 | Cl, F, or Br | $CH_2CH_3$ | $Tc^{99m}$ |
| $CH_2CH_2CH_3$ | $COA_2$, $COA_4$, $COA_6$, $COA_7$ | 0 | Cl, F, or Br | $CH_2CH_3$ | $Tc^{99m}$ |
| $CH_2CH_2CH_2CH_3$ | $COA_2$, $COA_4$, $COA_6$, $COA_7$ | 0 | Cl, F, or Br | $CH_2CH_3$ | $Tc^{99m}$ |

*Applies when A is $A_7$

TABLE N

| Q | Z | n | X | E* | M |
|---|---|---|---|---|---|
| $CH_3$ | $CH_2OA_2$, $CH_2OA_4$, $CH_2OA_6$, $CH_2OA_7$ | 1 | Cl, F, or Br | $CH_2$ | $Tc^{99m}$ |
| $CH_2CH_3$ | $CH_2OA_2$, $CH_2OA_4$, $CH_2OA_6$, $CH_2OA_7$ | 1 | Cl, F, or Br | $CH_2$ | $Tc^{99m}$ |
| $CH_2CH_2CH_3$ | $CH_2OA_2$, $CH_2OA_4$, $CH_2OA_6$, $CH_2OA_7$ | 1 | Cl, F, or Br | $CH_2$ | $Tc^{99m}$ |
| $CH_2CH_2CH_2CH_3$ | $CH_2OA_2$, $CH_2OA_4$, $CH_2OA_6$, $CH_2OA_7$ | 1 | Cl, F, or Br | $CH_2$ | $Tc^{99m}$ |
| $CH_3$ | $CH_2OA_2$, $CH_2OA_4$, $CH_2OA_6$, $CH_2OA_7$ | 2 | Cl, F, or Br | $CH_2$ | $Tc^{99m}$ |
| $CH_2CH_3$ | $CH_2OA_2$, $CH_2OA_4$, $CH_2OA_6$, $CH_2OA_7$ | 2 | Cl, F, or Br | $CH_2$ | $Tc^{99m}$ |
| $CH_2CH_2CH_3$ | $CH_2OA_2$, $CH_2OA_4$, $CH_2OA_6$, $CH_2OA_7$ | 2 | Cl, F, or Br | $CH_2$ | $Tc^{99m}$ |
| $CH_2CH_2CH_2CH_3$ | $CH_2OA_2$, $CH_2OA_4$, $CH_2OA_6$, $CH_2OA_7$ | 2 | Cl, F, or Br | $CH_2$ | $Tc^{99m}$ |
| $CH_3$ | $CH_2OA_2$, $CH_2OA_4$, $CH_2OA_6$, $CH_2OA_7$ | 3 | Cl, F, or Br | $CH_2$ | $Tc^{99m}$ |
| $CH_2CH_3$ | $CH_2OA_2$, $CH_2OA_4$, $CH_2OA_6$, $CH_2OA_7$ | 3 | Cl, F, or Br | $CH_2$ | $Tc^{99m}$ |
| $CH_2CH_2CH_3$ | $CH_2OA_2$, $CH_2OA_4$, $CH_2OA_6$, $CH_2OA_7$ | 3 | Cl, F, or Br | $CH_2$ | $Tc^{99m}$ |
| $CH_2CH_2CH_2CH_3$ | $CH_2OA_2$, $CH_2OA_4$, $CH_2OA_6$, $CH_2OA_7$ | 3 | Cl, F, or Br | $CH_2$ | $Tc^{99m}$ |
| $CH_3$ | $CH_2OA_2$, $CH_2OA_4$, $CH_2OA_6$, $CH_2OA_7$ | 0 | Cl, F, or Br | $CH_2$ | $Tc^{99m}$ |
| $CH_2CH_3$ | $CH_2OA_2$, $CH_2OA_4$, $CH_2OA_6$, $CH_2OA_7$ | 0 | Cl, F, or Br | $CH_2$ | $Tc^{99m}$ |
| $CH_2CH_2CH_3$ | $CH_2OA_2$, $CH_2OA_4$, $CH_2OA_6$, $CH_2OA_7$ | 0 | Cl, F, or Br | $CH_2$ | $Tc^{99m}$ |
| $CH_2CH_2CH_2CH_3$ | $CH_2OA_2$, $CH_2OA_4$, $CH_2OA_6$, $CH_2OA_7$ | 0 | Cl, F, or Br | $CH_2$ | $Tc^{99m}$ |

*Applies when A is $A_7$

TABLE O

| Q | Z | n | X | E* | M |
|---|---|---|---|---|---|
| $CH_3$ | $CH_2OA_2$, $CH_2OA_4$, $CH_2OA_6$, $CH_2OA_7$ | 1 | Cl, F, or Br | $CH_2CH_3$ | $Tc^{99m}$ |
| $CH_2CH_3$ | $CH_2OA_2$, $CH_2OA_4$, $CH_2OA_6$, $CH_2OA_7$ | 1 | Cl, F, or Br | $CH_2CH_3$ | $Tc^{99m}$ |
| $CH_2CH_2CH_3$ | $CH_2OA_2$, $CH_2OA_4$, $CH_2OA_6$, $CH_2OA_7$ | 1 | Cl, F, or Br | $CH_2CH_3$ | $Tc^{99m}$ |
| $CH_2CH_2CH_2CH_3$ | $CH_2OA_2$, $CH_2OA_4$, $CH_2OA_6$, $CH_2OA_7$ | 1 | Cl, F, or Br | $CH_2CH_3$ | $Tc^{99m}$ |
| $CH_3$ | $CH_2OA_2$, $CH_2OA_4$, $CH_2OA_6$, $CH_2OA_7$ | 2 | Cl, F, or Br | $CH_2CH_3$ | $Tc^{99m}$ |
| $CH_2CH_3$ | $CH_2OA_2$, $CH_2OA_4$, $CH_2OA_6$, $CH_2OA_7$ | 2 | Cl, F, or Br | $CH_2CH_3$ | $Tc^{99m}$ |
| $CH_2CH_2CH_3$ | $CH_2OA_2$, $CH_2OA_4$, $CH_2OA_6$, $CH_2OA_7$ | 2 | Cl, F, or Br | $CH_2CH_3$ | $Tc^{99m}$ |
| $CH_2CH_2CH_2CH_3$ | $CH_2OA_2$, $CH_2OA_4$, $CH_2OA_6$, $CH_2OA_7$ | 2 | Cl, F, or Br | $CH_2CH_3$ | $Tc^{99m}$ |
| $CH_3$ | $CH_2OA_2$, $CH_2OA_4$, $CH_2OA_6$, $CH_2OA_7$ | 3 | Cl, F, or Br | $CH_2CH_3$ | $Tc^{99m}$ |
| $CH_2CH_3$ | $CH_2OA_2$, $CH_2OA_4$, $CH_2OA_6$, $CH_2OA_7$ | 3 | Cl, F, or Br | $CH_2CH_3$ | $Tc^{99m}$ |
| $CH_2CH_2CH_3$ | $CH_2OA_2$, $CH_2OA_4$, $CH_2OA_6$, $CH_2OA_7$ | 3 | Cl, F, or Br | $CH_2CH_3$ | $Tc^{99m}$ |
| $CH_2CH_2CH_2CH_3$ | $CH_2OA_2$, $CH_2OA_4$, $CH_2OA_6$, $CH_2OA_7$ | 3 | Cl, F, or Br | $CH_2CH_3$ | $Tc^{99m}$ |
| $CH_3$ | $CH_2OA_2$, $CH_2OA_4$, $CH_2OA_6$, $CH_2OA_7$ | 0 | Cl, F, or Br | $CH_2CH_3$ | $Tc^{99m}$ |
| $CH_2CH_3$ | $CH_2OA_2$, $CH_2OA_4$, $CH_2OA_6$, $CH_2OA_7$ | 0 | Cl, F, or Br | $CH_2CH_3$ | $Tc^{99m}$ |
| $CH_2CH_2CH_3$ | $CH_2OA_2$, $CH_2OA_4$, $CH_2OA_6$, $CH_2OA_7$ | 0 | Cl, F, or Br | $CH_2CH_3$ | $Tc^{99m}$ |
| $CH_2CH_2CH_2CH_3$ | $CH_2OA_2$, $CH_2OA_4$, $CH_2OA_6$, $CH_2OA_7$ | 0 | Cl, F, or Br | $CH_2CH_3$ | $Tc^{99m}$ |

*Applies when A is $A_7$

TABLE P

| Q | Z | $R_1$ | n | $R_3$ | X | M |
|---|---|---|---|---|---|---|
| $A_1$, $A_3$, $A_5$, or $A_8$ | $CO_2R_1$ | $CH_3$ | 1 | H | Cl or F | $Tc^{99m}$ |
| $A_1$, $A_3$, $A_5$, or $A_8$ | $CO_2R_1$ | $CH_3$ | 1 | $CH_2CH_2CH_3$ | Cl or F | $Tc^{99m}$ |
| $A_1$, $A_3$, $A_5$, or $A_8$ | $CO_2R_1$ | $CH_3$ | 1 | methoxybenzyl | Cl or F | $Tc^{99m}$ |
| $A_1$, $A_3$, $A_5$, or $A_8$ | $CO_2R_1$ | $CH_3$ | 1 | trityl | Cl or F | $Tc^{99m}$ |
| $A_1$, $A_3$, $A_5$, or $A_8$ | $CO_2R_1$ | $CH_2CH_3$ | 1 | H | Cl or F | $Tc^{99m}$ |
| $A_1$, $A_3$, $A_5$, or $A_8$ | $CO_2R_1$ | $CH_2CH_3$ | 1 | $CH_2CH_2CH_3$ | Cl or F | $Tc^{99m}$ |
| $A_1$, $A_3$, $A_5$, or $A_8$ | $CO_2R_1$ | $CH_2CH_3$ | 1 | methoxybenzyl | Cl or F | $Tc^{99m}$ |
| $A_1$, $A_3$, $A_5$, or $A_8$ | $CO_2R_1$ | $CH_2CH_3$ | 1 | trityl | CL or F | $Tc^{99m}$ |
| $A_1$, $A_3$, $A_5$, or $A_8$ | $CO_2R_1$ | $CH_2CH_2CH_3$ | 1 | H | Cl or F | $Tc^{99m}$ |
| $A_1$, $A_3$, $A_5$, or $A_8$ | $CO_2R_1$ | $CH_2CH_2CH_3$ | 1 | $CH_2CH_2CH_3$ | Cl or F | $Tc^{99m}$ |
| $A_1$, $A_3$, $A_5$, or $A_8$ | $CO_2R_1$ | $CH_2CH_2CH_3$ | 1 | trityl | Cl or F | $Tc^{99m}$ |
| $A_1$, $A_3$, $A_5$, or $A_8$ | $CO_2R_1$ | $CH_2CH_2CH_3$ | 1 | methoxybenzyl | Cl or F | $Tc^{99m}$ |
| $A_1$, $A_3$, $A_5$, or $A_8$ | $CO_2R_1$ | $CH_2CH_2CH_2CH_3$ | 1 | methoxybenzyl | Cl or F | $Tc^{99m}$ |
| $A_1$, $A_3$, $A_5$, or $A_8$ | $CO_2R_1$ | $CH_2CH_2CH_2CH_3$ | 1 | H | Cl or F | $Tc^{99m}$ |
| $A_1$, $A_3$, $A_5$, or $A_8$ | $CO_2R_1$ | $CH_2CH_2CH_2CH_3$ | 1 | $CH_2CH_2CH_3$ | Cl or F | $Tc^{99m}$ |
| $A_1$, $A_3$, $A_5$, or $A_8$ | $CO_2R_1$ | $CH_2CH_2CH_2CH_3$ | 1 | trityl | Cl or F | $Tc^{99m}$ |
| $A_1$, $A_3$, $A_5$, or $A_8$ | $CO_2R_1$ | $CH_3$ | 2 | H | Cl or F | $Tc^{99m}$ |
| $A_1$, $A_3$, $A_5$, or $A_8$ | $CO_2R_1$ | $CH_3$ | 2 | $CH_2CH_2CH_3$ | Cl or F | $Tc^{99m}$ |
| $A_1$, $A_3$, $A_5$, or $A_8$ | $CO_2R_1$ | $CH_3$ | 2 | methoxybenzyl | Cl or F | $Tc^{99m}$ |
| $A_1$, $A_3$, $A_5$, or $A_8$ | $CO_2R_1$ | $CH_3$ | 2 | trityl | Cl or F | $Tc^{99m}$ |
| $A_1$, $A_3$, $A_5$, or $A_8$ | $CO_2R_1$ | $CH_2CH_3$ | 2 | methoxybenzyl | Cl or F | $Tc^{99m}$ |
| $A_1$, $A_3$, $A_5$, or $A_8$ | $CO_2R_1$ | $CH_2CH_3$ | 2 | trityl | Cl or F | $Tc^{99m}$ |
| $A_1$, $A_3$, $A_5$, or $A_8$ | $CO_2R_1$ | $CH_2CH_3$ | 2 | H | Cl or F | $Tc^{99m}$ |
| $A_1$, $A_3$, $A_5$, or $A_8$ | $CO_2R_1$ | $CH_2CH_3$ | 2 | $CH_2CH_2CH_3$ | Cl or F | $Tc^{99m}$ |
| $A_1$, $A_3$, $A_5$, or $A_8$ | $CO_2R_1$ | $CH_2CH_2CH_3$ | 2 | H | Cl or F | $Tc^{99m}$ |
| $A_1$, $A_3$, $A_5$, or $A_8$ | $CO_2R_1$ | $CH_2CH_2CH_3$ | 2 | $CH_2CH_2CH_3$ | Cl or F | $Tc^{99m}$ |
| $A_1$, $A_3$, $A_5$, or $A_8$ | $CO_2R_1$ | $CH_2CH_2CH_3$ | 2 | methoxybenzyl | Cl or F | $Tc^{99m}$ |
| $A_1$, $A_3$, $A_5$, or $A_8$ | $CO_2R_1$ | $CH_2CH_2CH_3$ | 2 | trityl | Cl or F | $Tc^{99m}$ |
| $A_1$, $A_3$, $A_5$, or $A_8$ | $CO_2R_1$ | $CH_2CH_2CH_2CH_3$ | 2 | methoxybenzyl | Cl or F | $Tc^{99m}$ |
| $A_1$, $A_3$, $A_5$, or $A_8$ | $CO_2R_1$ | $CH_2CH_2CH_2CH_3$ | 2 | $CH_2CH_2CH_3$ | Cl or F | $Tc^{99m}$ |
| $A_1$, $A_3$, $A_5$, or $A_8$ | $CO_2R_1$ | $CH_2CH_2CH_2CH_3$ | 2 | H | Cl or F | $Tc^{99m}$ |
| $A_1$, $A_3$, $A_5$, or $A_8$ | $CO_2R_1$ | $CH_2CH_2CH_2CH_3$ | 2 | trityl | Cl or F | $Tc^{99m}$ |

TABLE Q

| Q | Z | $R_1$ | n | $R_3$ | X | M |
|---|---|---|---|---|---|---|
| $A_1$, $A_3$, $A_5$, or $A_8$ | $COR_1$ | $CH_3$ | 1 | H | Cl or F | $Tc^{99m}$ |
| $A_1$, $A_3$, $A_5$, or $A_8$ | $COR_1$ | $CH_3$ | 1 | $CH_2CH_2CH_3$ | Cl or F | $Tc^{99m}$ |
| $A_1$, $A_3$, $A_5$, or $A_8$ | $COR_1$ | $CH_3$ | 1 | methoxybenzyl | Cl or F | $Tc^{99m}$ |
| $A_1$, $A_3$, $A_5$, or $A_8$ | $COR_1$ | $CH_3$ | 1 | trityl | Cl or F | $Tc^{99m}$ |
| $A_1$, $A_3$, $A_5$, or $A_8$ | $COR_1$ | $CH_2CH_3$ | 1 | methoxybenzyl | Cl or F | $Tc^{99m}$ |
| $A_1$, $A_3$, $A_5$, or $A_8$ | $COR_1$ | $CH_2CH_3$ | 1 | trityl | Cl or F | $Tc^{99m}$ |
| $A_1$, $A_3$, $A_5$, or $A_8$ | $COR_1$ | $CH_2CH_3$ | 1 | H | Cl or F | $Tc^{99m}$ |
| $A_1$, $A_3$, $A_5$, or $A_8$ | $COR_1$ | $CH_2CH_3$ | 1 | $CH_2CH_2CH_3$ | Cl or F | $Tc^{99m}$ |
| $A_1$, $A_3$, $A_5$, or $A_8$ | $COR_1$ | $CH_2CH_2CH_3$ | 1 | H | Cl or F | $Tc^{99m}$ |
| $A_1$, $A_3$, $A_5$, or $A_8$ | $COR_1$ | $CH_2CH_2CH_3$ | 1 | $CH_2CH_2CH_3$ | Cl or F | $Tc^{99m}$ |
| $A_1$, $A_3$, $A_5$, or $A_8$ | $COR_1$ | $CH_2CH_2CH_3$ | 1 | methoxybenzyl | Cl or F | $Tc^{99m}$ |
| $A_1$, $A_3$, $A_5$, or $A_8$ | $COR_1$ | $CH_2CH_2CH_3$ | 1 | trityl | Cl or F | $Tc^{99m}$ |
| $A_1$, $A_3$, $A_5$, or $A_8$ | $COR_1$ | $CH_2CH_2CH_2CH_3$ | 1 | methoxybenzyl | Cl or F | $Tc^{99m}$ |
| $A_1$, $A_3$, $A_5$, or $A_8$ | $COR_1$ | $CH_2CH_2CH_2CH_3$ | 1 | $CH_2CH_2CH_3$ | Cl or F | |
| $A_1$, $A_3$, $A_5$, or $A_8$ | $COR_1$ | $CH_2CH_2CH_2CH_3$ | 1 | H | Cl or F | |
| $A_1$, $A_3$, $A_5$, or $A_8$ | $COR_1$ | $CH_2CH_2CH_2CH_3$ | 1 | trityl | Cl or F | $Tc^{99m}$ |
| $A_1$, $A_3$, $A_5$, or $A_8$ | $COR_1$ | $CH_3$ | 2 | H | Cl or F | $Tc^{99m}$ |
| $A_1$, $A_3$, $A_5$, or $A_8$ | $COR_1$ | $CH_3$ | 2 | $CH_2CH_2CH_3$ | Cl or F | $Tc^{99m}$ |
| $A_1$, $A_3$, $A_5$, or $A_8$ | $COR_1$ | $CH_3$ | 2 | methoxybenzyl | Cl or F | $Tc^{99m}$ |
| $A_1$, $A_3$, $A_5$, or $A_8$ | $COR_1$ | $CH_3$ | 2 | trityl | Cl or F | $Tc^{99m}$ |
| $A_1$, $A_3$, $A_5$, or $A_8$ | $COR_1$ | $CH_2CH_3$ | 2 | methoxybenzyl | Cl or F | $Tc^{99m}$ |
| $A_1$, $A_3$, $A_5$, or $A_8$ | $COR_1$ | $CH_2CH_3$ | 2 | trityl | Cl or F | $Tc^{99m}$ |
| $A_1$, $A_3$, $A_5$, or $A_8$ | $COR_1$ | $CH_2CH_3$ | 2 | $CH_2CH_2CH_3$ | Cl or F | $Tc^{99m}$ |
| $A_1$, $A_3$, $A_5$, or $A_8$ | $COR_1$ | $CH_2CH_3$ | 2 | H | Cl or F | $Tc^{99m}$ |
| $A_1$, $A_3$, $A_5$, or $A_8$ | $COR_1$ | $CH_2CH_2CH_3$ | 2 | H | Cl or F | $Tc^{99m}$ |
| $A_1$, $A_3$, $A_5$, or $A_8$ | $COR_1$ | $CH_2CH_2CH_3$ | 2 | $CH_2CH_2CH_3$ | Cl or F | $Tc^{99m}$ |
| $A_1$, $A_3$, $A_5$, or $A_8$ | $COR_1$ | $CH_2CH_2CH_3$ | 2 | trityl | Cl or F | $Tc^{99m}$ |
| $A_1$, $A_3$, $A_5$, or $A_8$ | $COR_1$ | $CH_2CH_2CH_3$ | 2 | methoxybenzyl | Cl or F | $Tc^{99m}$ |
| $A_1$, $A_3$, $A_5$, or $A_8$ | $COR_1$ | $CH_2CH_2CH_2CH_3$ | 2 | methoxybenzyl | Cl or F | $Tc^{99m}$ |
| $A_1$, $A_3$, $A_5$, or $A_8$ | $COR_1$ | $CH_2CH_2CH_2CH_3$ | 2 | $CH_2CH_2CH_3$ | Cl or F | $Tc^{99m}$ |
| $A_1$, $A_3$, $A_5$, or $A_8$ | $COR_1$ | $CH_2CH_2CH_2CH_3$ | 2 | H | Cl or F | $Tc^{99m}$ |
| $A_1$, $A_3$, $A_5$, or $A_8$ | $COR_1$ | $CH_2CH_2CH_2CH_3$ | 2 | trityl | Cl or F | $Tc^{99m}$ |

TABLE R

| Q | Z | $R_1$ | n | $R_3$ | X | M |
|---|---|---|---|---|---|---|
| $A_1$, $A_3$, $A_5$, or $A_8$ | $COR_1$ | $CH_3$ | 3 | H | Cl or F | $Tc^{99m}$ |
| $A_1$, $A_3$, $A_5$, or $A_8$ | $COR_1$ | $CH_3$ | 3 | $CH_2CH_2CH_3$ | Cl or F | $Tc^{99m}$ |
| $A_1$, $A_3$, $A_5$, or $A_8$ | $COR_1$ | $CH_3$ | 3 | methoxybenzyl | Cl or F | $Tc^{99m}$ |
| $A_1$, $A_3$, $A_5$, or $A_8$ | $COR_1$ | $CH_3$ | 3 | trityl | Cl or F | $Tc^{99m}$ |
| $A_1$, $A_3$, $A_5$, or $A_8$ | $COR_1$ | $CH_2CH_3$ | 3 | methoxybenzyl | Cl or F | $Tc^{99m}$ |
| $A_1$, $A_3$, $A_5$, or $A_8$ | $COR_1$ | $CH_2CH_3$ | 3 | trityl | Cl or F | $Tc^{99m}$ |
| $A_1$, $A_3$, $A_5$, or $A_8$ | $COR_1$ | $CH_2CH_3$ | 3 | $CH_2CH_2CH_3$ | Cl or F | $Tc^{99m}$ |
| $A_1$, $A_3$, $A_5$, or $A_8$ | $COR_1$ | $CH_2CH_3$ | 3 | H | Cl or F | $Tc^{99m}$ |
| $A_1$, $A_3$, $A_5$, or $A_8$ | $COR_1$ | $CH_2CH_2CH_3$ | 3 | H | Cl or F | $Tc^{99m}$ |
| $A_1$, $A_3$, $A_5$, or $A_8$ | $COR_1$ | $CH_2CH_2CH_3$ | 3 | $CH_2CH_2CH_3$ | Cl or F | $Tc^{99m}$ |
| $A_1$, $A_3$, $A_5$, or $A_8$ | $COR_1$ | $CH_2CH_2CH_3$ | 3 | methoxybenzyl | Cl or F | $Tc^{99m}$ |
| $A_1$, $A_3$, $A_5$, or $A_8$ | $COR_1$ | $CH_2CH_2CH_3$ | 3 | trityl | Cl or F | $Tc^{99m}$ |
| $A_1$, $A_3$, $A_5$, or $A_8$ | $COR_1$ | $CH_2CH_2CH_2CH_3$ | 3 | methoxybenzyl | Cl or F | $Tc^{99m}$ |
| $A_1$, $A_3$, $A_5$, or $A_8$ | $COR_1$ | $CH_2CH_2CH_2CH_3$ | 3 | H | Cl or F | $Tc^{99m}$ |
| $A_1$, $A_3$, $A_5$, or $A_8$ | $COR_1$ | $CH_2CH_2CH_2CH_3$ | 3 | $CH_2CH_2CH_3$ | Cl or F | $Tc^{99m}$ |
| $A_1$, $A_3$, $A_5$, or $A_8$ | $COR_1$ | $CH_2CH_2CH_2CH_3$ | 3 | trityl | Cl or F | $Tc^{99m}$ |
| $A_1$, $A_3$, $A_5$, or $A_8$ | $COR_1$ | $CH_3$ | 0 | H | Cl or F | $Tc^{99m}$ |
| $A_1$, $A_3$, $A_5$, or $A_8$ | $COR_1$ | $CH_3$ | 0 | $CH_2CH_2CH_3$ | Cl or F | $Tc^{99m}$ |
| $A_1$, $A_3$, $A_5$, or $A_8$ | $COR_1$ | $CH_3$ | 0 | methoxybenzyl | Cl or F | $Tc^{99m}$ |
| $A_1$, $A_3$, $A_5$, or $A_8$ | $COR_1$ | $CH_3$ | 0 | trityl | Cl or F | $Tc^{99m}$ |
| $A_1$, $A_3$, $A_5$, or $A_8$ | $COR_1$ | $CH_2CH_3$ | 0 | methoxybenzyl | Cl or F | $Tc^{99m}$ |
| $A_1$, $A_3$, $A_5$, or $A_8$ | $COR_1$ | $CH_2CH_3$ | 0 | trityl | Cl or F | $Tc^{99m}$ |
| $A_1$, $A_3$, $A_5$, or $A_8$ | $COR_1$ | $CH_2CH_3$ | 0 | $CH_2CH_2CH_3$ | Cl or F | $Tc^{99m}$ |
| $A_1$, $A_3$, $A_5$, or $A_8$ | $COR_1$ | $CH_2CH_3$ | 0 | H | Cl or F | $Tc^{99m}$ |
| $A_1$, $A_3$, $A_5$, or $A_8$ | $COR_1$ | $CH_2CH_2CH_3$ | 0 | H | Cl or F | $Tc^{99m}$ |
| $A_1$, $A_3$, $A_5$, or $A_8$ | $COR_1$ | $CH_2CH_2CH_3$ | 0 | $CH_2CH_2CH_3$ | Cl or F | $Tc^{99m}$ |
| $A_1$, $A_3$, $A_5$, or $A_8$ | $COR_1$ | $CH_2CH_2CH_3$ | 0 | methoxybenzyl | Cl or F | $Tc^{99m}$ |
| $A_1$, $A_3$, $A_5$, or $A_8$ | $COR_1$ | $CH_2CH_2CH_3$ | 0 | trityl | Cl or F | $Tc^{99m}$ |
| $A_1$, $A_3$, $A_5$, or $A_8$ | $COR_1$ | $CH_2CH_2CH_2CH_3$ | 0 | methoxybenzyl | Cl or F | $Tc^{99m}$ |
| $A_1$, $A_3$, $A_5$, or $A_8$ | $COR_1$ | $CH_2CH_2CH_2CH_3$ | 0 | H | Cl or F | $Tc^{99m}$ |
| $A_1$, $A_3$, $A_5$, or $A_8$ | $COR_1$ | $CH_2CH_2CH_2CH_3$ | 0 | $CH_2CH_2CH_3$ | Cl or F | $Tc^{99m}$ |
| $A_1$, $A_3$, $A_5$, or $A_8$ | $COR_1$ | $CH_2CH_2CH_2CH_3$ | 0 | trityl | Cl or F | $Tc^{99m}$ |

EXAMPLES

General Experimental For Examples 1 to 13

Reagents used in the syntheses were purchased from Aldrich (Milwaukee, Wis.) or Fluka (Ronkonkoma, N.Y.), and were used without further purification unless otherwise indicated. Anhydrous $Na_2SO_4$ was used as a drying agent. Reaction yields are reported without attempts at optimization. Thin layer chromatography was performed on EM Science (Gibbstown, N.J.) precoated (0.2 mm) silica gel 60 plates, and the spots were detected with iodine vapor and/or UV light. Silica gel 60 (70–230 mesh), obtained from EM Science (Gibbstown, N.J.), was used for column chromatography. 1H NMR spectra were obtained on a Bruker spectrometer (Bruker AC 300). All samples prepared for NMR analysis were dissolved in $CDCl_3$, purchased from Aldrich. Chemical shifts are reported as d values with chloroform or TMS as the internal reference. Coupling constants are reported in Hz. The multiplicity is defined by s (singlet), d (doublet), t (triplet), brs (broad signal), dt (doublet of triplet) and m (multiplet). IR spectra were recorded with a Mattson Polaris FT-IR spectrometer and are reported in cm-1. Melting points were determined on a Meltemp apparatus (Cambridge, Mass.), and are uncorrected. Elemental analyses were performed by Atlantic Microlabs (Norcross, Ga.). High resolution mass spectrometry was performed by the Nebraska Center for Mass Spectroscopy, University of Nebraska (Lincoln, Nebr.). The compound reference numbers used in the examples and Tables correspond to the compounds depicted in the reaction schemes.

Example 1

Preparation Of Compounds 1.5a And 1.5b

Oxalyl chloride (2 mmol, 1 mL from 2M solution in $CH_2Cl_2$) was added to tropane acid 1.3 (1 mmol) in $CH_2Cl_2$ (10 mL) at room temperature under $N_2$. The resulting mixture was stirred for 1.5 hours and concentrated in vacuo at 30° C. to obtain a viscous oil which was dried in a vacuum for 15 minutes. The acid chloride obtained was dissolved in $CH_2Cl_2$ (10 mnL) and cooled to −10° C. and amine 1.4 (1 mmol, 470 mg) in $CH_2Cl_2$ (10 mL) was added, followed by Et3N (3 mmol, 0.42 mL), under $N_2$. The resulting solution was stirred at room temperature for 6 hours. Water (20 mL) was then added to the reaction mixture and the product was extracted into $CH_2Cl_2$ (3×20 mL). $CH_2Cl_2$ layers were combined, dried ($Na_2SO_4$) and concentrated in vacuo to obtain an oil that was chromatographed on silica ($EtOAc:MeOH:NH_4OH$ 8.5:1:0.5) to obtain the title compound as a viscous oil.

1.5a: yield 59%; IR 1640 cm−1; 1H NMR ($CDCl_3$) d 1.59 (m, 3H), 2.05–2.5 (m, 9H), 2.7–2.9 (m, 4H), 3.1–3.2 (m, 4H), 3.3–3.5 (m, 3H), 3.5 and 3.6 (s, 2H each), 3.72 and 3.74 (s, 3H each), 6.36 (brs, 1H), 6.8 (d, 2H, J=6 Hz), 6.84 (d, 2H, J=6 Hz), 7.02–7.21 (m, 8H).

1.5b: yield 66%; IR 1636 cm−1; 1H NMR ($CDCl_3$) d 1.5–1.7 (m, 3H), 2.05–2.5 (m, 9H), 2.7–2.9 (m, 4H), 3.1–3.2 (m, 4H), 3.3–3.5 (m, 3H), 3.5 and 3.6 (s, 2H each), 3.72 and 3.74 (s, 3H each), 6.4 (brs, 1H), 6.8 −6.9 (m, 6H), 7.02–7.25 (m, 6H).

Example 2

Preparation Of Compounds 1.6a And 1.6b $BH_3 \cdot THF$ (5 mmol, 5 mL of 1M solution in THF) was added to compound 1.5 (1 mmol) in THF (10 mL) under $N_2$ and the resulting mixture was heated at reflux for 12 hours. The reaction mixture was cooled to 0° C. and 1N HCl was added dropwise until there was no more gas evolution, then the mixture was concentrated in vacuo. 1N HCl (10 mL) was added to the viscous oil obtained and the resulting mixture was stirred at 50° C. for 30 minutes. The reaction mixture was cooled to 0° C. and basified with concentrated $NH_4OH$. The product was extracted into $CH_2Cl_2$ and purified by chromatography on silica ($EtOAc:MeOH:NH_4OH$ 8.5:1:0.5) to give the title compounds.

1.6a: yield 19%; IR 1661 cm−1; 1H NMR (CDCl3) d 1.4–1.9 (m, 5H), 2.05–3.1 (m, 18H), 3.0–3.15 (m, 1H), 3.26–3.28 (m, 1H), 3.48–3.51 (m, 1H), 3.67 and 3.681 (s, 2H each), 3.72 and 3.73 (s, 3H each), 6.8 (m, 4H), 7.02–7.21 (m, 8H).

1.6b: yield 23%; IR 1659 cm-1; 1H NMR (CDCl3) d 1.4–1.9 (m, 5H), 2.05–3.1 (m, 18H), 3.0–3.15 (m, 1H), 3.26–3.28 (m, 1H), 3.48–3.51 (m, 1H), 3.57 and 3.61 (s, 2H each), 3.72 and 3.73 (s, 3H each), 6.75 −6.8 (m, 4H), 6.87–6.90 and 6.99–7.04 (m, 2H each), 7.12–7.18 (m, 4H).

Example 3

Preparation Of Compounds 1.11a and 1.11b

Oxalyl chloride (2 mmol, 1 mL from 2M solution in $CH_2Cl_2$) was added to tropane acid 1.3 (1 mmol) in $CH_2Cl_2$ (10 mL) at room temperature under $N_2$. The resulting mixture was stirred for 1.5 h and concentrated in vacuo at 30° C. to obtain a viscous oil, which was dried in a vacuum for 15 minutes. The acid chloride obtained was dissolved in $CH_2Cl_2$ (10 mL) and cooled to −10° C. and amine 1.9 (1 mmol, 197 mg) in $CH_2Cl_2$ (10 mL) was added, followed by $Et_3N$ (2 mmol, 0.28 mL) under $N_2$. The resulting solution was stirred at room temperature for 6 hours. Water (20 mL) was then added to the reaction mixture and the product was extracted into $CH_2Cl_2$ (3×20 mL). The $CH_2Cl_2$ layers were combined, dried ($Na_2SO_4$) and concentrated in vacuo to produce an oil that was chromatographed on silica ($EtOAc:MeOH:NH_4OH$ 8.5:1:0.5) to obtain the title compound as a viscous oil.

1.11a: yield 63%; IR 1656 cm−1; 1H NMR ($CDCl_3$) d 1.55–1.78 (m, 3H), 2.05–2.6 (m, 9H), 3.1–3.4 (m, 5H), 3.69 (s, 2H), 3.79 (s, 3H), 6.84 (d, 2H, J=6 Hz), 7.09 (d, 2H, J=6 Hz), 7.18 (d, 2H, J=6 Hz), 7.24 (d, 2H, J=6 Hz), 9.8 (brs, 1H).

1.11b: yield 59%; IR 1653 cm−1; 1H NMR ($CDCl_3$) d 1.59–1.76 (m, 3H), 1.97–2.4 (m, 6H), 2.4 −2.5 (m, 3H), 3.09 (m, 1H), 3.2–3.38 (m, 4H), 3.68 (s, 2H), 3.78 (s, 3H), 6.8–6.9 (m, 4H), 7.08–7.13 (m, 2H), 7.2 (d, 2H, J=10 Hz), 9.8 (brs, 1H).

Example 4

Preparation Of Compounds 1.13a and 1.13b $BH_3 \cdot THF$ (5 mmol, 5 mL of 1M solution in THF) was added to compound 1.11 (1 mmol) in THF (10 mL) under $N_2$ and the resulting mixture was heated at reflux for 12 hours. The reaction mixture was cooled to 0° C. and 1N HCl was added dropwise until there was no more gas evolution, then the mixture was concentrated in vacuo. 1N HCl (10 mL) was added to the viscous oil obtained and the resulting mixture was stirred at 90° C. for 30 minutes. The solution was then cooled to 0 (C and basified with conc. $NH_4OH$. The product was extracted into CH2Cl2 and purified by chromatography on silica ($EtOAc:MeOH:NH_4OH$ 8.5:1:0.5) to give the title compound.

1.13a: yield 79%; IR 1608 cm−1; 1H NMR ($CDCl_3$) d 1.5–1.8 (m, 5H), 2.05–2.2 (m, 4H), 2.23 (s, 3H), 2.34–2.39 (m, 2H), 2.47–2.52 (m, 2H), 2.65 (dd, 1H, J1=5.3, J2=7.8), 3.03 (td, 1H, J1=4, J2=8.8), 3.25 (m, 2H), 3.5 (s, 2H), 3.78 (s, 3H), 6.84 (d, 2H, J=6 Hz), 7.09 (d, 2H, J=6 Hz), 7.18 (d, 2H, J=6 Hz),7.24 (d, 2H, J=6 Hz).

1.13b: yield 83%; IR 1600 cm−1; 1H NMR ($CDCl_3$) d 1.59–1.76 (m, 3H), 1.97–2.4 (m, 6H), 2.4–2.5 (m, 3H), 3.09 (m, 1H), 3.2–3.38 (m, 4H), 3.68 (s, 2H), 3.78 (s, 3H), 6.8–6.9 (m, 4H), 7.08–7.13 (m, 2H), 7.2 (d, 2H, J=10 Hz).

Example 5

Preparation Of Compounds 1.14a and 1.14b

Amine 1.9 (12.5 mmol, 2.46 g) in $CH_2Cl_2$ (15 mL) was added dropwise to a stirred solution of chloroacetyl chloride (12.5 mmol, 1 mL) in $CH_2Cl_2$ (15 mL), followed by $Et_3N$ (12.5 mmol, 1.7 mL) at −78° C. under $N_2$. The reaction mixture was allowed to warm to room temperature and stirred for 1 hours. Water (20 mL) was then added and the organic layer was separated and washed with 1N HCl (20 mL), brine (20 mL) and water (20 mL). The organic layer was concentrated in vacuo and dried in vacuo for 30 minutes. The oil was dissolved in EtOAc (50 mL) and hexane (100 mL). The turbid solution obtained was concentrated to half the volume and stored in a freezer for 4 hours. The solid formed was collected by suction filtration to give compound 1.12, which was used for further reactions without additional purification.

Amine 1.13 (1 mmol), chloro compound 1.12 (2 mmol, 548 mg) and $Et_3N$ (2 mmol, 0.28 mL) in acetonitrile (10 mL) were heated at reflux for 24 hours. The reaction mixture was concentrated in vacuo and the product was partitioned between water (20 mL) and $CH_2Cl_2$ (20 mL). The oil obtained by concentrating the organic phase was chromatographed on silica (2% $MeOH:CH_2Cl_2$ and 10% $MeOH:CH_2Cl_2$) to produce the title compound as a yellow oil.

1.14a: yield 53%; IR 1654 cm−1; 1H NMR ($CDCl_3$) d 1.4–1.8 (m, 5H), 2.05–2.9 (m, 14H), 2.92–3.5 (m, 7H), 3.52 (s, 2H), 3.95 (s, 2H), 3.76 (s, 6H), 6.8–6.85 (m, 4H), 6.9 (d, 2H, J=6 Hz), 7.15–7.25 (m, 6H), 8.4 (brs, 1H).

1.14b: yield 66%; IR 1650 cm−1; 1H NMR ($CDCl_3$) d, 1.38–1.76 (m, 5H), 2.0–2.81 (m, 14H), 2.88–3.46 (m, 7H), 3.58 (s, 2H), 3.68 (s, 2H), 3.77 (s, 6H), 6.79–6.85 (m, 4H), 6.9–7.03 (m, 2H), 7.18–7.25 (m, 4H), 8.4 (brs, 1H).

Example 6

Preparation Of Compounds 1.15a and 1.15b

LAH (1.5 eq) was added to a solution of compound 1.14 (1 mmol) in THF (10 mL) under $N_2$ and the resulting mixture was heated at reflux for 12 hours. Usual work up, followed by chromatography of the resulting product on a chromatotrone ($EtOAc:MeOH:NH_4OH$ 8.5:1:0.5), gave the title compound.

1.15a: yield 63%. IR 1609 cm−1; 1H NMR ($CDCl_3$) d, 1.5–1.8 (m, 5H), 2.05–2.3 (m, 5H), 2.3 (s, 3H), 2.3–2.6 (m, 7H), 2.7–2.9 (m, 5H), 3.1 (td, 1H, J1=4, J2=8.8), 3.35–3.45 (m, 2H), 3.59 (s, 2H), 3.65–3.7 (m, 2H), 3.76 (s, 6H), 6.8–6.85 (m, 4H), 7.15–7.25 (m, 8H).

1.15b: yield 53%. IR 1603 cm−1; 1H NMR ($CDCl_3$) d, 1.4–1.7 (m, 5H), 1.95–2.29 (m, 5H), 2.25–2 (m, 10H), 2.7–2.9 (m, 5H), 3.0 (td, 1H, J1=4, J2=8.8), 3.2 (m, 1H), 3.35 (m, 1H), 3.6 and 3.65 (s, 2H each), 3.7 and 3.77 (s, 3H each), 6.7–6.8 (m, 4H), 6.9–6.96 and 7.01–7.06 (m, 2H each), 7.16–7.22 (m, 4H).

Example 7

General procedure for compounds 1.7, 1.16 and 1.17

Substrate 1.6, 1.14 or 1.15 (1 mmol) was dissolved in TFA (7.5 mL) and anisole (0.25 mL) at 0° C. and $Hg(OAc)_2$ (636 mg, 2 mmol) was added. The resulting mixture was stirred for 30 min and concentrated in vacuo to obtain a viscous oil which was dried in vacuo for 30 minutes. Dry ether (10 mL) was then added to the above oil and the resulting suspension was sonicated for 5 minutes. The colorless solid that formed was collected by suction filtration, dried in vacuo for 20 minutes and dissolved in absolute EtOH (10 mL). $H_2S$ gas was passed through the solution for 20 minutes and the reaction mixture was filtered through a pad of celite. The filtrate was concentrated in vacuo to obtain the trifluoroacetate salt of the title compound, which was used for further reactions without additional purification.

Example 8

Preparation of 2b-{oxo[N,N'-bis-(2'-mercaptoethyl)-ethylenediaminato)]rhenium (V)-methylamino}-3b-(4-chlorophenyl)tropane (1.22)

A solution of compound 1.16a (428 mg, 1 mmol) in MeOH (10 mL) was added to a solution of $Bu_4NReOCl_4$ (588 mg, 1 mmol) in MeOH (2 mL) under $N_2$ at 0° C. $Et_3N$ (0.5 mL, 4 mmol) was then added, and the resulting mixture was stirred at room temperature for 12 hours. The reaction mixture was concentrated in vacuo. The residue obtained was chromatographed on silica ($EtOAc:MeOH:NH_4OH$ 9.5:0.4:0.1) to obtain a purple solid, which was recrystallized ($MeOH:CH_2Cl_2$) to give pinkish needles. Yield 43%; mp 158 (C; IR (Kbr) 967 cm-1.

Example 9

Radiolabeling with Tc-99m

A sample of ligand (1.7a, 1.7b, 1.16a, 1.16b or 1.17; 0.2–0.4 $\mu$mol) was dissolved in 100 $\mu$L EtOH and 100 $\mu$L HCl (1 N). 500 $\mu$L HCl (1 N) and 1 mL Sn-glucoheptonate solution (containing 136 $\mu$g $SnCl_2$ and 200 $\mu$g Na-glucoheptonate, pH 6.67) and 50 $\mu$L EDTA solution (0.1 N) were successively added. [$^{99m}$Tc]Pertechnetate (100–200 $\mu$L; ranging from 1–20 mCi) saline solution was then added. The reaction was heated for 30 minutes at 100° C., cooled to room temperature and neutralized with a sat. $NaHCO_3$ solution. After extracting the complex from the aqueous reaction medium with ethyl acetate (1×3 mL, 2×1.5 mL) and passing it through a small column of $Na_2SO_4$, ethyl acetate was removed under a flow of $N_2$. The residue was dissolved in 200 $\mu$L EtOH and purified by HPLC (PRP-1 column, 250×4.1 mm, $CH_3CN$/3,3-dimethylglutarate buffer, 5 mM, pH 7, volume ratio 8:2, flow rate 1 mL/min). The retention times for the mixtures of 1.19a were 10.5 to 11.5 minutes (radiochemical yield 88%, radiochemical purity >98%). All the complexes displayed stability at 4 and 24 hours after preparation. Little change in radiochemical purity was observed. Identical labeling and HPLC conditions were used for the preparation of mixtures of 1.19b, 1.20a, and 1.20b (retention times of 10.6 and 12, 9.4 and 10.1, 8.0 and 8.2 and 7.8 and 8.9 minutes respectively) with radiochemical yields of 70, 88 and 82%, respectively, and radiochemical purities of >98%. For 21, the radiochemical yield was 80%, with a purity of 97% (PRP-1 column, $CH_3CN$/3,3-dimethylglutarate buffer, 5 mM, pH 7, vol. ratio 6:4).

Example 10

Evaluation

10a. Partition Coefficients

Partition coefficients were measured by mixing each Tc-99m compound with 3 g each of 1-octanol and buffer (pH 7.0 or 7.4, 0.1 M phosphate) in a test tube. The test tube was vortexed for 3 minutes at room temperature, then centrifuged for 5 minutes. Two weighed samples (0.5 g each) from the 1-octanol and buffer layers were counted in a well counter. The partition coefficient was determined by calculating the ratio of cpm/g of octanol to that of buffer. Samples from the octanol layer were repartitioned until consistent partition coefficient values were obtained. The measurement was repeated 3 times.

10b. Biodistribution in Rats

Male Sprague-Dawley rats (225–300 g) allowed free access to food and water were used for in vivo biodistribution studies. Kung, 1984, supra; Kung, 1985, supra. While under ether anesthesia, 0.2 mL of a saline solution containing 1.19a, 1.19b, 1.20a, 1.20b or 1.21 (50–100 μCi) was injected directly into the femoral vein of rats, and the rats were sacrificed by cardiac excision at various time points post-injection. The organs of interest were removed and weighed, and the radioactivity was counted with an automatic gamma counter (Packard 5000). The percentage dose per organ was calculated by a comparison of the tissue counts to suitably diluted aliquots of the injected material. Total activities of blood and muscle were calculated under the assumption that they were 7% and 40% of the total body weight, respectively.

Regional brain distribution in rats was obtained after an injection of 1.19a, 1.19b, 1.20a, 1.20b or 1.21. Samples from different brain regions (cortex, striatum, hippocampus, and cerebellum) were dissected, weighed and counted, and the percentage dose per gram of sample was calculated by comparing the sample counts with the count of the diluted initial dose. The uptake ratio of each region was obtained by dividing the percentage dose per gram of that region by that of the cerebellum. For blocking studies, rats were injected with either β-CIT or haloperidol (iv, 1 mg/Kg) 5 min prior to injection of 1.19a. The rats were dissected and brain tissue samples were counted as described above. The specific uptake of the compound was expressed as ratio of ST/CB (% dose/g of striatum divided by the same of cerebellum).

10c. SPECT and MRI Imaging in a Baboon

A baboon (~15 kg) was the subject of a SPECT imaging study. Prior to imaging, the animal was fasted, immobilized with ketamine (10–20 mg/kg, i.m.) and xylazine (2–3 mg/kg, i.m.), intubated and maintained on a 1.5–2.0% isofluorane/98.5% oxygen mixture (flow rate of 200–500 cc/min). The animal was injected with glycopyrrolate (10 μg/kg, s.c.), an anticholinergic drug that does not cross the blood-brain barrier, in order to decrease digestive and respiratory secretions. Body temperature was maintained using a hot water circulating heating pad and was monitored with a rectal thermometer. The animal's head was immobilized using a vacuum-packed bean-bag device that hardens upon evacuation when molded around the head. No-carrier-added [$^{99m}$Tc]TRODAT-1 (1.19a; 9 mCi) was administered as an intravenous bolus in the saphenous vein of the baboon. Immediately after injection, sequential 5 minute per frame dynamic SPECT scans were acquired on a triple-headed Picker Prism 3000 camera (FWHM: 7 mm) equipped with fan beam collimators for 2 hours. The acquisition parameters were a 20% energy window at 140 KeV, 120 projection angles over 360 degrees, a 128×128 matrix, and a zoom factor of 1.78 in a slice thickness of 2 mm. The projection data was reconstructed with a count dependent 3-D Wiener filter. Chang's first order correction method was used to compensate for attenuation. Magnetic resonance images (MRI) of the baboon brain were acquired with a 1.5 Tesla machine (GE Medical Systems, Milwaukee, Wis.). The spoiled GRASS acquisition parameters included a repetition time (TR) of 5 msec and a flip angle of 35 degrees, which produced 1 mm thick slices. The data were reinterpolated in 256×256 matrices with cubic voxels of 2 mm per side to match the SPECT images. The SPECT images of [99mTc] TRODAT-1 (1.19a) at 60–90 minutes post-injection were summed and reformatted to match the MRI scans. Both data sets were imported into a locally developed software package for co-registration. The program simultaneously displayed three orthogonal views of either the MRI, the SPECT scans (coronal, transaxial and sagital views), or the fused images of both sets.

Example 11

Figure 2:
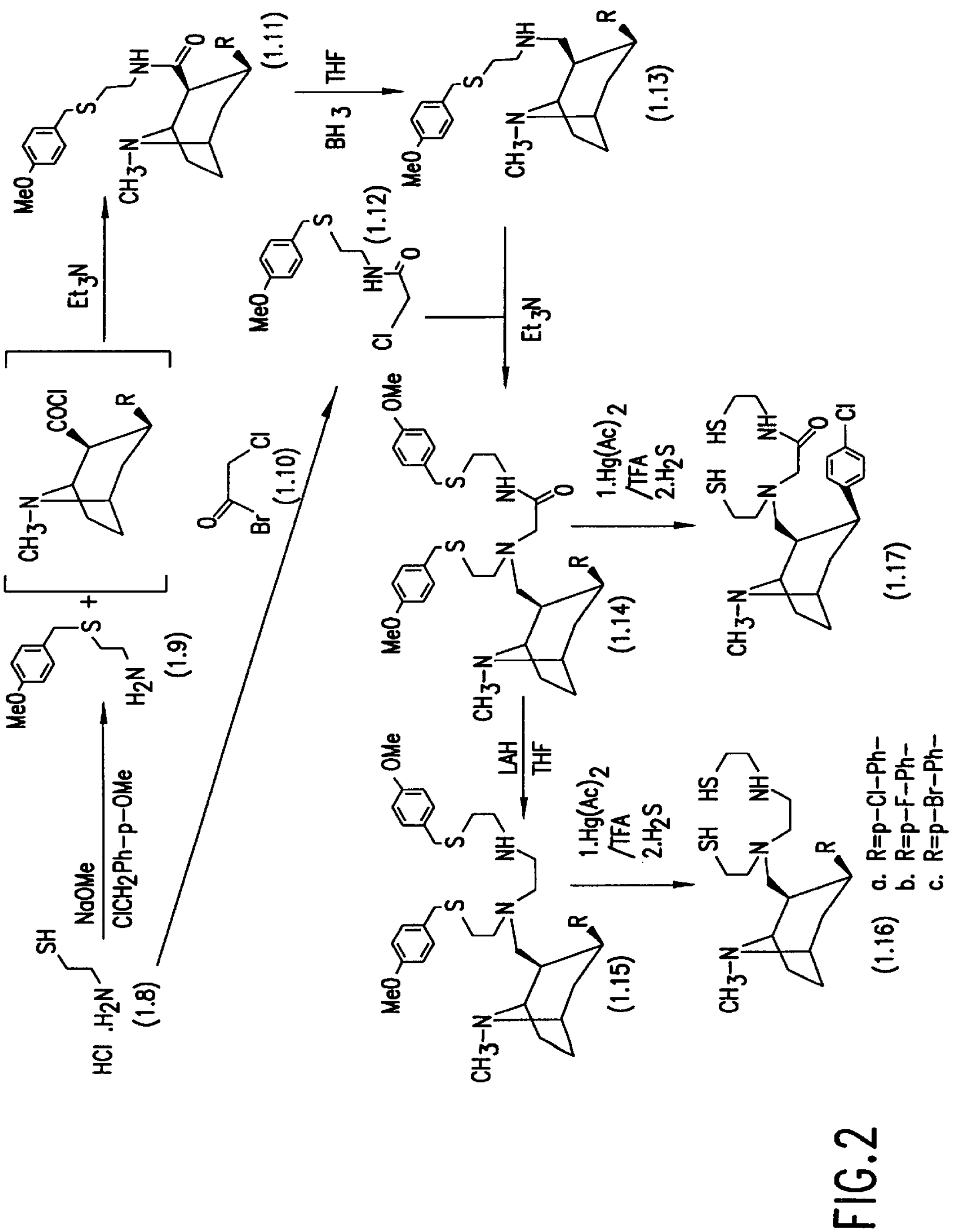
FIG. 2 depicts a general reaction scheme that may be used for synthesizing compounds of Formula I comprising two plus one complexes and having the $N_2S_2$ ligand in the 2β position of the tropane ring and two plus one complexes having an amide on the $N_2S_2$ ligand.
Figure 3:
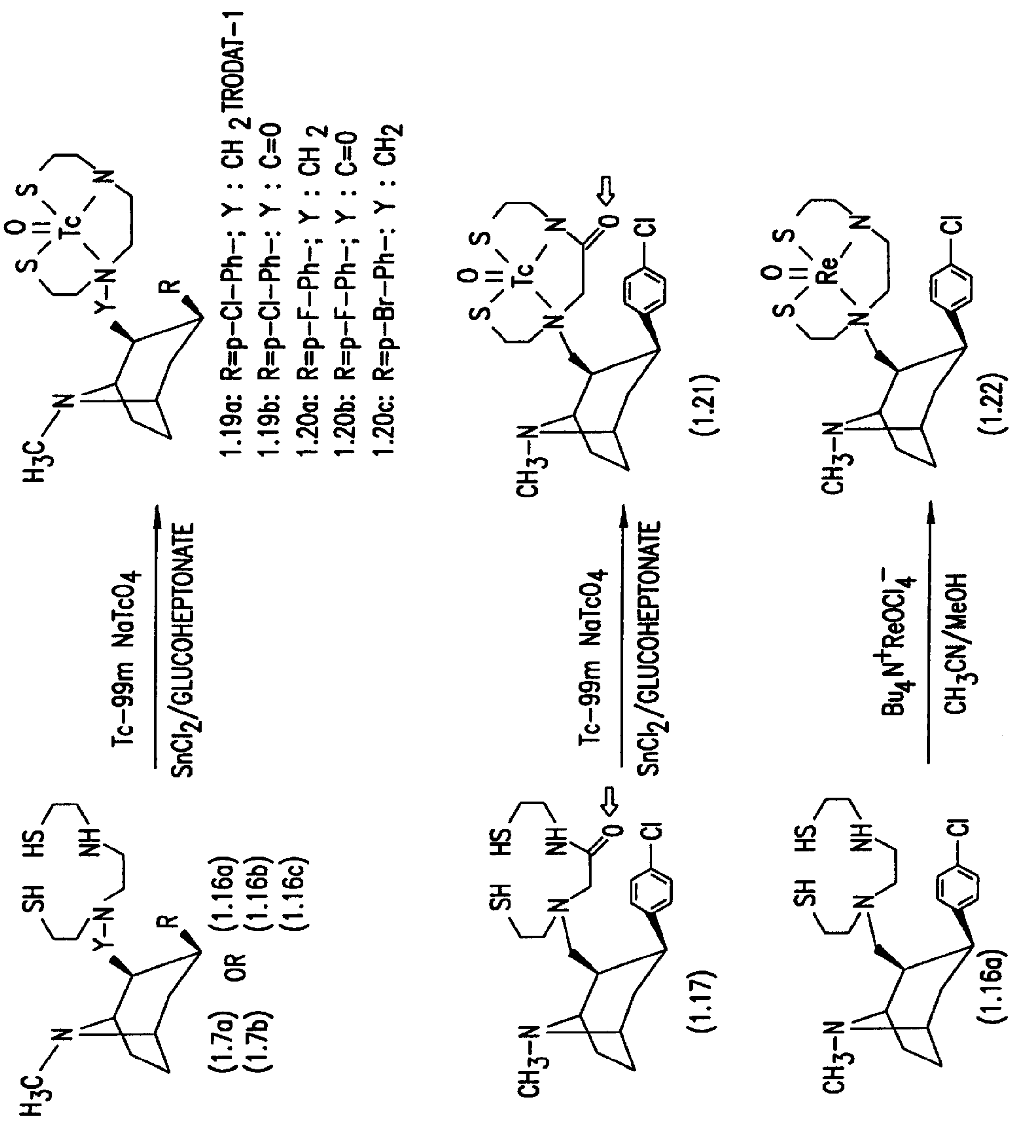
FIG. 3 depicts general reaction schemes that may be used for synthesizing two plus one complexes containing either rhenium or technetium and two plus one complexes having an amide moiety on the $N_2S_2$ ligand.
Figure 4:
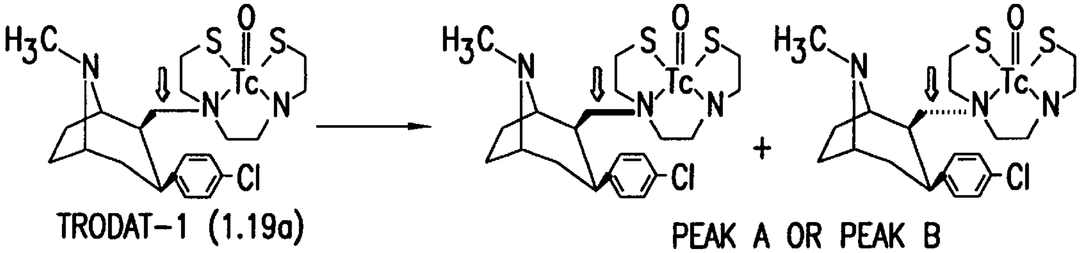
FIG. 4 depicts an HPLC chromatogram of a racemic mixture of a technetium containing compound of the invention.
Figure 4:
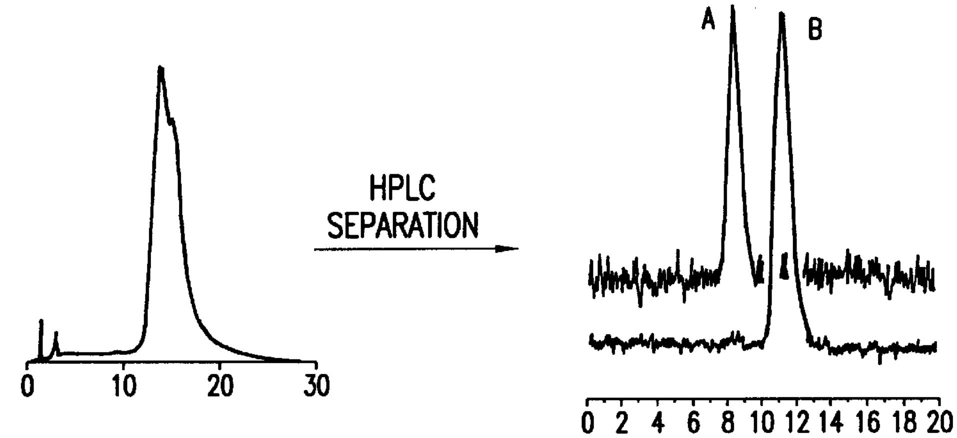

Experimental For Reaction Schemes Depicted In FIGS. 1 and 2.

Syntheses of the 3β-p-chloro and p-fluorophenyl tropane ester, 1.2a and 1.2b, respectively, were carried out according to the procedure described previously (Meltzer, 1993, supra) and the corresponding carboxylic acids 1.3a and 1.3b were made following a literature procedure (Carroll, 1992, supra) and are shown in FIG. 1. The corresponding acyl chlorides of these carboxylic acids were prepared by the action of oxalyl chloride at room temperature intercepted with amine 1.4 to obtain amide 1.5. Diborane reduction of these amides in THF furnished corresponding tertiary amide 1.6. The removal of the 4-methoxybenzyl groups of protected dithiols compound 1.6 was achieved by treating the substrate with $Hg(OAc)_2$ in TFA followed by the removal of mercury as its sulfide.

The synthetic strategy employed for the preparation of compound 1.16 is shown in FIG. 2. Acyl halide 1.3 was converted to secondary amide 1.11 by reacting it with amine 1.9 in the presence of triethyl amine. Secondary amine 1.13 was prepared by diborane reduction of amide 1.11, and was converted to amide 1.14 by alkylations with alkyl chloride 1.12. The amide functions of compound 1.14 were reduced with LAH to yield compound 1.15. Amine 1.15 and amide 1.14 were deprotected with $Hg(OAc)_2$ to obtain trifluoroacetate salts of dithiols 1.16 and 1.17. Since the instability of the disulfides 1.7, 1.16 and 1.17 prevented the purification of these dithiols, they were obtained as their triflate salts, and used directly without further characterization for the preparation of rhenium (22) and technetium (1.19a, 1.19b, 1.20a, 1.20b and 1.21) complexes.

The radiolabeling of 1.7, 1.16 and 1.17 with sodium [$^{99m}$Tc]pertechnetate was successfully achieved by using stannous(II) glucoheptonate as the reducing agent to produce 1.19a, 1.19b, 1.20a, 1.20b and 1.21 in good yield (80%) and radiochemical purity (>95%).

Example 12

Evaluation And Results Comparing Compounds Of The Invention Having the $N_2S_2$ Ligand In The 2β-Position Of The Tropane Core With Other Compounds And Prior Art Compounds The novel series of compounds differ from those previously reported in that the substitution of the bis-aminethanethiol ligand is attached at the 2β-position of the tropane core structure. The corresponding Tc-99m labeled agent displayed a three- to fourfold increase in initial brain uptake (0.1% for N-substituted compound (Meegalla, 1995, supra) vs. 0.3–0.4% in brain at 2 min post injection) and concomitantly retained the specific uptake in the striatum area of the brain. This observation suggests that, in this series of compounds, the 3β-p-fluoro- is slightly less favorable then the corresponding 3β-p-chlorophenyl derivative. As previously reported for the same series of tropane derivatives, the 3β-p-fluoro- derivative displayed a lower brain uptake, which may be due to its lower binding affinity to dopamine transporters. Carroll, 1995, supra.

12a. Biodistribution Comparison

The major criteria for determining the potential usefulness of in vivo dopamine transporter imaging agents are based on an animal biodistribution study. In this case, rats were used as an animal model. After an intravenous injection of the Tc-99m labeled compounds, the values of initial brain uptake (% dose/whole organ) at 2 minutes post intravenous injection are used to measure the ability to penetrate the intact blood-brain barrier. Compounds displaying higher brain uptake are the better agents (minimum requirement >0.1% dose in brain). The second criteria is the specific uptake in the striatum region of the brain, where dopamine transporters are located. The uptake value (% dose/gram) of the striatum (ST) is divided by the background area, cerebellum (CB; essentially devoid of dopamine transporter); the ratio of ST/CB is an indicator for specific uptake (minimum requirement for ST/CB >1.5). Five structurally similar tropane derivatives were examined in this biological study. (Tables 1.1 to 1.4). Compounds 1.19a, 1.19b and 1.20c displayed high initial uptake and high specific retention in brain.

12b. Partition Coefficients Evaluation

One of the key properties for these potential dopamine transporter imaging agents is their neutrality and lipophilicity. The [$^{99m}$Tc] labeled complexes, 1.19a, 1.19b, 1.20a, 1.20b, 1.20c and 1.21, displayed excellent medium range lipophilicity (partition coefficients between 1-octanol and pH 7.0 buffer of 99–1818). It is noteworthy that, contrary to the lowered lipophilicity commonly observed with the addition of an amide group, complex 1.21, containing an amide functional group, exhibited an almost tenfold higher partition coefficient compared to the corresponding reduced compound, 1.19a.

The lipophilicity, as measured by the partition coefficient (1-octanol/pH 7.0 buffer), displayed very unpredictable values. Most striking is the value for 1.21, which contains an amide inside the chelating ring (partition coefficient=1818). The tertiary amide, 1.19b, displayed a similar partition coefficient to that of the fully reduced TRODAT-1, 1.19a. The partition coefficient value is very important for the evaluation of potential brain imaging agents, because they must be neutral and lipophilic in order to penetrate the intact blood-brain barrier. Generally, the optimal range of partition coefficient values for good brain uptake are between 100–1000.

12c. Brain Uptake

Biodistribution studies of 1.19a, 1.19b, 1.20a, 1.20b, 1.20c and 1.21 in rats were performed after an intravenous injection of a tracer dose. The results showed a distribution pattern reflecting regional perfusion (i.e., high uptake in muscle, kidney, liver, brain and skin; Tables 1.1 and 1.2). However, the brain uptake is moderate, ranging from 0.43–0.11% dose/organ at two minutes for the five complexes. The complex containing an amide group, 1.21, showed the lowest brain uptake (Table 1.1) despite its high lipophilicity (P.C.=1818). Increasing the lipophilicity of these compounds does not appear to improve brain uptake in rats. The most significant finding of this initial biodistribution study is that the brain uptake of these complexes, except 1.21, was highly concentrated in the striatal area, where the dopamine transporters are located, compared to a region with no dopamine neurons (i.e., the cerebellar region); therefore, at 60 minutes after an intravenous injection, the ratios of striatum to cerebellum (ST/CB) were found to be 2.66, 2.78, 2.18, 1.92 and 2.82 for 1.19a, 1.19b, 1.20a, 1.20b and 1.20c, respectively. However, complex 21 showed little specific uptake (ST/CB=1.17) at 60 minutes post intravenous injection. The initial biodistribution study suggested that [$^{99m}$Tc]TRODAT-1 (1.19a) is a good imaging agent candidate in this series of complexes. It displayed the highest initial brain uptake, and high retention in the target area (i.e., striatum) at later time points; therefore, a more detailed biodistribution study was carried out. Specific uptake of [$^{99m}$Tc]TRODAT-1 (1.19a) at different time points displayed a prolonged retention, and the ST/CB ratio reached a maximum value of 4.07 at 4 hours after injection (Table 1.3).

Figure 5:
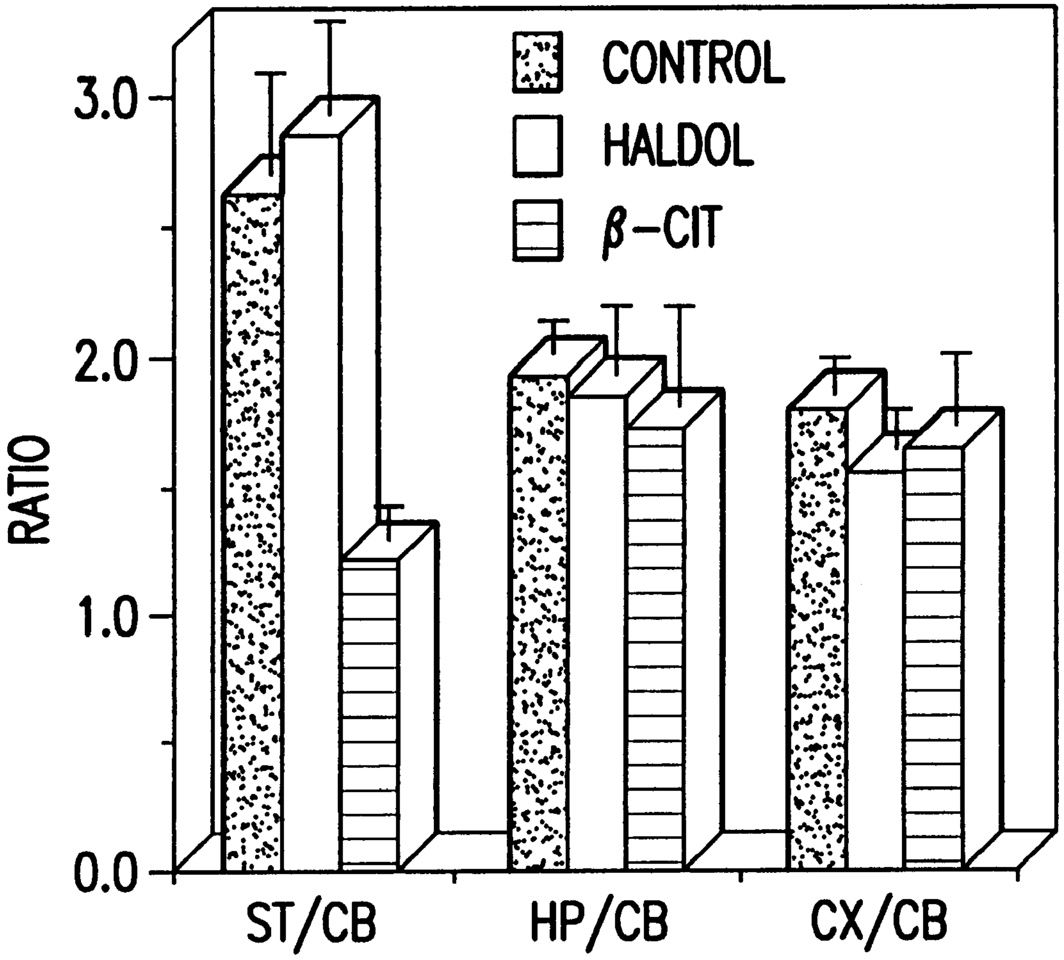
FIG. 5 depicts the ratios of regional brain uptakes at 60 minutes post intravenous injection of [$^{99m}$Tc]TRODAT-1 (1.19a) in control rats and rats pretreated with haldol (1 mg/kg, iv) or β-CIT (1 mg/kg, iv) 5 minutes prior to radiotracer injection. Values shown are means ±SD (n=3–4, $p<0.05$, student t-test). ST: striatum; HP: hippocampus; CX: cortex; CB: cerebellum. The ST area, where dopamine transporters are located, displayed selective regional brain uptake, with the highest concentration ratio (ST/CB=2.6). Pretreatment with β-CIT, which competes with dopamine transporter binding, showed blocking of the specific uptake of [99mTc]TRODAT-1 (1.19a) in the ST area.
Figure 7:
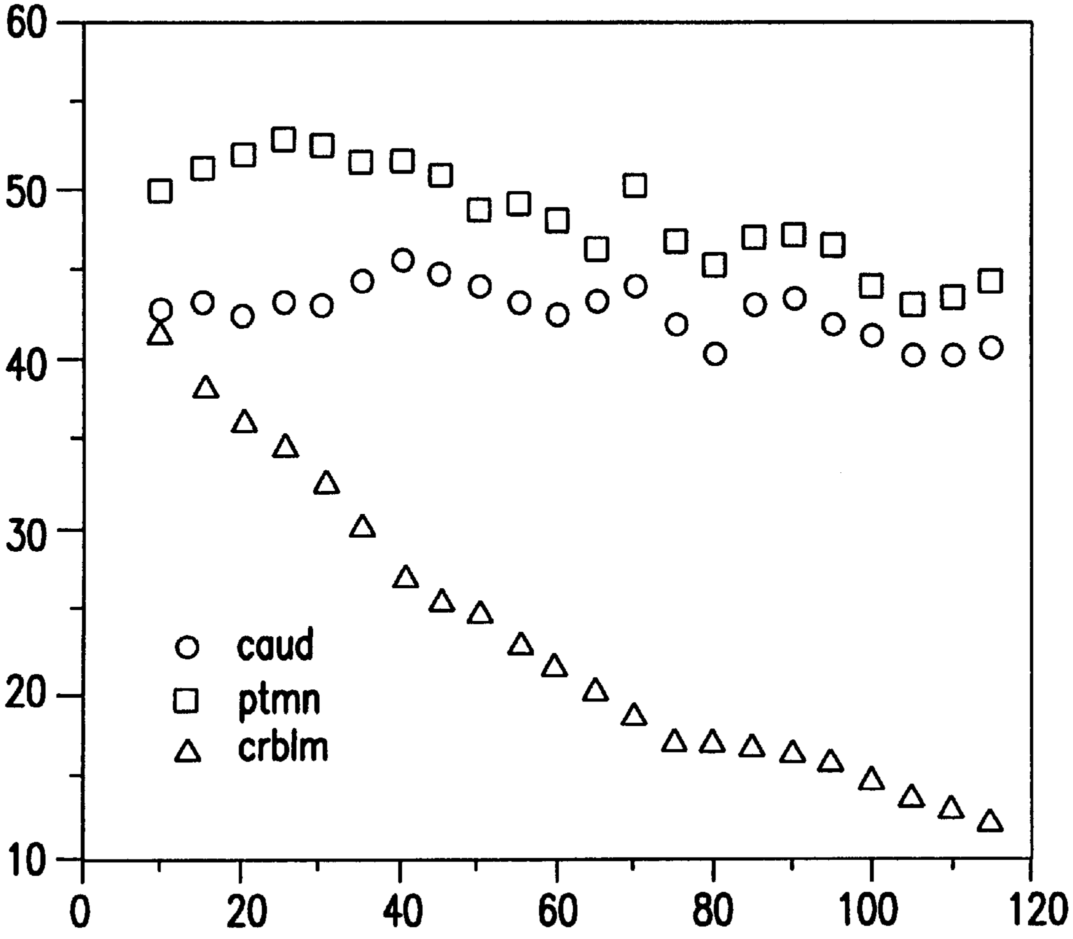
FIG. 7 depicts a time course of regional brain uptakes as measured by SPECT imaging following intravenous injection of [99mTc]TRODAT-1 (1.19a) in a baboon. Regions of right and left caudat and putamen, cerebellum (CB) is expressed as counts/pixel/minute.

Blocking studies in rats were performed at 60 minutes post-injection to characterize further the uptake and binding, and [$^{99m}$Tc]TRODAT-1 (1.19a) did indeed show binding to dopamine transporter sites. In this series of regional brain uptake studies in rats, the ST/CB ratio at 60 minutes post-injection was 2.66 (FIG. 1.1). The specific uptake of [99mTc]TRODAT-1 (1. 19a) in rat striatum could be blocked by pretreating rats with a dose of β-CIT (1 mg/kg, iv), a known dopamine transporter ligand. The specific binding, as indicated by ST/CB, was reduced to 1.0 after pretreatment with β-CIT. The specific binding was not reduced by pretreatment with haldol (1 mg/kg, iv), an agent with a mixed pharmacological profile (binding to various CNS receptors but not to the dopamine transporter); no blocking effect was observed. The ST/CB ratio (2.6) was identical to that in control rats (FIG. 5). The results suggested that uptake in the rat striatum was specifically related to the dopamine transporter in rat brain.

To evaluate further the potential of [$^{99m}$Tc]TRODAT-1 (1.19a) as a dopamine transporter imaging agent, a SPECT imaging study was carried out in a female baboon. To facilitate the identification of anatomical localization, the coronal, transaxial and sagital SPECT images (1.34 mm thick) obtained 60–90 minutes post injection were coregistered with the MRI images of the same baboon. The fused images displayed excellent consistence with the expected localization of this agent in caudate and putamen areas, where the dopamine transporters are known to be located. The images also showed good correlation with PET imaging agent [$^{11}$C]CFT and SPECT imaging agent [$^{123}$I]β-CIT, reported previously. In vitro binding studies of Re complex 1.22 in rat striatal homogenates displayed good binding affinity (Ki=14 nM, using [$^{125}$I]IPT (Kung, 1995, supra) as the ligand; Kd=0.2 nM, data not shown); while the bis-ethanethiol, 1. 16a, displayed a comparable affinity (Ki=7 nM). However, upon intravenous co-injection of the bis-ethanethiol ligand into rats (200 mg/dose, which is equivalent to 1 mg/Kg), the specific uptake (Table 1.2) was not blocked by the competing agent, which suggests that the free thiol compound may not be able to penetrate the intact blood-brain barrier and compete with the binding of [$^{99m}$Tc] TRODAT-1 (1.19a) as a dopamine transporter in the brain. Although the binding affinity of the corresponding Re complex, 1.22, is not as potent as other iodinated tropane derivatives, the brain uptake and retention of [$^{99m}$Tc] TRODAT-1 (1.19a) appears to be sufficient for in vivo SPECT imaging in nonhuman primates.

The initial brain uptake at 2 minutes after intravenous injection in rat brain is the key indicator for evaluating the compound's penetration of the blood-brain barrier. For compounds with high first pass extraction, the brain uptake values at 2 minutes are in the range of 2–3% dose/whole brain after iv injection in rats. Comparing the five structurally similar compounds (Table 1.4), only 1.19a and 1.19b displayed significant uptake; the other three compounds, 1.21, 1.24 and 1.25, showed at least 300% lower uptake.

This observation is very surprising and not consistent with what one would predict by their partition coefficient. Based on this novel finding, compounds containing an amide in the $N_2S_2$ chelating ring system are specifically removed from further development. The prior art, technepine (Madras, 1996, supra), used a $N_2S_2$ chelating ring system containing an amide group (technepine), which provides less favorable biological properties.

For dopamine transporter imaging agents, the target area of the brain is the striatum, where dopamine transporters are highly concentrated. The cerebellum region is suitable for use as the background region, because it has no dopamine transporters. The specific uptake is measured by the ratio of % dose/gram of striatum divided by % dose/gram of cerebellum (ST/CB ratio)—the higher the value, the better the specific uptake, and the more promising as a dopamine transporter imaging agent. Again, the data in Table 1.1 shows that ST/CB ratios for 1.19a and 1.19b are the best among this group of compounds. The specific uptake of these agents in rat brain clearly displays the novel finding that, among the structurally similar compounds containing a $N_2S_2$ chelating group, only 1.19a and 1.19b display the selective localization in the striatum, where dopamine transporters are located. Single photon emission computed tomography (SPECT) images of the selected and claimed agent displayed a high contrast in the target area (striatum) of a baboon (nonhuman primate) brain. The data clearly demonstrate that the new technology can be reduced to practice and is potentially useful for human imaging study of dopamine transporter in brain.

Based on the novel findings regarding biodistribution discussed above, the specific chemcial compounds (1.19a and 1.20a) not containing amide groups and with an $A_3$ or $A_4$ moiety are particularly useful dopamine transporter imaging agents.

Example 13

Evaluation Of Stereoisomeric Compounds

It is possible that tropane derivatives containing a bis-aminoethanethiol group will form stereoisomers, which requires the separation and characterization of these isomers (Table 1.5 a, b, c). Initial evaluation of the stereoisomers suggests that Peak A and Peak B displayed different brain uptake and specific localization in striatum area: Peak A showed higher initial brain uptake (0.5 vs. 0.28% dose/organ, at 2 minutes post-injection for Peak A and Peak B, respectively), but Peak B had a higher ratio (ST/CB 2.72 vs. 3.79 at 60 min post-injection for Peak A and Peak B, respectively). Correlation of dopamine transporter uptake as measured by SPECT imaging and the actual neuronal integrity requires extensive kinetic modeling studies to validate and estimate the potential clinical utility. Optimized imaging protocol and reproducibility of SPECT imaging of this new agent remain to be investigated.

TABLE 1.1

Brain uptake of six Tc-99m labeled tropane derivatives (% dose/organ)

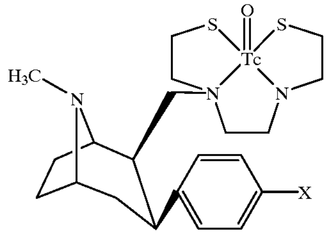

| | X |
|---|---|
| TRODAT-1 (1.19a) | Cl |
| (1.20a) | F |
| (1.20c) | Br |

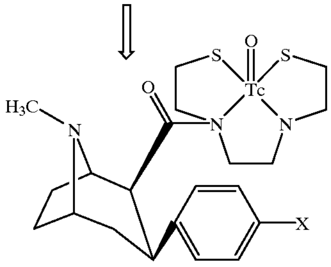

| | X |
|---|---|
| (1.19b) | Cl |
| (1.20b) | F |

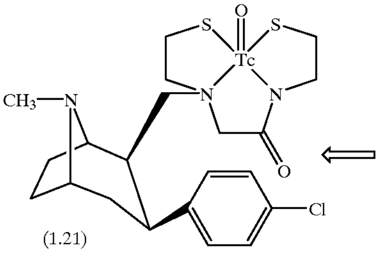

(1.21)

| Compound | 2 min | 60 min | ST/CB Ratio at 60 min.[a] | P.C.[b] |
|---|---|---|---|---|
| 1.19a, TRODAT-1 | 0.43 ± 0.16 | 0.12 ± 0.001 | 2.66 ± 0.01 | 227 |
| 1.19b | 0.39 ± 0.12 | 0.11 ± 0.02 | 2.78 ± 0.32 | 230 |
| 1.20a | 0.37 ± 0.09 | 0.098 ± 0.014 | 2.18 ± 0.32 | 99 |
| 1.20b | 0.31 ± 0.09 | 0.07 ± 0.010 | 1.92 ± 0.28 | 104 |
| 1.20c | 0.41 ± 0.03 | 0.18 ± 0.01 | 2.82 ± 0.19 | 262 |
| 1.21 | 0.11 ± 0.02 | 0.07 ± 0.014[c] | 1.17 ± 0.010 | 1818 |

[a]Striatal/Cerebellum (ST/CB) ratio: % dose per gram of striatum/% does per gram of cerebellum
[b]P.C.: measured between 1-octanol/pH 7.0 phosphate buffer
[c]Data were from rats sacrificed at 30 minutes

TABLE 1.2

Biodistribution in rats post intravenous injection of [99mTc]TRODAT-1, 1.19aa

| Organ | 2 minutes | 60 minutes | 60 minutes* |
|---|---|---|---|
| Blood | 4.94 ± 0.46 | 2.14 ± 0.17 | 6.29 ± 1.12 |
| Heart | 1.47 ± 0.16 | 0.19 ± 0.02 | 0.25 ± 0.05 |
| Muscle | 10.84 ± 1.95 | 10.28 ± 1.36 | 10.37 ± 0.48 |
| Lung | 6.82 ± 0.37 | 1.86 ± 0.36 | 1.76 ± 0.12 |
| Kidney | 5.13 ± 0.75 | 3.06 ± 0.14 | 1.76 ± 0.32 |

TABLE 1.2-continued

| Biodistribution in rats post intravenous injection of [99mTc]TRODAT-1, 1.19aa | | | |
|---|---|---|---|
| Organ | 2 minutes | 60 minutes | 60 minutes* |
| Spleen | 0.42 ± 0.16 | 0.45 ± 0.05 | 0.51 ± 0.06 |
| Liver | 16.62 ± 2.11 | 17.67 ± 3.42 | 20.35 ± 0.99 |
| Skin | 2.66 ± 0.35 | 3.96 ± 0.22 | 4.11 ± 0.29 |
| Brain | 0.43 ± 0.16 | 0.12 ± 0.00 | 0.12 ± 0.01 |

| Regional Brain Distribution (% does/g) | | | |
|---|---|---|---|
| Region | 2 min (ST/CB) | 60 min (ST/CB) | 60 min* (ST/CB) |
| Cerebellum | 0.284 ± 0.066 | 0.057 ± 0.003 (1.00) | 0.059 ± 0.007 (1.00) |
| Striatum | 0.266 ± 0.066 | 0.151 ± 0.002 (2.66) | 0.156 ± 0.018 (2.65) |
| Hippocampus | 0.268 ± 0.090 | 0.096 ± 0.015 (1.69) | 0.104 ± 0.011 (1.77) |
| Cortex | 0.347 ± 0.140 | 0.094 ± 0.012 (1.65) | 0.090 ± 0.009 (1.53) |
| Remainder | 0.269 ± 0.076 | 0.076 ± 0.005 (1.34) | 0.079 ± 0.006 (1.34) |

[a]% does/organ, average of 3 rats ± SD
[b]Biodistribution in rats post iv injection of [$^{99m}$Tc]TRODAT-1 with excess ligand (100 mg/does; % does/organ, average of 3 rats ± SD)

TABLE 1.4-continued

Biodistribution in rats (brain uptake, % dose/organ) after an intravenous injection of [$^{99m}$Tc]TRODAT-1 and related compounds (% dose/organ, average of 3 rats ± SD)

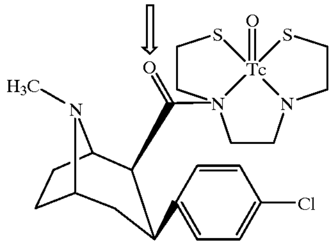

(1.19b)

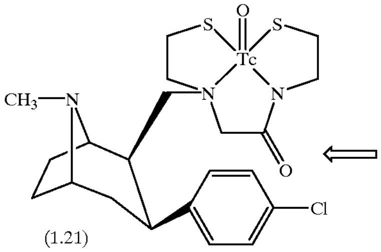

(1.21)

TABLE 1.3

| Biodistribution in rats post intravenous injection of [99mTc]TRODAT-1, 1.19a[a] | | | | | | |
|---|---|---|---|---|---|---|
| | 2 min | 30 min | 60 min | 120 min | 240 min | 360 min |
| ST/CB Ratio | 0.93 ± 0.23 | 2.04 ± 0.18 | 2.66 ± 0.01 | 3.90 ± 1.33 | 4.07 ± 0.54 | 2.97 ± 0.14 |

[a]Striatal/Cerebellum (ST/CB) ratio: % dose per gram of striatum/% dose per gram of cerebellum

TABLE 1.4

Biodistribution in rats (brain uptake, % dose/organ) after an intravenous injection of [$^{99m}$Tc]TRODAT-1 and related compounds (% dose/organ, average of 3 rats ± SD)

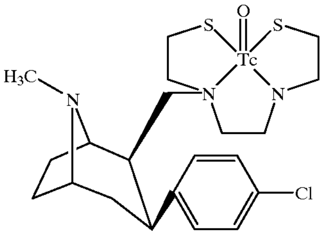

TRODAT-1 (1.19a)

TABLE 1.4-continued

Biodistribution in rats (brain uptake, % dose/organ) after an intravenous injection of [$^{99m}$Tc]TRODAT-1 and related compounds (% dose/organ, average of 3 rats ± SD)

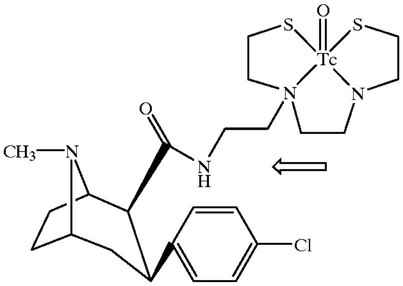

(1.24)

TABLE 1.4-continued

Biodistribution in rats (brain uptake, % dose/organ) after an intravenous injection of [$^{99m}$Tc]TRODAT-1 and related compounds (% dose/organ, average of 3 rats ± SD)

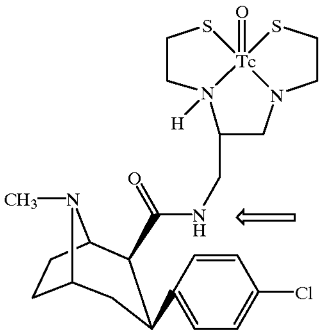

(1.25)

| Organ | 2 min | 30 min | ST/CB ratio (30 min) | Partition coefficient |
|---|---|---|---|---|
| TRODAT-1 (1.19a) | 0.425 ± 0.120 | 0.232 ± 0.021 | 2.0 | 227 |
| (1.19b) | 0.39 ± 0.12 | 0.21 ± 0.03 | 2.78 | 230 |
| (1.21) | 0.11 ± 0.02 | 0.070 ± 0.014 | 1.17 | 1818 |
| (1.24) | 0.028 ± 0.007 | 0.022 ± 0.002 | — | 1.28 |
| (1.25) | 0.040 ± 0.007 | 0.013 ± 0.002 | — | 1.07 |

TABLE 1.5

Biodistribution in rats (brain uptake, % dose/organ) after an intravenous injection of [$^{99m}$Tc]TRODAT-1 (1.19a)(racemic) and stereoisomers (Peak A and Peak B) (% dose/organ, average of 3 rats ± SD)

| Organ | 2 min | 60 min |
|---|---|---|
| Blood | 1.98 ± 0.19 | 1.00 ± 0.15 |
| Heart | 1.76 ± 0.09 | 0.21 ± 0.00 |
| Muscle | 33.61 ± 4.31 | 14.98 ± 0.49 |
| Lung | 9.68 ± 0.51 | 3.06 ± 0.28 |
| Kidney | 5.47 ± 1.04 | 2.04 ± 0.21 |
| Spleen | 0.27 ± 0.04 | 0.46 ± 0.18 |
| Liver | 9.55 ± 2.19 | 17.75 ± 1.81 |
| Skin | 2.73 ± 0.39 | 3.56 ± 0.65 |
| Brain | 0.50 ± 0.06 | 0.21 ± 0.01 |

TABLE 1.5a

Biodistribution in rats after an intravenous injection of peak A (1.19a) (% dose/organ, average of 3 rats ± SD)
Regional brain distribution (% dose/g)

| Region | 2 min | 60 min | Ratio @ 60 min |
|---|---|---|---|
| Cerebellum | 0.289 ± 0.017 | 0.086 ± 0.007 | 1.00 |
| Striatum | 0.318 ± 0.063 | 0.235 ± 0.009 | 2.72 |
| Hippocampus | 0.287 ± 0.082 | 0.138 ± 0.003 | 1.61 |
| Cortex | 0.387 ± 0.047 | 0.139 ± 0.007 | 1.61 |
| Remainder | 0.283 ± 0.047 | 0.119 ± 0.007 | 1.38 |

TABLE 1.5b

Biodistribution in rats after an intravenous injection of peak B (1.19a) (% dose/organ, avg. 3 rats ± SD)

| Organ* | 2 min | 60 min |
|---|---|---|
| Blood | 4.02 ± 0.20 | 1.89 ± 0.21 |
| Heart | 1.28 ± 0.15 | 0.19 ± 0.06 |
| Muscle | 41.46 ± 11.33 | 8.60 ± 2.51 |
| Lung | 6.00 ± 1.11 | 1.23 ± 0.89 |
| Kidney | 4.47 ± 0.69 | 1.87 ± 0.80 |
| Spleen | 0.27 ± 0.03 | 0.41 ± 0.24 |
| Liver | 9.07 ± 1.66 | 18.71 ± 2.54 |
| Skin | 3.43 ± 0.62 | 4.11 ± 0.62 |
| Brain | 0.28 ± 0.01 | 0.12 ± 0.02 |

Regional Brain Distribution (% dose/g)

| Region | 2 min | 60 min | Ratio @ 60 min |
|---|---|---|---|
| Cerebellum | 0.167 ± 0.019 | 0.047 ± 0.010 | 1.00 |
| Striatum | 0.155 ± 0.019 | 0.177 ± 0.008 | 3.79 |
| Hippocampus | 0.137 ± 0.003 | 0.083 ± 0.012 | 1.77 |
| Cortex | 0.199 ± 0.012 | 0.083 ± 0.016 | 1.78 |
| Remainder | 0.149 ± 0.007 | 0.069 ± 0.009 | 1.48 |

TABLE 1.5c

Brain uptake in rats after an intravenous injection of the Racemate (1.19a) (% dose/organ, average of 3 rats ± SD)

| Organ | 2 min | 60 min |
|---|---|---|
| Brain | 0.43 ± 0.16 | 0.12 ± 0.00 |

Regional brain distribution (% dose/g)

| Region | 2 min | 60 min | Ratio @ 60 min |
|---|---|---|---|
| Cerebellum | 0.284 ± 0.066 | 0.057 ± 0.003 | 1.00 |
| Striatum | 0.266 ± 0.066 | 0.151 ± 0.002 | 2.66 |
| Hippocampus | 0.268 ± 0.090 | 0.096 ± 0.015 | 1.69 |
| Cortex | 0.347 ± 0.140 | 0.094 ± 0.012 | 1.65 |
| Remainder | 0.269 ± 0.076 | 0.076 ± 0.005 | 1.34 |

General Experimental For Examples 14 To 17

Reagents used in the syntheses were purchased from Aldrich (Milwaukee, Wis.) or Fluka (Ronkonkoma, N.Y.), and were used without further purification unless otherwise indicated. Anhydrous $Na_2SO_4$ was used as a drying agent. Reaction yields are reported without attempts at optimization. Thin layer chromatography was performed on EM Science (Gibbstown, N.J.) precoated (0.2 mm) silica gel 60 plates, and the spots were detected with iodine vapor and/or UV light. Silica gel 60 (70–230 mesh), obtained from EM Science (Gibbstown, N.J.), was used for column chromatography. 1H NMR spectra were obtained on a Bruker spectrometer (Bruker AC 300). All samples prepared for NMR analysis were dissolved in CDCl3, purchased from Aldrich. Chemical shifts are reported as d values with TMS as the internal reference. Coupling constants are reported in Hz. The multiplicity is defined by s (singlet), t (triplet), td (triplet of doublet), dt (doublet of triplet) and m (multiplet). IR spectra were recorded with a Mattson Polaris FT-IR spectrometer and are reported in cm-1. Melting points were determined on a Meltemp apparatus (Cambridge, Mass.) and are uncorrected. The compound reference numbers used in the Examples and Tables correspond to the compounds depicted in FIGS. 8–11.

Example 14

Preparation of 2.2

A mixture of nortropane derivative 2.1 (1 g, 3.9 mmol), KI (664 mg, 4 mmol), $K_2CO_3$ (1.4 g, 10 mmol) and bromopropanol (0.37 mL, 4 mmol) in dioxane (25 mL) was heated at reflux under N2 for 12 hours. The reaction mixture was allowed to cool to room temperature and then filtered. The filtrate was partitioned between water and $CH_2Cl_2$. The $CH_2Cl_2$ layer was concentrated in vacuo to obtain a viscous oil, which was purified on silica (2% MeOH: $CH_2Cl_2$ drop of NH3) to obtain the title compound as a colorless oil. Yield 46%; IR ($CHCl_3$) 3330, 1739; 1H NMR 1.45–1.8 (5H, m), 1.95–2.2 (m, 2H), 2.37–2.5 (m, 3H), 2.85–2.89 (m, 1H), 2.98 (td, J1=5.1, J2=12.8, 1H), 3.45 (s, 3H), 3.57–3.63 (m, 2H), 3.69–3.78 (m, 2H), 7.11 and 7.19 (d, J=8.55, 2H each).

Example 15

Preparation of 2.3

A solution of alcohol, 2.1 (337 mg, 1 mmol) and $Et_3N$ (0.14 mL, 1 mmol) in $CH_2Cl_2$ was cooled to −10° C. under $N_2$ and MsCl 9 0.07 mL, 1 mmol) was added over 5 minutes. The resulting solution was stirred for 20 minutes. and water (10 mL) was added and allowed to warm to room temperature. The $CH_2Cl_2$ layer was separated and concentrated in vacuo at 25° C. to obtain a viscous oil which was dried in vacuo for 30 minutes. The mesylate obtained was dissolved in dry acetone (10 ml) and anhydrous LiBr (108 mg, 1.2 mmol) was added. The resulting mixture was heated at reflux for 5 hours under N2. The reaction mixture was allowed to cool to room temperature and concentrated in vacuo to obtain a viscous oil which was purified on silica (1% MeOH: $CH_2Cl_2$) to obtain the title compound as a viscous oil. 62%; IR ($CHCl_3$) 1740; 1H NMR 1.58–2.15 (m, 7H), 2.38 (t, J=6.18, 2H), 2.55 (dt, J1=2.88, J1=12.36, 1H), 2.7–3.9 (m, 2H), 3.36–3.37 (m, 1H), 3.5–3.68 (m, 6H), 7.16 and 7.23 (d, J=8.7, 2H each).

Example 16

Preparation of 2.4

A solution of bromo compound 2.3 (1.4 g, 3.6 mmol), N,N'-bis-(2-S-4-methoxybenzyl-2-mercapto)ethyl-ethylenediamine (3.3 g, 7.9 mmol), KI (770 mg, 3.6 mmol), $K_2CO_3$ (1.4 g, 10.1 mmol) in dioxane (50 mL) was heated at reflux for 15 hours. The reaction mixture was allowed to cool to room temperature and filtered. The filtrate was concentrated in vacuo to obtain a viscous oil, which was partitioned in between water and $CH_2Cl_2$. The CH2Cl2 layer was concentrated in vacuo to obtain an oil which was purified on silica (EtOAc:MeOH:$NH_4OH$; 9:0.9:0.1). 21%; IR (neat) 1746; 1H NMR 1.4–1.7 (m, 4H), 2–2.4 (m, 6H), 2.41–2.7 (m, 12H), 2.75 (t, J=6.8, 2H), 2.85–2.93 (m, 2H), 3.34–3.36 (m, 2H), 3.45 (s, 3H), 3.63–3.69 (m, 5H), 3.77 (s, 6H), 6.82 (d, J=8.7, 4H), 7.14–7.26 (m, 8H).

Example 17

Preparation of 2.7a

Figure 10:
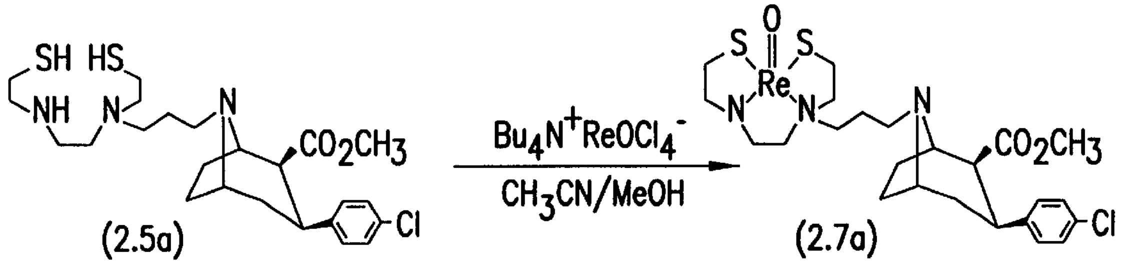
FIG. 10 depicts a reaction scheme that may be used for preparing a rhenium-containing compound of the invention.
Figure 11:
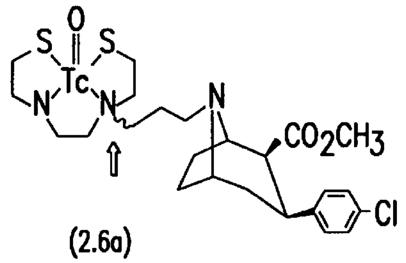
FIG. 11 depicts HPLC chromatograms of a racemic mixture of an $N_2S_2$ compound of the invention where the $N_2S_2$ ligand is attached to the bridge head nitrogen of the tropane core and an HPLC chromatogram of the resolved isomers.
Figure 11:
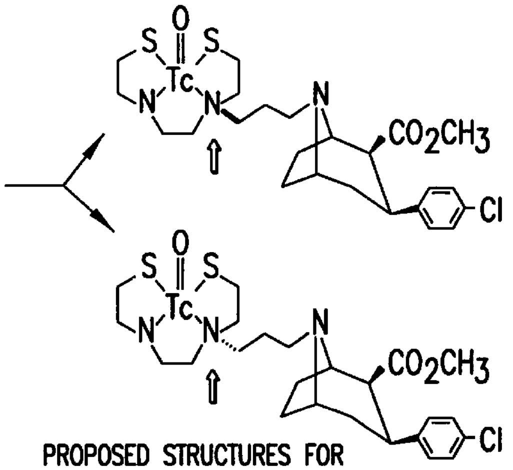
Figure 11:
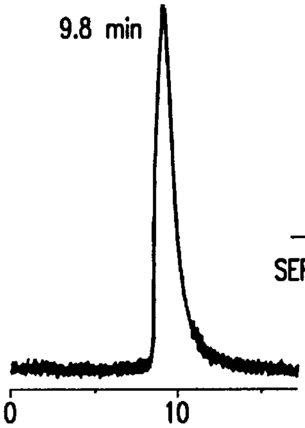
Figure 11:
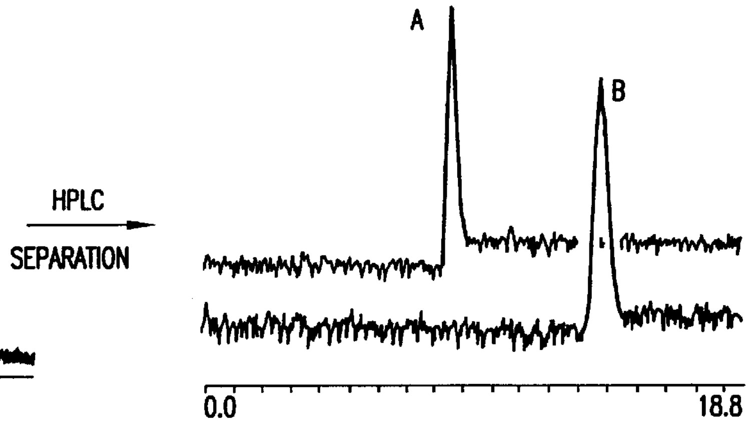

Substrates 2.5a (1 mmol) was dissolved in TFA (7.5 mL) and anisole (0.25 mL) at 0° C. and Hg(OAc)2 (636 mg, 2 mmol) was added. The resulting mixture was stirred for 30 minutes. and concentrated in vacuo to obtain a viscous oil which was dried in vacuo for 30 minutes. Dry ether (10 mL) was then added to the above oil and the resulting suspension was sonicated for 5 minutes. The colorless solid formed was collected by suction filtration and dried in vacuo for 20 minutes and dissolved in absolute EtOH (10 mL). H2S gas was passed through the solution for 20 minutes and the reaction mixture was filtered through a pad of celite. Filtrate was concentrated in vacuo and redissolved in $CH_2Cl_2$ (10 mL) and washed with saturated $Na_2CO_3$ (10 mL). The CH2Cl2 layer was concentrated in vacuo to obtain 2.5a as a viscous oil. $Bu_4NReOCl_4$ (588 mg, 1 mmol) was dissolved in MeOH (5 mL) under Ar and cooled to 0° C. Dithiol 2.5a (485 mg, 1 mmol) in MeOH (5 mL) was then added followed by $Et_3N$ (0.56 mL, 4 mmol). The resulting solution was stirred at room temperature for 12 hours and concentrated in vacuo. The residue obtained was subjected to preparative TLC ($CH_2Cl_2$:MeOH:$NH_4OH$ 9:0.9:0.1) to obtain stereoisomeric mixture of 2.5a. 23%; mp mixture 95–110° C. (sub.). IR (KBr) 1743, 941; 1H NMR 2.8–3.2 9 (m), 3.2–3.45 (m), 3.49 and 3.52 (s each), 3.52–3.7 (m), 4–4.25 (m), 7.14 (d, J=8.7), 7.15 (d, J=8.7), 7.34 (m). Radiochemistry was achieved by FIG. 9. The corresponding rhenium complex, 2.6, was prepared as surrogate for chemical analysis. FIG. 10.

TABLE 2.1a

Biodistribution in rats after intravenous injection of peak A of (2.6a) (% dose/organ, avg. of 3 rats ± SD)

| Organ | 2 min | 30 min |
|---|---|---|
| Blood | 2.41 ± 0.33 | 1.16 ± 0.06 |
| Heart | 0.79 ± 0.03 | 0.22 ± 0.02 |
| Muscle | 7.78 ± 0.32 | 10.41 ± 1.26 |
| Lung | 15.63 ± 2.31 | 9.65 ± 1.37 |
| Kidney | 2.97 ± 0.09 | 1.25 ± 0.11 |
| Spleen | 0.42 ± 0.10 | 0.42 ± 0.05 |
| Liver | 14.29 ± 2.56 | 20.87 ± 2.23 |
| Skin | 1.59 ± 0.68 | 5.69 ± 0.73 |
| Brain | 0.25 ± 0.04 | 0.13 ± 0.02 |

TABLE 2.1b

Biodistribution in rats after intravenous injection of peak B of (2.6a) (% dose/organ, avg. of 3 rats ± SD) * n = 1

| Organ* | 2 min | 30 min |
|---|---|---|
| Blood | 3.96 ± 0.70 | 1.82 ± 0.43 |
| Heart | 0.70 ± 0.21 | 0.24 ± 0.08 |
| Muscle | 9.92 ± 1.04 | 8.09 ± 1.686 |
| Lung | 19.16 ± 2.06 | 12.51 ± 1.46 |
| Kidney | 2.03 ± 0.45 | 1.24 ± 0.18 |
| Spleen | 0.42 ± 0.10 | 0.67 ± 0.17 |
| Liver | 19.56 ± 3.21 | 28.57 ± 2.94 |
| Skin | 1.25 ± 0.17 | 3.25 ± 0.76 |
| Brain | 0.19 ± 0.041 | 0.094 ± 0.026 |

Regional brain distribution (% dose/g)

| Region | 2 min | 30 min | Ratio v. CB |
|---|---|---|---|
| Cerebellum | 0.13 ± 0.01 | 0.041 ± 0.009 | — |
| Striatum | 0.10 ± 0.03 | 0.057 ± 0.014 | 1.4 |
| Hippocampus | 0.090 ± 0.01 | 0.054 ± 0.012 | 1.3 |
| Cortex | 0.14 ± 0.03 | 0.064 ± 0.016 | 1.6 |
| Remainder | 0.10 ± 0.02 | 0.052 ± 0.015 | 1.3 |

TABLE 2.1c

Brain uptake in rats after intravenous injection of the Racemate of (2.6a) (2.5; % dose/organ, avg. of 3 rats ± SD)

| Organ | 2 min | 30 min |
|---|---|---|
| Brain | 0.27 ± 0.02 | 0.11 ± 0.02 |

| | Regional brain distribution (% dose/g) | | |
|---|---|---|---|
| Region* | 2 min | 30 min | Ratio v. CB |
| Cerebellum | 0.161 ± 0.015 | 0.048 ± 0.004 | — |
| Striatum | 0.159 ± 0.025 | 0.086 ± 0.010 | 1.8 |
| Hippocampus | 0.139 ± 0.016 | 0.063 ± 0.008 | 1.4 |
| Cortex | 0.183 ± 0.014 | 0.072 ± 0.003 | 1.5 |
| Remainder | 0.146 ± 0.017 | 0.062 ± 0.007 | 1.4 |

General Experimental For Examples 18 To 28

Reagents used in the syntheses were purchased from Aldrich (Milwaukee, Wis.) or Fluka (Ronkonkoma, N.Y.), and were used without further purification unless otherwise indicated. Anhydrous $Na_2SO_4$ was used as a drying agent. Reaction yields are reported without attempts at optimization. Thin layer chromatography was performed on EM Science (Gibbstown, N.J.) precoated (0.2 mm) silica gel 60 plates, and the spots were detected with iodine vapor and/or UV light. Column chromatography was performed on silica gel 60 (70–230 mesh) obtained from EM Science (Gibbstown, N.J.). The spectra of $^1H$ and $^{13}C$ were obtained using a Bruker spectrometer. All samples prepared for NMR analysis were dissolved in $CDCl_3$ purchased from Aldrich. Chemical shifts are reported as d values with chloroform or TMS as the internal reference. Coupling constants are reported in Hz. The multiplicity is defined by s (singlet), d (doublet), t (triplet), brs (broad signal), dt (doublet of triplet) and m (multiplet). IR spectra were recorded with a Mattson Polaris FT-IR spectrometer and are reported in $cm^{-1}$. Melting points were determined on a Meltemp apparatus (Cambridge, Mass.), and are uncorrected. Elemental analyses were performed by Atlantic Microlabs (Norcross, Ga.). HRMS was performed by the Nebraska Center for Mass Spectroscopy, University of Nebraska (Lincoln, Nebr.).

Compounds 3.7, 3.8, 3.10 and 3.12 were prepared according to the literature methods. Satisfactory elemental analyses (within 0.4%) could not be obtained for the thiols and dithiols and hence HRMS data for those compounds are reported. The compound reference numbers used in the examples and Tables correspond to the compounds depicted in the reaction schemes.

Example 18

Preparation of N-[(2-(4'-methoxybenzylthio)-2-methylpropyl)] 2-(4'-methoxybenzylthio)-2-methyl-propionamide (3.3)

2-(4'-methoxybenzylthio)-2-methylpropionic acid (2.4 g, 10 mmol) and $SOCl_2$ (7 mL) in $CHCl_3$ (50 mL) were heated at reflux for 3 hours. The reaction mixture was allowed to cool to room temperature and concentrated in vacuo. The resulting oil, 3.1, was dried under a high vacuum, redissolved in $CH_2Cl_2$ (20 mL) and cooled to −20° C. A solution of 2-(4'-methoxybenzylthio)-2-methylpropanamine, 3.2, and $Et_3N$ (1.7 mL) in $CH_2Cl_2$ (20 mL) was then added, and the resulting mixture was stirred at room temperature for 12 hours. Water (50 mL) was added and the product, 3.3, was extracted with $CH_2Cl_2$ (2×25 mL). The $CH_2Cl_2$ layer was dried ($Na_2SO_4$) and concentrated in vacuo to obtain a viscous oil which was chromatographed on silica (50% EtOAc:hexane) to obtain the title compound, 3, as a waxy solid. Yield 63%; IR ($CHCl_3$) 1664 $cm^{-1}$; 1H NMR (300 Mhz) D 1.33 (s, 12H), 2.56 (s, 2H), 3.69 (s, 4H), 3.76 (s, 6H), 6.80 and 7.25 (D, J=8.67 Hz, 4H each); HRMS (FAB) m/z 447.1902 calculated for $C_{23}H_{33}NO_3S_2$, $M^+$ $^+1$, 448.1994.

Example 19

Preparation of N,N-di[(2-(4'-methoxybenzylthio)-2-methylpropyl)] amine (3.4)

$BH_3·THF$ (100 mL, 1M solution in THF) was added to a solution of compound 3.3 (Example 18 compound) (4.4 g, 10 mmol) in THF (100 mL), and the resulting mixture was heated at reflux under $N_2$ for 12 hours. The reaction mixture was cooled in an ice bath, and water (20 mL) was carefully added. The resulting solution was concentrated in vacuo to obtain a viscous oil that was suspended in 6N HCl (50 mL). This mixture was heated at reflux for 1 hour. After the reaction mixture was cooled in an ice bath, it was basified with concentrated $NH_4OH$, and the product, 3.4, was extracted with $CH_2Cl_2$ and purified on silica (EtOAc). Yield 63%; m.p. 58–60° C.; IR ($CHCl_3$) 1609 $cm^{-1}$; 1H NMR (300 MHz) D 1.35 (s, 12H), 2.59 (s, 4H), 3.71 (s, 4H), 3.78 (s, 6H), 6.81, and 6.24 (D, J=9.92 Hz, 4H each); HRMS (FAB) m/z 433.2109 calculated for $C_{24}H_{35}O_2S_2N$, $M^+$ $^+1$, 434.2198. Anal. calculated for $C_{24}H_{35}O_2S_2N$: C, 66.51; H, 8.06; Found: C, 66.12; H, 8.62.

Example 20

Preparation of N,N-di[(2-(4'-methoxybenzylthio)-2-methylpropyl)]-methylamine (3.5)

$NaBH_3CN$ (500 mg, 8 mmol) was added to a solution of 3.4 (Example 19 compound) (2 g, 5 mmol) and methanol (2 mL, 37% aq.) in $CH_3CN$. The resulting mixture was stirred for 15 minutes, and glacial acetic acid was added dropwise until the solution tested neutral on wet pH papers. The mixture was stirred for 45 minutes and the solvents were removed. 2N KOH (10 mL) was added to the residue, and the resulting mixture was extracted with ether (3×10 mL). The ether extracts were combined, washed with 0.2N KOH (10 mL) then extracted with 1N HCl (2×20 mL). The acid extracts were combined, neutralized with solid KOH and re-extracted with ether (3×10 mL). Ether layers were combined and concentrated in vacuo to obtain a viscous oil, 3.5, which was purified on silica (EtOAc). Yield 73%; oil; IR ($CHCl_3$) 1604 $cm^{-1}$; 1H NMR (300 MHz) D 1.38 (s, 12H), 2.56 (s, 3H), 2.66 (s, 4H), 3.74 (s, 4H), 3.77 (s, 6H), 6.83, and 7.25 (D, J=8.67 Hz, 4H each); HRMS (FAB) m/z 447.2265 calculated for $C_{25}H_{37}O_2S_2N$, $M^+$ $^+1$, 448.2361.

Example 21

Preparation of N,N-di[(2-mercapto)-2-methylpropyl)]-methylamine (3.6)

Amine 3.5 (Example 20 compound) (2.6 g, 6 mmol) and anisole (1.5 mL) in TFA (45 mL) were cooled to 0° C., and $Hg(OAc)_2$ (1.91 g, 6 mmol) was added. This mixture was stirred at 0° C. for 15 minutes and concentrated in vacuo at room temperature. The residue was dried under a high vacuum for 30 minutes and dry ether (50 mL) was added. The resulting solid was collected by suction filtration and redissolved in ethanol (100 ml). Hydrogen sulfide was then bubbled through the ethanol solution for 15 minutes, and the black precipitate that formed was filtered through a thick pad of celite. The filtrate was concentrated in vacuo to obtain a colorless oil that was dried under a high vacuum for 30 minutes. 1N HCl (20 mL) and ether (20 mL) were added to the above oil, and the resulting mixture was vigorously stirred for 15 minutes and transferred to a separating funnel. The aqueous layer was separated and basified with concentrated $NH_4OH$, and the resulting colorless product was extracted with $CH_2Cl_2$ (20×2 mL). The $CH_2Cl_2$ layer was dried ($Na_2SO_4$) concentrated in vacuo to obtain a viscous oil, 3.6, which was stored under a blanket of argon. Yield 66%; oil; IR ($CHCl_3$) 1604 $cm^{-1}$; $^1H$ NMR (300 MHz) D 1.3 (s, 12H), 2.17 (brs, 2H), 2.5 (s, 3H), 2.63 (s, 4H); HRMS (EI) m/z 207.1115 calculated for $C_9H_{21}NS$, $M^+$ −2, 205.0955.

Example 22

Preparation of N,N-di[(2'-mercaptoethyl)]-2-methylpropylamine (3.9)

Ethylene sulfide (2 g, 22 mmol), isobutyl amine (1.4 mL, 14 mmol) and toluene (5 mL) were heated at 110° C. in a sealed tube for 8 hours. Upon cooling, the solution was filtered to remove colorless solid formed during the reaction and the filtrate obtained was concentrated in vacuo. The product, 3.9, was obtained by fractional distillation. Yield 23%; bp 78–80° C. (4 Hgmm); IR (neat) 2964, 2799, 2551 cm-1; 1H NMR (300 MHz) d 0.82 (d, J=9 Hz, 6H), 1.64 (brs, 3H), 2.03 (d, J=9 Hz, 2H), 2.54 (m, 8H); HRMS (EI) m/z calculated for C8H19NS2, M+−.

Example 23

Preparation of N,N-di[(2-mercaptoethyl)] -2-aminoethyl-4-morpholine) (3.11)

Ethylene sulfide (5 g, 38 mmol), 4-(2-aminoethyl) morpholine (7.6 mL, 76 mmol) and toluene (30 mL) were heated at 110° C. in a sealed tube overnight. Upon cooling, the solution was filtered to remove colorless solid formed during the reaction and the filtrate obtained was concentrated in vacuo. The product was purified by flash column chromatography on silica (5% ethanol/ethyl acetate) to obtain the titled compound, 3.11. 1H NMR (300 MHz) d 1.95 (s, 2H), 2.43–2.45 (m, 6H), 2.65–2.75 (m, 10H), 3.68 (m, 4H). Anal. calculated for $C_{10}H_{22}OS_2N_2$: C, 37.15; H, 7.48; N, 8.66 Found: C, 37.42; H, 7.33; N, 7.29.

Example 24

General Procedure for the Preparation of Trityl Compounds (3.15–3.18)

Tritylthiol ($Ph_3CSH$) (1 g, 3.6 mmol) in THF (5 nmL) was added over 5 minutes to a pentane washed NaH (60% dispersion, 145 mg, 3.6 mmol) in THF (5 mL) at 0° C., and the resulting mixture was stirred at room temperature for 10 minutes. It was then cooled to 0° C. and treated with 1,2-dibromoethane (0.31 mL, 3.6 mmol). After stirring at room temperature for 30 minutes, the reaction mixture was concentrated and partitioned between EtOAc (20 mL) and water (10 mL). The EtOAc layer was dried over $Na_2SO_4$ and concentrated in vacuo to obtain a yellow oil that solidified on standing.

1,4-dioxane (25 mL), $Na_2CO_3$ (1.15g, 10.8 mmol), NaI (543 mg, 3.6 mmol), and nortropane (3.13 or 3.14) (671 mg, 2.64 mmol) were sequentially added to the bromo compound obtained above (1 g, 3.6 mmol) and the contents were heated at reflux for 18 hours. The reaction mixture was concentrated and partitioned between $CH_2Cl_2$ (50 mL) and water (20 mL). The $CH_2Cl_2$ layer was separated, dried over $Na_2SO_4$ and concentrated in vacuo to obtain a brownish yellow oil that was purified by flash chromatography on silica (10% EtOAc:hexane).

a. N-[2'-(triphenylmethylmercapto)ethyl]-3b-(4"-fluorophenyl) tropane-2b-carboxylic acid methyl ester (3.15)

Yield 51%; mp 49–51° C.; IR ($CHCl_3$) 1743 $cm^{-1}$; $^1H$ NMR (300 MHz) d 1.43 (m, 3H), 1.92 (m, 2H), 2.17 (m, 1H), 2.28 (m, 2H), 2.45 and 2.62 (m, each 1H), 2.93 (m, 2H), 3.3 and 3.5 (m, each 1H), 3.43 (s, 3H), 7.3, and 7.5 (m, 19H); HRMS (FAB) m/z 565.2450 calculated for $C_{36}H_{36}O_2NSF$, $M^{+}$ $^{+}$1, 566.2263. Anal. calculated for $C_{36}H_{36}O_2NSF$: C, 76.46; H, 6.37. Found: C, 76.27; H, 6.07.

b. N-[2'-(triphenylmethylmercapto)ethyl]-3b-(4"-chlorophenyl) tropane-2b-carboxylic acid methyl ester (3.16)

Yield (1.2 g) 57.4%; mp 120–122° C.; IR ($CHCl_3$) 1739 $cm^{-1}$; $^1H$ NMR (300 MHz) D, 1.47 (m, 3H), 1.92 (m, 2H), 2.17 (m, 1H), 2.28 (m, 2H), 2.45 and 2.62 (m, each 1H), 2.93 (m, 2H), 3.3 and 3.5 (m, each 1H), 3.43 (s, 3H), 7.3, and 7.5 (m, 19H); HRMS (EI) m/z 581.2155 calculated for $C_{36}H_{36}O_2NSCl$, $M^+$ -Tr, 338.0983; FAB 581.2155 calculated for $C_{36}H_{36}O_2NSCl$, M+ +1, 582.2233. Anal. calculated for $C_{36}H_{36}O_2NSCl$: C, 74.35; H, 6.19. Found: C, 74.01; H, 6.53.

c. N-[2'-(Triphenylmethylmercapto)propyl]-3b-(4"-fluorophenyl) tropane-2b-carboxylic acid methyl ester (3.17)

Yield 45.9%; mp 72–74√C; IR ($CHCl_3$) 1743 cm-1; 1H NMR (300 MHz) d 1.5 (m, 5H), 2.12 (m, 6H), 2.55 (dt, J1=2.88, J2=12.27, 1H), 2.88 (t, J=4.2, 1H), 2.95 (td, J1=4.83, J2=12.27, 1H) 3.32 and 3.59 (m, each 1H), 3.43 (s, 3H), 6.9–7.4 (m, 19H); HRMS (FAB) m/z 579.2607 calculated for $C_{37}H_{38}O_2NSF$, M++1, 579.2693. Anal. calculated for $C_{37}H_{38}O_2NSF$: C, 76.55, H, 6.55. Found: C, 76.10; H, 6.74.

d. N-[2'-(Triphenylmethylmercapto)propyl]-3b-(4"-chlorophenyl) tropane-2b-carboxylic acid methyl ester (3.18)

Yield 41%; a foam; IR ($CHCl_3$) 1743 cm-1; 1H NMR (300 MHz) d 1.5 (m, 5H), 2.12 (m, 6H), 2.55 (dt, J1=2.88, J2=12.27, 1H), 2.88 (t, J=4.2, 1H), 2.95 (td, J1=4.83, J2=12.27, 1H) 3.32 and 3.59 (m, each 1H), 3.43 (s, 3H), 6.9–7.4 (m, 19 H); HRMS (FAB) m/z 595.2311 calculated for $C_{37}H_{38}O_2NSCl$, M++1, 596.2316. Anal. calculated for $C_{37}H_{38}O_2NSCl$: C, 74.62, H, 6.38. Found: C, 74.23; H, 6.74.

Example 25

General Procedure for the Preparation of Mercapto Compounds (3.19–3.22)

A trityl compound (3.15–3.18) (1 mmol) was dissolved in $CF_3COOH$ (6.5 mL), and anisole (0.2 mL) at 0° C. and $Hg(OAc)_2$ (382 mg, 1.2 mmol) were added. The resulting mixture was stirred at 0° C. for 30 minutes. The reaction mixture was then concentrated in vacuo to obtain a brownish red oil that was dried under high vacuum for 1 hour. Anhydrous ether (50 mL) was added to the above oil, and the mixture was kept under sonication for 15 minutes. The resulting mixture was magnetically stirred for an additional 30 minutes. The colorless precipitate that formed was collected by suction filtration, dried under a high vacuum for 15 minutes and redissolved in ethanol (50 mL). Hydrogen sulfide gas was bubbled through the ethanol solution for 15 minutes, and the black precipitate that formed was filtered through a thick pad of celite. The filtrate was concentrated in vacuo to obtain a colorless oil which was dried in a high vacuum for 30 minutes. 1N HCl (20 mL) and ether (20 mL) were added to this oil, and the resulting mixture was vigorously stirred for 15 minutes and transferred to a separating funnel. The aqueous layer was separated and basified with concentrated $NH_4OH$, and the resulting colorless product was extracted with $CH_2Cl_2$ (20×2 mL). The $CH_2Cl_2$ layer was dried ($Na_2SO_4$) concentrated in vacuo.

a. N-[2'-(mercapto)ethyl]-3b-(4"-fluorophenyl)tropane-2b-carboxylic acid methyl ester (3.19)

Yield 68%; MP 46–48° C.; IR ($CHCl_3$) 1743 $cm^{-1}$; $^1H$ NMR (300 MHz) d (m, 3H), 1.92 (m, 2H), 2.17 (m, 1H), 2.28 (m, 2H), 2.45 and 2.62 (m, each 1H), 2.93 (m, 2H), 3.3 and 3.5 (m, each 1H), 3.43 (s, 3H), 7.3 and 7.5 (m, 19H); HRMS (FAB) m/z 323.1355 calculated for $C_{17}H_{22}O_2NSF$, $M^+$ +1, 324.1596. Anal. calculated for $C_{17}H_{22}O_2NSF$: C, 63.15; H, 6.88. Found: C, 62.55; H, 6.38.

b. N-[2'-(mercapto)ethyl]-3b-(4"-chlorophenyl)tropane-2b-carboxylic acid methyl ester (3.20)

Yield (263 mg) 77.5%; mp 69–71° C.; IR ($CHCl_3$) 1743 $cm^{-1}$; 1H NMR (300 MHz) d 1.7 (m, 4H), 2.05 (m, 3H), 2.17 (m, 3H), 2.60 (dt, $J_1$=2.97, $J_2$=12.39, 1H), 2.94 (m, 2H), 3.39 and 3.64 (m, each 1H), 3.52 (s, 3H), 7.22 (m, 4H); HRMS (FAB) m/z 339.1060 calculated for $C_{17}H_{22}O_2NSCl$, $M^+$ +1, 340.1141. Anal. calculated for $C_{17}H_{22}O_2NSCl$: C, 60.17; H, 6.48. Found: C, 56.72; H, 5.83.

c. N-[2'-(mercapto)propyl]-3b-($4^{11}$-fluorophenyl)tropane-2b-carboxylic acid methyl ester (3.21)

Yield 71%; waxy solid; IR ($CHCl_3$) 1741 cm−1; 1H NMR (300 MHz) d 1.49 and 2.09 (m, each 6H), 2.53 (dt, J1=2.88, J2=12.27, 1H), 2.86 (t, J=4.2, 1H), 2.95 (td, J1=4.83, J2=12.27, 1H), 3.32 and 3.59 (m, each 1H), 3.43 (s, 3H), 6.9 and 7.1 (m, each 2H); HRMS (FAB) m/z 337.1512 calculated for $C_{18}H_{24}O_2NSF$, M++1, 338.1579.

d. N-[2'-(mercapto)propyl]-3b-(4"-chlorophenyl)tropane-2b-carboxylic acid methyl ester (3.22)

Yield 66%; waxy solid; IR ($CHCl_3$) 1741 cm−1; d 1.7 (m, 6H), 2.05 (m, 3H), 2.17 (m, 3H), 2.60 (dt, J1=2.97, J2=12.39, 1H), 2.94 (m, 2H), 3.39 and 3.64 (m, each 1H), 3.52 (s, 3H) and 7.22 (m, 4H); HRMS (FAB) m/z 353.1216 calculated for $C_{18}H_{24}O_2NSCl$, M++1, 354.1211.

Example 26

Radiolabeling with [$^{99m}$Tc] Described For Ligand Mixture 3.20 And 3.7 (3.25)

A lyophilized sample of a mixture of 3.20 (3 μmol) and 3.7 (2 μmol) was dissolved in 200 μL $CH_3CN$, and 100 μL 1N-HCl and 1 mL Sn-glucoheptonate were successively added. [$^{99m}$Tc]Pertechnetate (1 mL; ranging from 1 to 90 mCi) saline solution was then added. The reaction was allowed to stand at room temperature for 30 minutes. After extracting the complex from the aqueous reaction medium with ethyl acetate (2×1.5 mL) and drying the organic solution over $Na_2SO_4$, ethyl acetate was removed with a flow of $N_2$. The residue was dissolved in 200 microlitre ethyl acetate and purified by HPLC on a PRP-1 column (250×4.1 mm) with $CH_3CN$/DMGA buffer (5 mM, pH 7; 8:2) as eluent and a flow rate of 1 mL/minute. The retention time of 3.25 was 16.6 min (radiochemical yield 40%, radiochemical purity >95%). All the complexes displayed stability at 4 and 24 h after preparation; little change in radiochemical purity was observed. Identical labeling procedures were used for the preparation of the labeled complexes 3.24 to 3.34, with radiochemical yields of 46, 40, 36, 46, 20, 10, 33, 22, 10, 5 and 21%, respectively (radiochemical purities were all >95%).

Example 27

Evaluation

27a. Partition Coefficients

The partition coefficient was measured by mixing the Tc-99m compound with 3 g each of 1-octanol and buffer (pH 7.0 or 7.4, 0.1 M phosphate) in a test tube. The test tube was vortexed for 3 min at room temperature, then centrifuged for 5 minutes. Two weighed samples (0.5 g each) from the 1-octanol and buffer layers were counted in a well counter. The partition coefficient was determined by calculating the ratio of cpm/g of octanol to that of buffer. Samples from the octanol layer were repartitioned until consistent partition coefficient values were obtained. The measurement was repeated 3 times.

The complexes with gem-dimethyl groups, [$^{99m}$Tc] 3.26 and 3.27, displayed a much higher partition coefficient than those without, [$^{99m}$Tc] 3.24 and 3.25. In addition, the partition coefficient of the complex containing the fluorine atom, [$^{99m}$Tc] 3.24 and 3.26, is always lower than the corresponding complex with the chlorine atom. It is apparent that the partition coefficient of [$^{99m}$Tc] 3.25 appears to be the best among this series of three plus one Tc complexes.

The lipophilicities of [$^{99m}$Tc] 10–13 (described in Example 26) were measured by partition between n-octanol and buffer (Table 3.1).

27b. In vitro Autoradiography

Male Sprague-Dawley rats (200–250 mg) were sacrificed by decapitation, and the brains were removed, placed in OTC embedding medium (Miles Laboratory, Elkhart, Ind.) frozen in powdered dry ice. After equilibration to −15° C., 20 μm coronal sections were sliced on a cryostat (Hacker Instruments, Fairfield, N.J.), thaw mounted onto gelatin-coated slides, desiccated at 4° C. for 3 hours and kept at −70° C. until use. Prior to the experiment, the slides were dried at room temperature and preincubated for 30 minutes in buffer containing 50 mM Tris-HCl (pH 7.4, 120 mM NaCl). The slides were then incubated for 2 hours in preincubation buffer and the [$^{99m}$Tc] compound 3.25 (385,000 cpm/200 μL) in a coplan jar, washed for 1 hour in cold Tris buffer, with one change of buffer, dipped in ice-cold water to remove buffer salts and allowed to dry at room temperature. Nonspecific binding was determined in the presence of 1 μM IPT. These slides were simultaneously exposed to DuPont x-ray film in an autoradiographic cassette for 18 hours. The exposed film was developed with a Kodak automatic film processor.

27c. In vivo Biodistribution

Male Sprague-Dawley rats (225–300 g) that were allowed free access to food and water were used for in vivo biodistribution studies. (Kung, 1984, supra; Kung, 1985, supra). While under halothane anesthesia, 0.2 mL of a saline solution containing 3.24 to 3.34 (50–100 MCi) was injected directly into the femoral vein of rats, and they were sacrificed by cardiac excision at various time points post-injection. The organs of interest were removed and weighed, and the radioactivity was counted with an automatic gamma counter (Packard 5000). The percentage dose per organ was calculated by a comparison of the tissue counts to suitably diluted aliquots of the injected material. Total activities of blood and muscle were calculated under the assumption that they were 7% and 40% of the total body weight, respectively.

Regional brain distribution in rats was obtained after an injection of 3.24 to 3.34. Samples from different brain regions (cortex, striatum, hippocampus, and cerebellum) were dissected, weighed and counted, and the percentage dose per gram of sample was calculated by comparing the sample counts with the count of the diluted initial dose. The uptake ratio of each region was obtained by dividing the percentage dose per gram of that region by that of the cerebellum. For blocking studies, rats were injected with either β-CIT or haloperidol (iv, 1 mg/Kg) 5 min prior to injection of 3.25. The rats were dissected and brain tissue samples were counted as described above.

The brain uptakes of these complexes appeared to be similar and were all relatively low (0.1% dose/organ or less at 2 minutes post-injection) despite the different lipophilicities measured by partition coefficient between n-octanol and phosphate buffer (Tables 3.1). Slow washout from the brain was observed for all these complexes. Interestingly, only complexes 3.24 and 3.25, without any gem-dimethyl groups, displayed specific uptake in striatum, where dopamine transporters are highly concentrated; striatum to cerebellum ratio (ST/CB) was 1.93 and 2.2 at 30 minutes post-injection for [$^{99m}$Tc] 3.24 and 3.25, respectively. The cerebellum area, which does not contain dopamine transporters, was used as the background region for comparison.

Biodistribution of a [$^{99m}$Tc] compound 3.25 at 2, 30, 60, and 120 minutes post intravenous injection indicated that the complex followed the initial blood flow and localized in organs with high blood flow, such as muscle, liver, and kidney. The [$^{99m}$Tc] complex 3.25 cleared from muscle, while liver accumulation increased with time (Table 2). Accumulation of radioactivity was highest in all brain regions at 2 minutes post intravenous injection and declined gradually over the 120 minute period. The washout was slowest from the striatal region, followed by cortex, and hippocampus. Maximum regional contrast ratio observed for striatum(ST)/cerebellum(CB) was 2.2 and 3.5 at 30 and 60 minutes post-injection, respectively (Table 3). Therefore, additional blocking studies in rats were performed at this time point to further characterize the uptake of this [$^{99m}$Tc] compound. In this series of regional brain uptake studies in rats, the ST/CB ratio at 60 minutes after injection was 2.6 (FIG. 1). The specific uptake of the [$^{99m}$Tc] compound 3.25 in striatum could be blocked by pretreating rats with a dose of RTI-55 (N-methyl-2b-carbomethoxy-3b-(4-iodophenyl) tropane) (1 mg/kg, iv), a dopamine transporter ligand (ST/CB=1.0); but not with haloperidol (1 mg/kg, iv), an agent with a mixed pharmacological profile (binding to various CNS receptors but not to the dopamine transporter); no blocking effect was observed (ST/CB=2.6; FIG. 1). The results suggested that the uptake in the striatum of rat brain was specifically related to the dopamine transporter.

In vitro autoradiography of rat brain sections incubated with a [$^{99m}$Tc] compound 3.25 exhibited elevated labeling in striatum, major islands of Calleja and olfactory tubercle regions, where dopamine neurons are known to be concentrated. See Malison, R. T. et al. *J. Nucl. Med.* 1995, in submission; Mozley, P. D. et al. *J. Nucl. Med.* 1995, in press; Neumeyer, J. L. et al. *J. Med. Chem.* 1994, 37, 1558–1561.

Example 28

Figure 13:
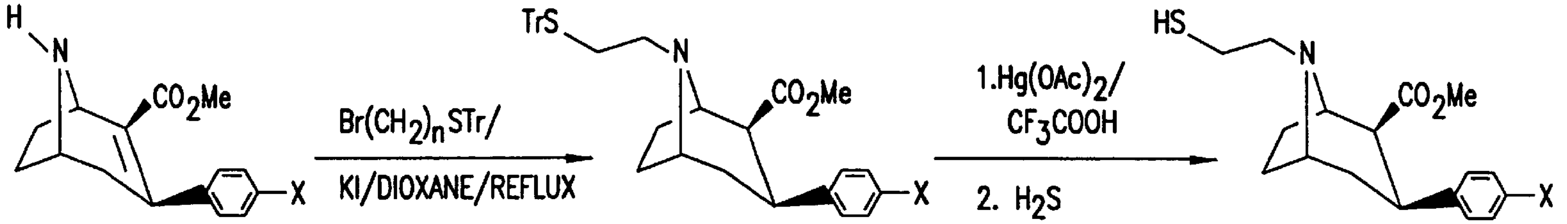
FIG. 13 depicts a reaction scheme that may be used for synthesizing a monothiol compound that is useful as an intermediate for preparing three plus one complexes of the invention.

Experimental For Reaction Schemes Depicted in FIGS. 12–14

The aminobisethanethiol ligand with gem-dimethyl groups, 3.6, was synthesized according to a previously reported procedure (Ohmomo, 1992, supra), as shown in FIG. 12. The aminobisethanethiol ligand without gem-dimethyl groups, 3.7, was synthesized according to the literature (Kolb, 1994, supra). The N-ethyl substituted aminobisethylthiols, 3.8, were prepared according to the procedure employed for the synthesis of 7, using N-ethyl bischloroethyl amine as the starting material. The other N-substituted bisethanethiols, 3.9 to 3.12, were prepared by bis-alkylation of benzyl-, iso-butyl-, morpholinoethyl- and (N,N-bisethylamino)ethyl-amine with ethylene sulfide, respectively. (Corbin, 1984, supra).

The syntheses of thiol tropane ligands 3.19 to 3.22 are shown in Scheme 13. Demethylated tropane derivatives 3.13 and 3.14 were prepared from cocaine in 4 steps, as previously reported (Meltzer, 1993, supra). N-alkylation was achieved by reacting them with S-trityl protected 2-bromoethanethiol and 3-bromopropanethiol (Dhar, 1994, supra), and the resulting alkylated products, 3.15–3.18, were successfully deprotected with Hg(OAc)2 to produce free thiols 3.19–3.22. Although the bis-alkylation of amines with ethylene sulfide generally produced the expected bis-ethanethiols in poor yields, it provided a very short route for obtaining the required dithiols quickly for the initial studies. No attempts were made to improve the yields of these reactions. The vacuum distillation yielded fairly pure dithiols but further reduced the yields. The dithiols seem to have only moderate stability and tend to produce a white solid, presumably disulfides, over time. However, the monothiols, 3.15–3.18, seem to have fairly good stability when stored at a low temperature under $N_2$. As is evident from the X-ray crystallographic structure of Re-complex 3.23, none of the reaction conditions employed in preparation of monothiols 3.15–3.18 and the Re complex altered the stereochemistry at the C-2 position of tropane ring.

Labeling with [$^{99m}$Tc] was carried out by reacting the appropriate ligands in a molar ratio of 1:1.5 (aminobisethanethiol:tropanethiol ligand) with sodium [99mTc]pertechnetate, in the presence of tin(II) glucoheptonate as a reducing agent at room temperature, with yields of about 40% (FIG. 14).

Byproducts were labeled complexes in which either the tridentate ligand aminobisethylthiol or the monothiol is complexed to a TcO-core to form neutral binuclear complex $Tc_2O_2[RN(CH_2CH_2S)_2]_3$ (Ravert, 1983, supra) and ionic complexes (Spies, 1990, supra).

The labeled compounds were purified by HPLC and final radiochemical purity of >95% was obtained. All of the [99mTc] complexes 3.24–3.34 displayed good in vitro stability. The lipophilicities of 3.24–3.34 were measured by partition between n-octanol and buffer (Table 3.1). The complexes with gem-dimethyl groups, 3.26 and 3.27, displayed a much higher partition coefficient than the analogous complexes, 3.24 and 3.25, without gem-dimethyl groups. In addition, the partition coefficients of the complexes containing the fluorine atom, 3.24, 3.26 and 3.28, are always lower than those of the corresponding complexes with the chlorine atom. In the series of alkyl substituted $NS_2$-ligand complexes, 3.25, 3.30 and 3.31, the partition coefficient follows an expected trend; the PC increases with the size of alkyl substituent (the PC's for N-methyl, N-ethyl and N-i-butyl are 307, 369 and 881, respectively). Having a hetero atom in the substitution group at the $NS_2$-part (3.33, 3.34) did not follow any general trend in partition coefficient.

Figure 17A:
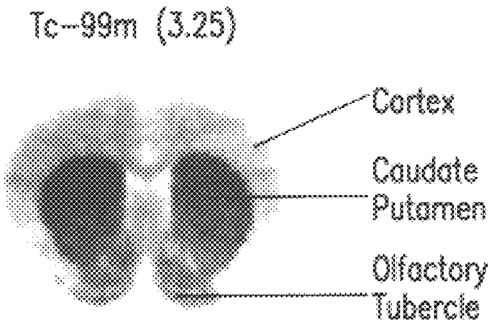
FIGS. 17A–17B depict an in vitro autoradiogram of 3.25 binding to dopamine transporters in a rat brain section demonstrated that it localized in caudate putamen and olfactory tubercle, areas known to have a high dopamine transporter density. A comparable section labeled with [$^{125}$I]IPT, a known iodinated dopamine transporter ligand, Kung, 1995, supra, showed an almost identical regional labeling pattern. The coronal section of rat brain shown corresponds to Plate 17 in the atlas by Paxinos and Watson. Paxinos, G. et al. The Rat Brain In Stereotaxic Coordinates (New York, Academic Press 1986).
Figure 17B:
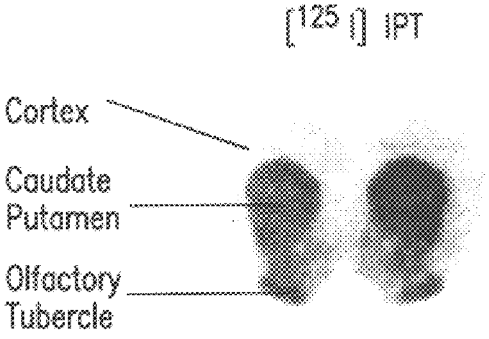

Coinjections of Tc-99m and Re-3.23 into HPLC under various elution conditions appeared to confirm that they have a similar retention time. It is likely that the Tc-99m complexes have the same chemical structures as those of the corresponding Re-complexes. Compounds 3.25 and 3.23 behaved similarly under identical HPLC conditions (coinjection), suggesting that 3.23 is indeed a good surrogate for 3.25. The retention time of 3.25 is similar to that of 3.23; on a C-18 column (Partisil 10-ODS-3, 250×4.6 mm) with $MeOH/NH_4HCO_3$ (0.1M, pH 7, ratio 8:2, flow rate 1 mL/min) as the eluent, the retention times were 14.9 and 15.3 min for 3.25 and 3.23, respectively (FIG. 17). On a Chiralpak AD column (250×4.6 mm) with hexane/EtOH (1:1, flow rate 1 ml/min) as the eluent, the retention times were 10.4 and 10.9 min for 3.25 and 3.23, respectively. On a PRP-1 column (Hamilton 250×4.1 mm) with CH3CN/dimethylglutarate buffer (5 mM, pH 7, ratio 9:1, flow rate 1 ml/min) as the eluent, the retention times were 10.2 and 9.8 minutes for 3.25 and 3.23, respectively. Whether the 99mTc complex has indeed the same chemical structure as Re complex 3.23 (methyl anti to the Re=O) cannot be determined definitively at this point. Under the applied conditions, only one of the two possible isomers (anti or syn) can be detected. If the other isomer is indeed present, the ratio must be >98:2 and the compounds must behave very similarly.

In vivo biodistribution studies of various Tc-99m labeled complexes, 3.24–3.34, were evaluated in male Sprague-Dawley rats. The brain uptakes of these complexes appeared to be similar and were all relatively low (0.1% dose/organ or less at 2 min post-injection) despite the different lipophilicities measured by partition coefficient between n-octanol and phosphate buffer (Table 3.1). Slow washout from the brain was observed for all these complexes. Interestingly, only complexes without any gem-dimethyl groups displayed specific uptake in striatum, where dopamine transporters are highly concentrated. Furthermore, only complexes with smaller R groups on the NS2-ligand showed any specific brain uptake; striatum to cerebellum ratio (ST/CB) was 1.93, 2.2 and 1.97 at 30 minutes post-injection for 3.24, 3.25 and 3.30, respectively. Increasing the chain length in the tropane thiol ligand from two to three carbons (compounds 3.28 and 3.29) did not change the brain uptake dramatically, but the ST/CB ratio was decreased (1.71 and 1.72, respectively). The cerebellum area, which does not contain dopamine transporters, was used as the background region for comparison.

Figure 15:
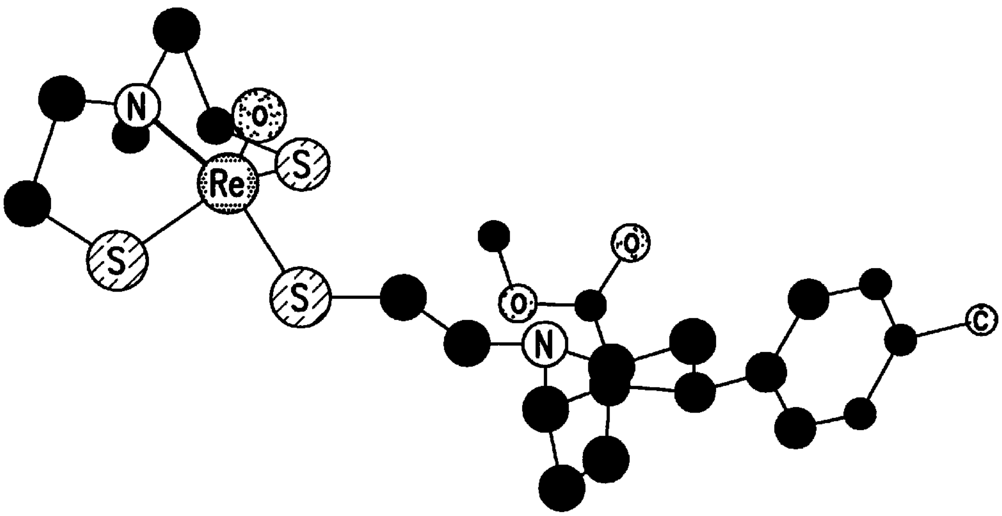
FIG. 15 depicts an X-ray crystallographic structure of rhenium complex containing a tropane moiety, 3.23. Meegalla, 1995, supra.
Figure 16:
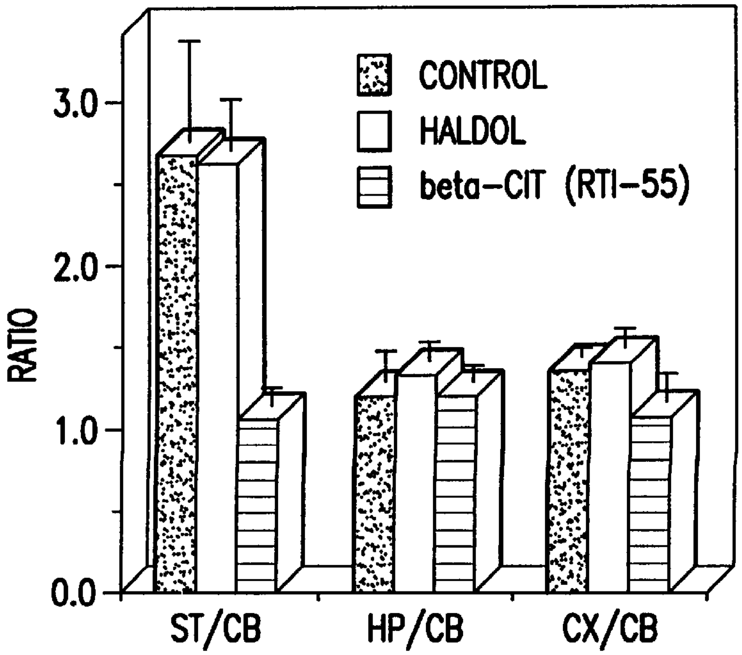
FIG. 16 depicts ratios of regional brain uptakes at 60 minutes post-intravenous injection of 3.25 in control rats and rats pretreated with haldol (1 mg/kg, iv) or β-CIT (1 mg/kg, iv) at 5 minutes prior to radiotracer injection. Values shown are means ±SD (n=3–4, $p<0.05$, student t-test). ST: striatum; HP: hippocampus; CX: cortex; CB: cerebellum. The ST area, where dopamine transporters are located, displayed selective regional brain uptake, with the highest concentration ratio (ST/CB=2.6). Pretreatment with β-CIT, which competes with dopamine transporter binding, showed blocking of the specific uptake of 3.25 in the ST area, where dopamine transporters are located.

Biodistribution showed that 3.25 had the highest ST/CB ratio (2.2) after 30 minutes post intravenous injection. Therefore 3.25 was studied further in rats. The study at 2, 30, 60 and 120 min post intravenous injection indicated that the complex followed the initial blood flow and localized in organs with high blood flow, such as muscle, liver and kidney. The Tc-99m complex cleared from muscle, while liver accumulation increased with time (Table 3.2). Accumulation of radioactivity was highest in all brain regions at 2 minutes post intravenous injection and declined gradually over the 120 minute period. The washout was slowest from the striatal region, followed by cortex and hippocampus. Maximum regional contrast ratio observed for striatum/cerebellum (ST/CB) was 3.5 at 60 minutes post-injection (Table 3.3). Therefore, additional blocking studies in rats were performed at 60 minutes post-injection to further characterize the uptake of this Tc-99m compound. In this series of regional brain uptake studies in rats, the ST/CB ratio at 60 min post-injection was 2.6 (FIG. 15). The specific uptake of 3.25 in striatum could be blocked by pretreating rats with a dose of β-CIT (1 mg/kg, iv), a dopamine transporter ligand (ST/CB=1.0); but not with haldol (1 mg/kg, iv), an agent with a mixed pharmacological profile (binding to various CNS receptors but not to the dopamine transporter); no blocking effect was observed. The ST/CB ratio (2.6) was identical to that in control rats (FIG. 15). The results suggested that uptake in the rat striatum was specifically related to the dopamine transporter. In addition, in vitro autoradiography of a rat brain coronal section incubated with 3.25 clearly demonstrated a regional distribution pattern of intense labeling in caudate putamen and olfactory tubercle, areas known to have a high density of dopamine transporters (FIG. 16).

Example 29

Comparison Study Of Technetrin And Rhenium Complexes

To further characterize the chemical structure of the technetium complexes, the corresponding ReO(III) complex, Re-3.25, was prepared and characterized (Kung, *J. Amer. Chem. Soc.*, in submission; Meegalla, 1995, supra). The non-radioactive rhenium is chemically close to technetium-99, but without the usual hazards associated with the handling of radioactive material. X-ray crystallography of the heterodimeric complex, Re-3.25, displayed an expected structure, with a pyramidal Re=O core and a N-methyl group at the anti position to the Re=O functionality. In vitro binding studies with rat striatal homogenates displayed excellent binding affinity (Ki=0.3 nM, using $[^{125}I]$-IPT as the ligand; Kd=0.2 nM).

In vitro binding studies of Re complex 3.23 with rat striatal homogenates displayed excellent binding affinity (Ki=0.3 nM, using [125I]-IPT as the ligand; Kd=0.2 nM). Kung, 1995, supra. The major drawback of this series of agents is that the brain uptake (0.1% dose/organ in rat brain at 2 min post intravenous injection) is too low to be useful for human imaging study. New complexes that produce at least 0.5% dose/organ in rat brain must be obtained before any are further developed as dopamine transporter imaging agents. Nevertheless, this series of $[^{99m}Tc]$ mixed ligand complexes (aminobisethanethiol and monothiol complexed to a $TcO^{3+}$ center core) is the first example of technetium labeled agents displaying specific regional uptake in rat brain that reflects receptor distribution.

TABLE 3.1

Partition coefficient, brain uptake and striatum/cerebellum ratios of various Tc-99m complexes

| Com-plex | Retention Time (min)/ Partition Coefficient | Brain Uptake (% dose) 2 min | Brain Uptake (% dose) 30 min | Striatum/ Cerebellum Ratios (30 min) | |
|---|---|---|---|---|---|
| 3.26 | 17.6*/1800 | 0.08 ± 0.03 | 0.05 ± 0.002 | 1.0 | (n = 3) |
| 3.24 | 11.6*/97 | 0.09 ± 0.01 | 0.063 ± 0.003 | 1.93 | (n = 3) |
| 3.27 | 27.4*/2000 | 0.051 ± 0.009 | 0.046 ± 0.002 | 1.0 | (n = 3) |
| 3.25 | 16.6*/307 | 0.100 ± 0.068 | 0.07 ± 0.003 | 2.2 | (n = 12) |
| 3.28 | 14.5*/99 | 0.082 ± 0.014 | 0.045 ± 0.008 | 1.71 | (n = 3) |
| 3.29 | 12.5#/125 | 0.12 ± 0.03 | 0.063 ± 0.013 | 1.72 | (n = 3) |
| 3.30 | 10.8#/369 | 0.097 ± 0.003 | 0.058 ± 0.006 | 1.97 | (n = 3) |
| 3.31 | 14.8#/881 | 0.080 ± 0.009 | 0.051 ± 0.006 | 0.97 | (n = 3) |
| 3.32 | 23.6#/146 | 0.048 ± 0.021 | 0.046 ± 0.20 | 0.72 | (n = 3) |

TABLE 3.1-continued

Partition coefficient, brain uptake and striatum/cerebellum ratios of various Tc-99m complexes

| Complex | Retention Time (min)/ Partition Coefficient | Brain Uptake (% dose) 2 min | 30 min | Striatum/ Cerebellum Ratios (30 min) | |
|---|---|---|---|---|---|
| 3.33 | 9.8#/86 | 0.062 ± 0.008 | 0.046 ± 0.009 | 0.47 | (n = 3) |
| 3.34 | 14.5#/92 | 0.11 ± 0.02 | 0.061 ± 0.011 | 0.53 | (n = 6) |

*Retention times of the complexes were measured by HPLC on a PRP-1 column (250 × 4.1 mm) eluted with acetonitrile-5 mM dimethylglutaric acid buffer, pH 7 (80:20), flow rate: 1 mL/min.
#Retention times of the complexes were measured by HPLC on a PRP-1 column (250 × 4.1 mm) eluted with acetonitrile-5 mM dimethylglutaric acid buffer, pH 7 (90:10), flow rate: 1 mL/min.

-continued

| | |
|---|---|
| Vial E: | Sterile sodium phosphates, injection, USP (Abbott, lot 10-288-DK) |

One sterilized empty vial and one ethanol (absolute) vial.

Mix 1.95 mL of ethanol with 0.05 mL of 2N HCl in the sterilized empty vial. Add 0.1 mL of the mixture to Vial A and shake well. Add 0.2 mL of the solution from Vial B to Vial A and 1 mL of the solution from Vial C to Vial A. Add 0.05 mL of the solution for Vial D to Vial A. Add Tc-99m solution (0.1–0.5 mL) to Vial A. Place Vial A in the autoclave at 112° C. for about 30 minutes. Following autoclaving, cool the reaction vial (A) to room temperature. When the compound is to be used for analysis, draw as much as the solution from vial A with a 5 mL syringe which is prefilled with 0.4 mL of sodium phosphate (Vial E) and mix well. Check the radiochemical purity of the residual aliquot in Vial A by TLC.

TABLE 3.2

Biodistribution of 3.25 in rats (intravenous injection; % dose/organ standard deviation, n = 3–6)

| Organ | 2 min | 30 min | 60 min | 120 min |
|---|---|---|---|---|
| Blood | 4.72 ± 1.37 | 2.75 ± 0.62 | 2.83 ± 0.42 | 2.31 ± 0.27 |
| Heart | 1.46 ± 0.37 | 0.30 ± 0.04 | 0.22 ± 0.23 | 0.12 ± 0.013 |
| Muscle | 23.30 ± 3.82 | 16.70 ± 3.62 | 13.63 ± 0.99 | 4.33 ± 1.20 |
| Lung | 6.41 ± 2.04 | 2.09 ± 0.47 | 1.26 ± 0.06 | 0.69 ± 0.061 |
| Kidney | 5.67 ± 0.94 | 3.10 ± 0.68 | 2.87 ± 0.43 | 2.74 ± 0.096 |
| Spleen | 0.36 ± 0.07 | 0.61 ± 0.10 | 0.50 ± 0.09 | 0.58 ± 0.009 |
| Liver | 13.51 ± 0.36 | 29.61 ± 2.22 | 32.15 ± 3.00 | 35.37 ± 1.52 |
| Skin | 2.94 ± 0.36 | 4.71 ± 1.27 | 4.57 ± 0.65 | 2.30 ± 0.082 |
| Brain | 0.10 ± 0.02 | 0.06 ± 0.02 | 0.046 ± 0.002 | 0.025 ± 0.002 |

TABLE 3.3

Regional brain distribution of 3.25 in rat brain (% dose/g)

| Region | 2 min | 30 min | 60 min | 120 min |
|---|---|---|---|---|
| Cerebellum | 0.066 ± 0.017 | 0.027 ± 0.006 | 0.018 ± 0.001 | 0.011 ± 0.002 |
| Striatum | 0.054 ± 0.010 | 0.060 ± 0.011 | 0.063 ± 0.001 | 0.031 ± 0.003 |
| Hippocampus | 0.046 ± 0.005 | 0.028 ± 0.008 | 0.025 ± 0.003 | 0.011 ± 0.000 |
| Cortex | 0.060 ± 0.009 | 0.038 ± 0.007 | 0.026 ± 0.002 | 0.015 ± 0.003 |
| ST/CB ratio | 0.82 | 2.2 | 3.5 | 2.8 |

Example 30

Kit Formulation For Compound 1.19a

A kit would contain: compound 1.19a (180–250 mg); stannous chloride (100–200 mg); sodium glucoheptonate (200–400 mg); disodium EDTA (300–350 mg); 2.0 N hydrochloric acid (200–250 mL); and ethanol (100–200 mL).

Preparation of compound 1.19a using kit formulation:

| | |
|---|---|
| Vial A (reaction vial): | 200 micrograms 1.19a |
| Vial B: | 2N HCl solution |
| Vial C: | $SnCl_2$/glucoheptonate, pH 6.7 |
| | Stannous chloride anhydrous (100 mg/mL) |
| | Sodium glucoheptonate (200 mg/mL) |
| Vial D: | 0.05 mL EDTA |
| | 0.1 M Sodium EDTA |

What is claimed is:

1. A compound of the formula

I

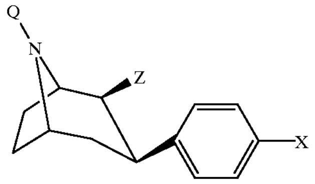

wherein

X is selected from the group consisting of H, $C_1$–$C_4$ alkyl, F, Cl, Br, and I;

Q is selected from the group consisting of $A_1$, $A_2$, $A_7$, and $A_8$;

Z is selected from the group consisting of R, $CNRR_1$, $COR_1$, $CO_2R_1$, and $CO_2R_2$;

R is H, or $C_1$–$C_5$ alkyl;

$R_1$ is H, or $C_1$–$C_5$ alkyl;

$R_2$ is a heterocyclic amine, $A_1$ is $A_2$ is

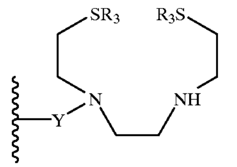

$A_7$ is

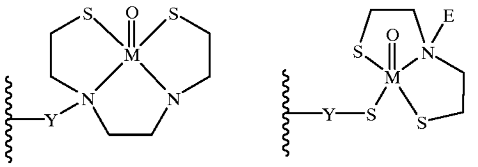

$A_8$ is

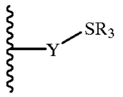

E is $C_1$–$C_2$ alkyl;

Y is $(CH_2)_n$;

n is 0, 1, 2, 3, 4, or 5;

M is selected from the group consisting of Tc and Re;

$R_3$ is selected from the group consisting of H, $CR_4$, substituted or unsubstituted $C_1$–$C_5$ alkoxy, substituted or unsubstituted $C_6$–$C_{24}$ aryl, and substituted or unsubstituted phenylalkoxy; and $R_4$ is selected from the group consisting of H and $C_1$–$C_5$ alkyl, optionally substituted with a substituted or unsubstituted phenyl group.

2. The compound of claim 1 wherein said Q moiety includes a compound selected from the group $A_1$, $A_2$, $A_7$, and $A_8$.

3. The compound of claim 1 wherein X is $C_1$–$C_4$ alkyl, F, Cl, Br, or I; $R_3$ is H; Q is $A_1$ or $A_2$; Z is $CO_2R_1$ or $CO_2R_2$; and M is Tc.

4. A compound of the formula

I

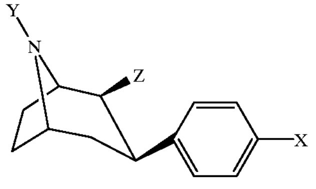

wherein

X is selected from the group consisting of H, F, Cl, Br and I;

Y is selected from the group consisting of $A_1$, $A_2$, and $A_3$;

Z is selected from the group consisting of H, $CO_2R_1$, $COR_1$, $CNR_1$, and $CNOR_1$;

$R_1$ is $C_1$–$C_4$ alkyl;

$A_1$ is

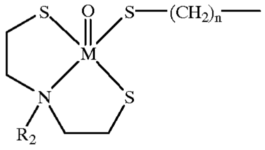

$R_2$ is selected from $CH_3$ and $CH_2CH_3$;

$A_2$ is

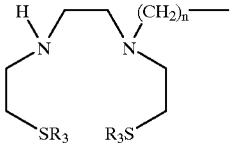

$A_3$ is

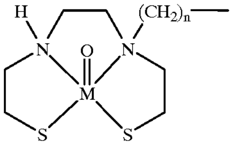

n is 1, 2, 3, or 4;

M is selected from the group consisting of Tc and Re;

$R_3$ is selected from the group consisting of H, $CR_4$, $CO_2R_4$, $CHOR_4$, $CH_2$, $NHR_4$, $C(O)NH_4$, substituted or unsubstituted $C_1$–$C_5$ alkoxy, substituted or unsubstituted $C_6$–$C_{24}$ aryl, and substituted or unsubstituted phenylalkoxy; and $R_4$ is selected from the group consisting of H and $C_1$–$C_5$ alkyl, optionally substituted with a substituted or unsubstituted phenyl group.

5. A diagnostic method for monitoring neuronal functions in a mammal, comprising:

(a) introducing into a mammal a compound according to claim 1.

6. A diagnostic kit comprising:

(a) a lyophilized composition comprising a compound according to claim 1; and (b) a reducing agent.

7. The compound of claim 1 wherein X is Cl, F, or Br.

8. The compound of claim 1 wherein Z is $CO_2CH_3$.

9. The compound of claim 1 where X is Cl; Q is $A_1$; $R_3$ is H; and Z is $CO_2R_2$ or $CO_2CH_3$.

10. The compound of claim 1 where X is Br; Q is $A_1$; $R_3$ is H; and Z is $CO_2R_2$ or $CO_2CH_3$.

11. The compound of claim 1 where X is F; Q is $A_1$; $R_3$ is H; and Z is $CO_2R_2$ or $CO_2CH_3$.

12. The compound of claim 1 where X is Cl; Q is $A_2$; Z is $CO_2R_2$ or $CO_2CH_3$; and M is Tc.

13. The compound of claim 1 where X is Br; Q is $A_2$; Z is $CO_2R_2$ or $CO_2CH_3$; and M is Tc.

14. The compound of claim 1 where X is F; Q is $A_2$; Z is $CO_2R_2$ or $CO_2CH_3$; and M is Tc.

15. The compound of claim 1 where X is $C_1$–$C_4$ alkyl, F, Cl, Br, or I; Q is $A_7$ or $A_8$; Z is $CO_2R_1$ or $CO_2R_2$; and E is $C_1$–$C_2$ alkyl.

16. The compound of claim 1 where X is Cl; Q is $A_7$; Z is $CO_2CH_3$; E is $C_1$–$C_2$ alkyl; and M is Tc.

17. The compound of claim 1 where X is F; Q is $A_7$; Z is $CO_2CH_3$; E is $C_1$–$C_2$ alkyl; and M is Tc.

18. The compound of claim 1 where X is Br; Q is $A_7$; Z is $CO_2CH_3$; E is $C_1$–$C_2$ alkyl; and M is Tc.

19. The method of claim 1 wherein said diagnostic imaging is performed using single photon emission computed tomography.

20. The compound of claim 1 dissolved or dispersed in a pharmaceutically acceptable carrier or diluent.

21. The kit of claim 6 wherein said reducing agent is selected from the group consisting of stannous glucoheptonate, stannous chloride, stannous mannitol, sodium bisulfite, and combinations thereof.

* * * * *

UNITED STATES PATENT AND TRADEMARK OFFICE

CERTIFICATE OF CORRECTION

PATENT NO. : 6,241,963 B1
DATED : June 5, 2001
INVENTOR(S) : Kung et al.

It is certified that error appears in the above-identified patent and that said Letters Patent is hereby corrected as shown below:

Title page,
Item [56], OTHER PUBLICATIONS, delete "Kung et al., "Imaging of dopamine transporters in humans with technetium-99m TRODAT-1", *Eur. J. Nucl. Med.* 1996, 23(11), 1527-15230." and insert therein -- Kung et al., "Imaging of dopamine transporters in humans with technetium-99m TRODAT-1", *Eur. J. Nucl. Med.* 1996, 23(11), 1527-1530 --.

Column 57,
Line 3, delete "The method of claim 1" and insert therein -- The method of claim 5 --.

Signed and Sealed this

Third Day of September, 2002

*Attest:*

JAMES E. ROGAN

*Attesting Officer* *Director of the United States Patent and Trademark Office*